United States Patent
Law et al.

(10) Patent No.: US 10,493,118 B2
(45) Date of Patent: Dec. 3, 2019

(54) TRITERPENOID OBTAINABLE FROM HEDERA HELIX FOR TREATMENT OF NEURODEGENERATIVE DISEASES

(71) Applicant: Macau University of Science and Technology, Taipa (MO)

(72) Inventors: Yuen Kwan Law, Taipa (MO); Kam Wai Wong, Taipa (MO); An Gao Wu, Taipa (MO); Liang Liu, Taipa (MO); Zeng Wu, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 46 days.

(21) Appl. No.: 15/280,136

(22) Filed: Sep. 29, 2016

(65) Prior Publication Data

US 2018/0085413 A1 Mar. 29, 2018

(51) Int. Cl.
*A61P 25/28* (2006.01)
*A61K 36/25* (2006.01)
*A61K 31/704* (2006.01)
*A61K 31/56* (2006.01)
*A61K 31/19* (2006.01)

(52) U.S. Cl.
CPC .............. *A61K 36/25* (2013.01); *A61K 31/19* (2013.01); *A61K 31/56* (2013.01); *A61K 31/704* (2013.01); *A61P 25/28* (2018.01); *A61K 2236/33* (2013.01); *A61K 2236/35* (2013.01); *A61K 2236/39* (2013.01)

(58) Field of Classification Search
None
See application file for complete search history.

(56) References Cited

U.S. PATENT DOCUMENTS 9,205,113 B2 * 12/2015 Gribble .................... C07C 61/29
2015/0343005 A1 * 12/2015 Kim ...................... A61K 31/155
424/732

FOREIGN PATENT DOCUMENTS

CN  102697791 A * 10/2012 ............. A61K 31/56

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002.*
Xu, M. Y., Lee, D. H., Joo, E. J., Son, K. H., & Kim, Y. S. (2013). Akebia saponin PA induces autophagic and apoptotic cell death in AGS human gastric cancer cells. Food and chemical toxicology, 59, 703-708. (Year: 2013).*
Vingtdeux, V., Chandakkar, P., Zhao, H., d'Abramo, C., Davies, P., & Marambaud, P. (2011). Novel synthetic small-molecule activators of AMPK as enhancers of autophagy and amyloid-βpeptide degradation. The FASEB Journal, 25(1), 219-231. (Year: 2011).*
A.G. Wu, V.K. Wong, W. Zeng et al., "Identification of novel autophagic Radix Polygalae fraction by cell membrane chromatography and UHPLC-(Q)TOF-MS for degradation of neurodegenerative disease proteins", Sci. Rep. 2015, 5:17199.
A.G. Wu, V.K. Wong, S.W. Xu et al., "Onjisaponin B derived from Radix Polygalae Enhances Autophagy and Accelerates the Degradation of Mutant Alpha-Synuclein and Huntingtin in PC-12 Cells", Int. J. Mol. Sci. 2013, 14:22618-22641.
R.H.S. Westerink, A.G. Ewing, "The PC12 Cell as Model for Neurosecretion", Acta Physiol 2008, 192:273-285.
M. Maioli, S. Rinaldi, R. Migheli et al., "Neurological Morphofunctional Differentiation Induced by REAC Technology in PC12. A Neuro Protective Model for Parkinson's Disease", Sci. Rep. 2015, 5:10439.
M. Mehrpour, A. Esclatine, I. Beau, P. Codogno, "Overview of Macroautophagy Regulation in Mammalian Cells", Cell. Res. 2010, 20:748-762.
V. Mshvildadze, R. Elias, R. Faure et al., "Triterpenoid Saponins from Leaves of Hedera Pastuchowii", Chem. Pharm. Bull. 2004, 52:1411-1415.
R. Iancu, P. Mohapel, P. Brundin, G. Paul, "Behavioral Characterization of a Unilateral 6-OHDA-Lesion Model of Parkinson's Disease in Mice", Behavioural Brain Research 2005, 162:1-10.
F.L. Su, F. Wang, R.H. Zhu, H. Li, "Determination of 5-Hydroxytryptamine, Norepinephrine, Dopamine and Their Metabolites in Rat Brain Tissue by LC-ESI-MS-MS", Chromatographia 2009, 69:207-213.
G.E. Meredith, D.J. Rademacher, "MPTP Mouse Models of Parkinson's Disease: An Update", J. Parkinsons. Dis. 2011, 1:19-33.
F. Magrinelli, A. Picelli, P. Tocco et al., "Pathophysiology of Motor Dysfunction in Parkinson's Disease as the Rationale for Drug Treatment and Rehabilitation", Parkinson's Disease, vol. 2016, Art. ID 9832839, 18 pps.
R. Haobam, K.M. Sindhu, G. Chandra, K.P. Mohanakumar, "Swim-test as a function of motor impairment in MPTP model of Parkinson's disease: a comparative study in two mouse strains", Behav. Brain Res. 2005, 163:159-167.
R.M. Deacon, "Measuring Motor Coordination in Mice", J. Vis. Exp. 2013:e2609.

(Continued)

*Primary Examiner* — Dale R Miller
(74) *Attorney, Agent, or Firm* — Renner Kenner Greive Bobak Taylor & Weber

(57) ABSTRACT

A method for treating a subject suffering from a neurodegenerative disease includes administering at least one triterpenoid which can be obtained from *Hedera helix*. A method for treating a subject suffering from a neurodegenerative disease includes administering an effective amount of a *Hedera helix* extract which comprises the triterpenoid. The neurodegenerative disease is preferably but not exclusively Parkinson's disease or Huntington's disease. Methods for extracting the triterpenoid from *Hedera helix* and a method for inducing autophagy in cells by contacting them with the triterpenoid are also provided. The triterpenoid allows an exceptional induction of autophagy, in particular a significant reduction of the protein level of mutant huntingtin, a significant reduction of the protein level of A53T α-synuclein, a significant inhibition of the oligomerization of α-synuclein and a significant inhibition of the inclusion formation of huntingtin via the AMPK-mTOR dependent autophagy inducing pathway.

10 Claims, 43 Drawing Sheets

(56) References Cited

OTHER PUBLICATIONS

N. Mizushima, D.J. Klionsky, "Protein turnover via autophagy: Implications for metabolism", Annu. Rev. Nutr. 2007, 27:19-40.

R.J. Shaw, "LKB1 and AMPK control of mTOR signalling and growth", Acta Physiol 2009, 196:65-80.

B. Ravikumar, C. Vacher, Z. Berger et al., "Inhibition of mTOR induces autophagy and reduces toxicity of polyglutamine expansions in fly and mouse models of Huntington disease", Nat. Genet. 2004, 36:585-595.

C.C. He, D.J. Klionsky, "Regulation Mechanisms and Signaling Pathways of Autophagy", Annu. Rev. Genet. 2009, 43:67-93.

J.O. Pyo, J. Nah, Y.K. Jung ", Molecules and their functions in autophagy", Exp. Mol. Med. 2012, 44:73-80.

B. Ravikumar, S. Imarisio, S. Sarkar et al., "Rab5 modulates aggregation and toxicity of mutant huntingtin through macroautophagy in cell and fly models of Huntington disease", J. Cell. Sci. 2008, 121:1649-1660.

C.E. Wang, S. Tydlacka, A.L. Orr et al., "Accumulation of N-terminal mutant huntingtin in mouse and monkey modelsimplicated as a pathogenic mechanism in Huntington's disease", Hum. Mol. Genet. 2008, 17:2738-2751.

X.H. Lu, V.B. Mattis, N. Wang et al., "Targeting ATM ameliorates mutant Huntingtin toxicity in cell and animal models of Huntington's disease", Sci. Transl. Med. 2014, 6:268ra178.

T.F. Outeiro, P. Putcha, J.E. Tetzlaff et al., "Formation of toxic oligomeric α-synuclein species in living cells", PLoS One 2008, 3:e1867.

S. Sarkar, J.E. Davies, Z. Huang et al., "Trehalose, a novel mTOR-independent autophagy enhancer, accelerates the clearance of mutant huntingtin and alpha-synuclein", J. Biol. Chem. 2007, 282:5641-5652.

L. Breydo, J.W. Wu, "Uversky VN: Alpha-synuclein misfolding and Parkinson's disease", Biochim Biophys Acta 2012, 1822:261-285.

S. Wang, H. He, L. Chen et al., "Protective effects of salidroside in the MPTP/MPP(+)-induced model of Parkinson's disease through ROS-NO-related mitochondrion pathway", Mol. Neurobiol. 2015, 51:718-728.

* cited by examiner

TRITERPENOID OBTAINABLE FROM HEDERA HELIX FOR TREATMENT OF NEURODEGENERATIVE DISEASES

TECHNICAL FIELD

The present invention relates to a method for treating a subject suffering from a neurodegenerative disease by administering at least one triterpenoid which can be obtained from *Hedera helix*. Further provided is a method for treating a subject suffering from a neurodegenerative disease by administering an effective amount of a *Hedera helix* extract which comprises the triterpenoid. The neurodegenerative disease is preferably but not exclusively Parkinson's disease or Huntington's disease. The present invention also provides methods for extracting the triterpenoid from *Hedera helix* and a method for inducing autophagy in cells by contacting them with the triterpenoid.

BACKGROUND OF INVENTION

Pathogenesis of neurodegenerative diseases such as Parkinson's disease and Huntington's disease are closely related to the formation of protein aggregates and inclusion bodies which finally lead to degeneration of neuronal cells and brain regions mainly affecting the motor system and mental functions. Huntingtin inclusions with expansion of CAG repeats were found in degenerated regions of the brain, whereas accumulation of Lewy bodies in the cytoplasm of neurons is one cause of Parkinson's disease.

Autophagy, a cellular lysosomal degradation mechanism responsible for recycling excessive or damaged organelles and protein aggregates, has become an attractive therapeutic strategy for neurodegenerative diseases. The beneficial effect is correlated with the removal of toxic protein aggregates and the adaptation of responses to stress.

For instance, active autophagic compounds from Chinese herbal medicines (CHMs) are highlighted to modulate neurodegeneration via degradation of disease proteins. Chinese herbal medicines usually allow for treatment of various diseases and conditions while bearing a reduced risk for side effects. In view of the rich medicinal plant resources, respective medicines can usually be produced in a cost-effective way.

As treatment options for neurodegenerative diseases are limited, there remains a strong need for novel autophagic enhancers such as from CHM sufficiency effective in treating neurodegenerative diseases while having acceptable toxicity.

SUMMARY OF INVENTION

The first aspect of the present invention relates to a method for treating a subject suffering from a neurodegenerative disease, which is in particular associated with the aggregation of at least one specific protein in neuronal cells and/or the formation of inclusion bodies such as Parkinson's disease or Huntington's disease. The subject is in particular a mammal such as a human.

Said method of the present invention comprises a step of administering an effective amount of at least one triterpenoid to the subject, which triterpenoid has a structure of Formula (I):

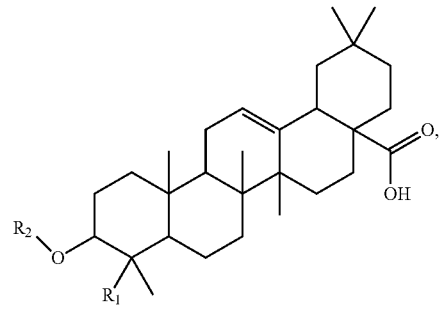

Formula (I)

wherein $R_1$ is —$CH_3$ or —$CH_2OH$, in particular $R_1$ is —$CH_2OH$. $R_2$ is H or a glycoside moiety which, in particular, comprises α-L-rhamnose (α-L-Rha) and α-L-arabinose (α-L-Ara) linked by glycosidic bond such as α-L-Rha(1→2) α-L-Ara(1→)-, i.e.

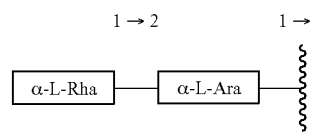

which can be expressed with the structure of Formula (III):

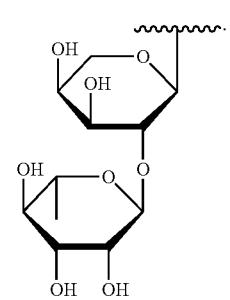

Formula (III)

At least two or more triterpenoids falling under Formula (I) can be administered. The at least one triterpenoid in particular has a structure of Formula (II):

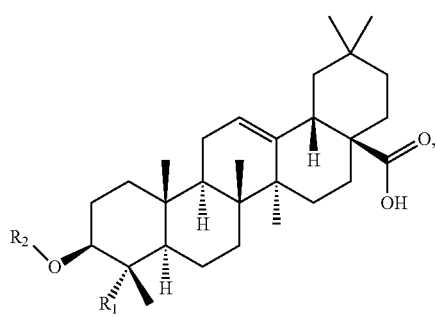

Formula (II)

wherein $R_1$ and $R_2$ are as defined above.

In particular embodiments, the at least one triterpenoid has a structure of Formula (IV):

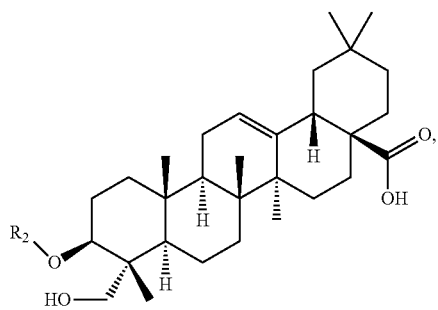

Formula (IV)

wherein R₂ is H or a glycoside moiety in particular α-L-Rha(1→2)α-L-Ara(1→)-, i.e.

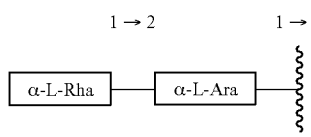

For example, the at least one triterpenoid has a structure of Formula (V):

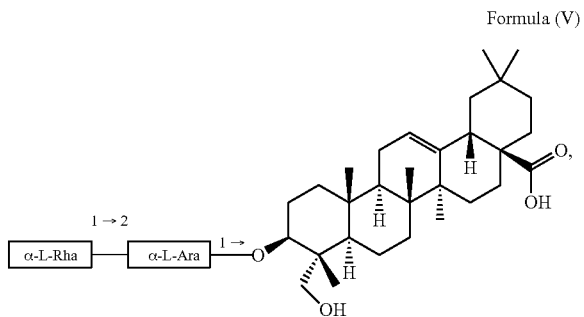

Formula (V)

i.e. R₂ in Formula (IV) is α-L-Rha(1→2)α-L-Ara(1→)- which triterpenoid is known as α-hederin, or the at least one triterpenoid has a structure of Formula (VI):

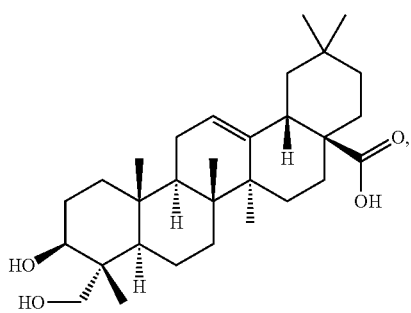

Formula (VI)

i.e. R₂ in Formula (IV) is H which triterpenoid is known as hederagenin.

The at least one triterpenoid can be administered in form of an extract obtained from *Hedera helix*.

The at least one triterpenoid is in particular obtained from *Hedera helix* by an extraction comprising steps of:

(i) subjecting *Hedera helix* plant material which in particular comprises the whole plant to a solvent extraction with an extraction solvent for obtaining a *Hedera helix* crude extract, wherein the extraction solvent comprises an aliphatic alcohol, in particular ethanol;

(ii) contacting the *Hedera helix* crude extract with a first and a second separation solvent for obtaining a first and a second layer and separating the first layer from the second layer, wherein the first separation solvent comprises water and the second separation solvent comprises at least one hydrocarbon such as petroleum ether, and wherein the first layer comprises the triterpenoid and the main part of the first separation solvent;

(iii) contacting the first layer after step (ii) with a third separation solvent comprising an ester, in particular ethyl acetate, for forming a third layer comprising the at least one triterpenoid and the main part of the third separation solvent and separating the third layer from the first layer;

(iv) isolating the triterpenoid from the third layer.

In a second aspect, the present invention provides methods of extracting at least one triterpenoid from *Hedera helix* having a structure of Formula (I) as described above.

Further in accordance with the present invention is a method for treating a subject suffering from a neurodegenerative disease comprising the step of administering an effective amount of a *Hedera helix* extract comprising at least one triterpenoid, in particular an effective amount of said at least one triterpenoid, which at least one triterpenoid has a structure of Formula (I):

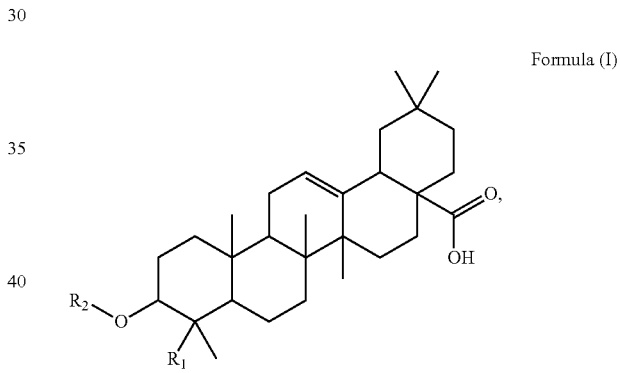

Formula (I)

to the subject. The *Hedera helix* extract is in particular obtained or obtainable by an extraction described above from *Hedera helix* plant material.

In another aspect, the present invention provides a method for inducing autophagy in neuronal cells from a subject with a neurodegenerative disease comprising contacting the cells with an effective amount of at least one triterpenoid, wherein the triterpenoid has a structure of Formula (I):

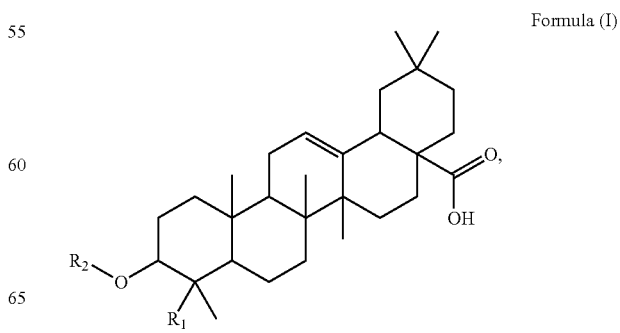

Formula (I)

in particular of Formula (II):

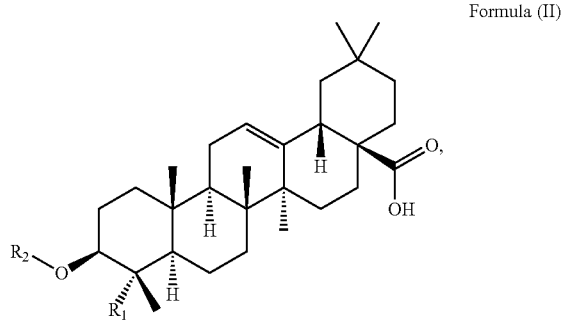

Formula (II)

wherein $R_1$ is —$CH_3$ or —$CH_2OH$ and $R_2$ is H or a glycoside moiety. The at least one triterpenoid is preferably obtained or obtainable by an extraction from *Hedera helix* described above.

The cells are neuronal cells such as from a mammal, for example a human, with a neurodegenerative disease such as Parkinson's disease or Huntington's disease. The triterpenoid for contacting the cells can have a structure of Formula (V):

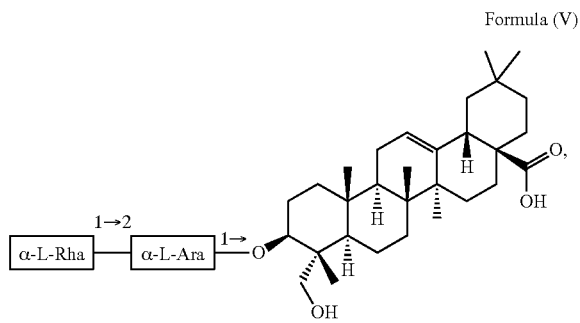

Formula (V)

and the cells are contacted with said triterpenoid in a concentration of about 12 µM to about 24 µM for at least 16 h. Alternatively, the at least one triterpenoid for contacting the cells can have a structure of Formula (VI):

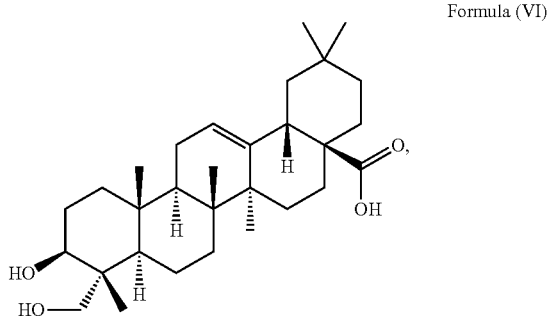

Formula (VI)

and the cells are contacted with said triterpenoid in a concentration of about 40 µM to about 80 µM for at least 8 h.

According to the invention is also the at least one triterpenoid described above, in particular of Formula (V) or (VI), for use as a medicament for the treatment of a neurodegenerative disease, in particular Parkinson's disease or Huntington's disease. Another aspect of the present invention refers to the use of the at least one triterpenoid described above, in particular of Formula (V) or (VI), for preparing a medicament for treatment of a neurodegenerative disease, in particular Parkinson's disease or Huntington's disease. The present invention also relates to the use of the at least one triterpenoid described above, in particular of Formula (V) or (VI), as neuroprotective compound for inducing autophagy.

The inventors unexpectedly found that the triterpenoid of Formula (I) having a carboxylic acid function at $C_{28}$ represents a highly promising treatment option for treating neurodegenerative diseases such as Parkinson's disease or Huntington's disease, namely it allows for an exceptional induction of autophagy in, in particular a significant reduction of the protein level of mutant huntingtin, a significant reduction of the protein level of A53T α-synuclein, a significant inhibition of the oligomerization of α-synuclein and a significant inhibition of the inclusion formation of huntingtin via the AMPK-mTOR dependent autophagy inducing pathway.

The inventors, in particular, confirmed a neuroprotective effect of a *Hedera helix* extract containing both triterpenoids of Formula (V) and (VI), i.e. α-hederin and hederagenin, namely an improvement of motor deficits in a Parkinson's disease mice model. In particular, compounds of Formula (V) and (VI) led to an exceptional increase in the protein levels of LC3-II and the LC3-II puncta formation, i.e. the formation of autophagosomes and autolysosomes. Such triterpenoids in particular proved to induce the autophagic flux, the degradation of mutant huntingtin via ATG7 gene dependent mechanism, the clearance of mutant huntingtin via autophagic induction. Further, the experimental results confirm that these triterpenoids advantageously facilitate the degradation of mutant A53T α-synuclein (α-syn) in doxycycline (Dox)-inducible cellular model and are even able to rescue cells from MPTP-induced cell death.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

FIG. 2A shows the fluorescent pattern of the cells treated with HH-WF, HH-NF, HH-EF, HH-PF and of a control group. It is evident from FIG. 2A that HH-EF increases in the formation of fluorescent LC3 autophagic puncta in PC-12 cells. FIG. 2B is a diagram showing the percentage of cells with fluorescent LC3 autophagic puncta formation in the control group and after treatment with HH-WF, HH-NF, HH-EF, and HH-PF.

FIG. 3A shows the blotted protein band patterns of proteins LC3-I and LC3-II and β-actin as reference control. FIG. 3B is a diagram showing the relative density of LC3-II in cells of the control group and in cells treated with HH-WF, HH-NF, HH-EF, or HH-PF determined via normalization to β-actin in the cells.

FIG. 6A shows the fluorescence patterns of cells treated with 30 μg/mL HH-NF(AHS)-WF, 30 μg/mL HH-NF(AHS)-EF and a control group. It is evident that HH-NF(AHS)-EF increases the formation of fluorescent LC3 autophagic puncta in PC-12 cells. FIG. 6B is a diagram showing the percentage of cells with fluorescent LC3 autophagic puncta formation of the control group and after treatment with HH-NF(AHS)-WF and HH-NF(AHS)-EF.

FIG. 7A shows the blotted protein band patterns of proteins LC3-I and LC3-II and β-actin. FIG. 7B shows the relative density of protein LC3-II in the cells determined via normalization to β-actin in the cells.

FIG. 16A shows the blotted protein band pattern of proteins LC3-I and LC3-II and β-actin. FIG. 16B shows the relative density of protein LC3-II in the cells determined via normalization to β-actin in the cells.

FIG. 17A shows the fluorescent pattern of the cells treated with hederagenin under different conditions, and positive control. FIG. 17B shows the percentage of cells having increased fluorescent LC3 autophagic puncta formation after treatments.

FIG. 18A shows the fluorescent pattern of the cells treated with α-hederin under different conditions, and positive control. FIG. 18B shows the percentage of cells having increased fluorescent LC3 autophagic puncta formation after treatments.

FIG. 19A shows the effect of hederagenin with blotted protein band patterns and relative amount of protein LC3-II in the treated cells. The cells were treated with 60 μM hederagenin in the presence or absence of E64d and pepstatin A (10 μg/mL) for different periods. FIG. 19B shows the effect of α-hederin with blotted protein band pattern and relative amount of protein LC3-II in the treated cells. The cells were treated with 18 μM α-hederin in the presence or absence of E64d and pepstatin A (10 μg/mL) for different periods.

FIG. 20A shows the effect of hederagenin with blotted protein band patterns and relative amount of protein LC3-II in the treated cells. The cells were treated with 60 μM hederagenin in the presence or absence of 5 mM 3-MA. FIG. 20B shows the effect of α-hederin with blotted protein band pattern and relative amount of protein LC3-II in the treated cells. The cells were treated with 18 μM α-hederin in the presence or absence of 5 mM 3-MA.

FIG. 21A shows the fluorescence patterns of the cells treated with 60 μM hederagenin or 18 μM α-hederin in the presence or absence of 5 mM 3-MA for 24 h, and the control group.

FIG. 21B is a diagram showing the fluorescent LC3 autophagic puncta formation after treatment and in the control group.

FIG. 22A shows the blotted protein band patterns of p-AMPK, total AMPK, p-p70S6K, total p70S6K and β-actin in the cells. FIG. 22B shows the relative density of p-AMPK and p-P70S6K in the cells determined via normalization to β-actin in the cells.

FIG. 23A shows the blotted protein band patterns and the relative amount of protein LC3-II present in the cells treated with 18 μM α-hederin with or without 5 μM CC. FIG. 23B shows the blotted protein band patterns and the relative amount of protein LC3-II present in the cells treated with 60 μM hederagenin with or without 5 μM CC.

FIG. 24A shows the fluorescence patterns of the cells treated with 60 μM hederagenin or 18 μM α-hederin in the presence or absence of 5 mM CC for 24 h and in the control group. FIG. 24B is a diagram showing the percentage of cells with fluorescent LC3 autophagic puncta formation after the treatment and in the control group.

FIG. 25A shows the fluorescent pattern of the cells treated with 12 μM or 24 μM α-hederin, or 40 μM, 60 μM or 80 μM hederagenin for 24 h, and control group. FIG. 25B shows the percentage of cells having fluorescent LC3 autophagic puncta formation after the treatment and in the control group.

FIG. 26A shows the blotted protein band patterns of proteins LC3-I, LC3-II, EGFP-HTT74 and β-actin. FIG. 26B is a diagram showing the relative amount of protein LC3-II in the cells. FIG. 26C is a diagram showing the relative amount of EGFP-HDQ74 in the cells. The relative amounts were determined via normalization to β-actin in the cells.

FIG. 27A shows the fluorescent pattern of the treated cells and control group. FIG. 27B is a diagram showing the percentage of cells having EGFP-HTT 74 inclusion formation after treatments.

FIG. 28A shows the blotted protein band patterns and relative amount of EGFP-HTT 74 in the cells treated with 0 μM, 40 μM, 60 μM or 80 μM hederagenin. FIG. 28B shows the blotted protein band patterns and relative amount of EGFP-HTT 74 in the cells treated with 0 μM, 12 μM, 18 μM or 24 μM α-hederin.

FIG. 29A shows the blotted protein band pattern of α-synuclein and β-actin. FIG. 29B shows the relative amount of α-synuclein in the cells.

FIG. 30A shows the percentage of cells with oligomerization of α-synuclein after treatment with flow cytometry analysis. FIG. 30B shows the percentage of cells with GFP fluorescence signal after treatment.

FIG. 33A shows the flow cytometry patterns of Annexin V conjugates in cells after the treatment. FIG. 33B is a diagram showing cell deaths after the treatment.

DETAILED DESCRIPTION OF INVENTION

Figure 1:
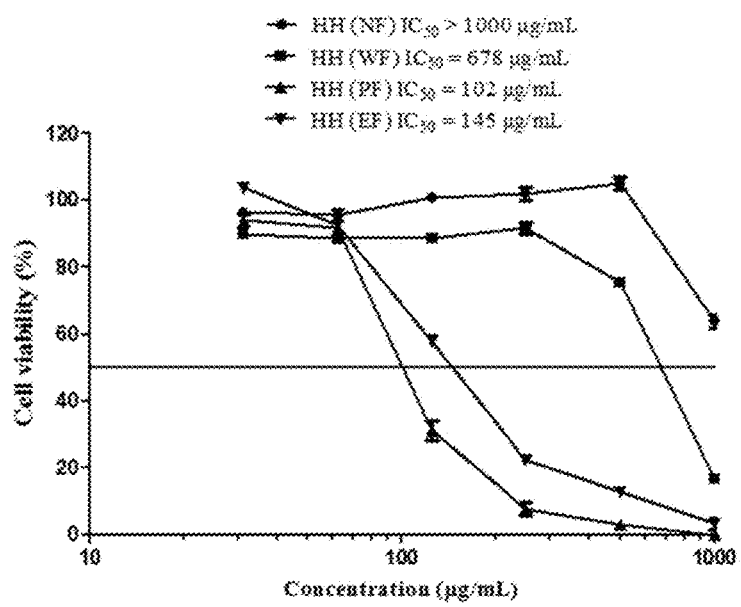
FIG. 1 shows the cell viability of HH-NF, HH-WF, HH-PF and HH-EF in PC-12 cells after 48 h of treatment. The cell viability was measured with an MTT assay.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise. The terms "optional" or "optionally" means that the described circumstance may or may not occur so that the invention includes instances where the circumstance occurs and instances where it does not occur.

The present invention provides a method for treating a subject suffering from a neurodegenerative disease.

The term "neurodegenerative disease" as used herein means a disease, disorder, or otherwise abnormal condition of the nervous system in which the nervous system deteriorates over time, thus impairing the subject from carrying out normal tasks such as impairing the motor tasks and/or mental functions, namely tasks relating to cognition and memory. A neurodegenerative disease is usually characterized by damage to the central nervous system and may be identified by neuronal death. Said diseases include, for example, Parkinson's disease, Huntington disease, Alzheimer's disease, multiple sclerosis or amyotrophic lateral sclerosis (ALS), HIV-associated Dementia or Pick's Disease and the like. The neurodegenerative disease is, in particular, a neurodegenerative disease which is in a progressive state in which symptoms worsen over time such as at a gradual rate.

The neurodegenerative disease is in particular associated with the aggregation of at least one specific protein in the neuronal cells and/or the formation of inclusion bodies. For example, Alzheimer's disease is primarily associated with aggregated amyloid-β and tau proteins, Parkinson's disease with aggregates comprising protein α-synuclein bound to ubiquitin and Huntington's disease with mutant huntingtin and inclusions.

The neurodegenerative disease of the present invention is in particular selected from Parkinson's disease or Huntington's disease. The term "Parkinson's disease" as used herein refers to a neurodegenerative disease of the brain that leads to tremor and difficulties with walking and with the coordination and occurs when dopaminergic neuronal cells are slowly destroyed. Lewy bodies containing fibrillary aggregates of α-synuclein such as mutant α-synuclein, which are abnormal aggregates of proteins that develop inside neuronal cells, were found in subjects with Parkinson's disease. Mutant α-synuclein is α-synuclein expressed from a gene having one or more point mutations such as A53T, A30P, E46K, H50Q or G51D, in particular A53T. The term "Huntington's disease" as used herein refers to a neurodegenerative disease which is a genetic disease and affects muscle coordination. It leads to cognitive and psychiatric problems and is assumed to be caused by an expanded CAG triplet repeat producing a mutant huntingtin protein, wherein nuclear inclusions occur as part of the disease process.

"Treating" the neurodegenerative disease in particular includes arresting the further progression, alleviating or reversing one or more symptoms of the neurodegenerative disease. In particular the term treating includes delaying the onset and/or preventing or delaying the progression of the neurodegenerative disease. The expression "effective amount" generally denotes an amount sufficient to produce therapeutically desirable results, wherein the exact nature of the result varies depending on the specific disorder which is treated. When the disorder is a neurodegenerative disease, the result is usually an arrest of the further progression, an alleviation or reversal of the symptom of the neurodegenerative disease. For instance, the effective amount of the triterpenoid of the present invention is an amount capable of inducing autophagy of respective cells in the subject, in particular an amount capable of significantly increasing the formation of the protein level of LC3-II as indicator of autophagic activity compared to an untreated control sample, of significantly inducing degradation of mutant huntingtin proteins and/or of significantly facilitating the degradation of mutant A53T α-synuclein which can be determined by means of Western blotting.

The term "subject" in particular refers to an animal or a human, in particular a mammal and most preferably a human. I.e. the subject is in most preferred embodiments a human having one of Parkinson's disease or Huntington's disease.

Said method of the present invention comprises a step of administering an effective amount of at least one triterpenoid to the subject. The triterpenoid of the present invention has a structure of Formula (I):

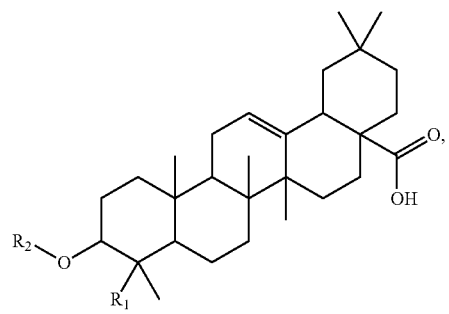

Formula (I)

in particular it has a structure of Formula (II):

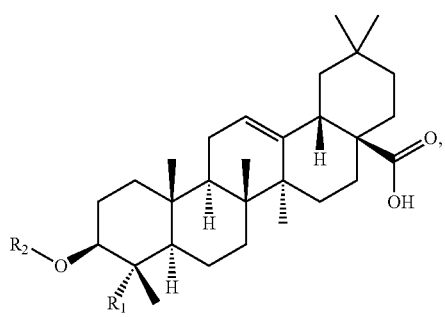

Formula (II)

$R_1$ is —$CH_3$ or —$CH_2OH$, preferably $R_1$ is —$CH_2OH$. $R_2$ is H or a glycoside moiety.

Triterpenoids are known as compounds which are present in various plants and derived from a type of terpene containing thirty carbon atoms. Basically, they can be regraded for being assembled from six $C_5$-isoprene units and can be distinguished based on the presence of oxygen containing functional groups, the number and position of double bonds and changes to the basic carbon skeleton. The triterpenoid of the present invention is a pentacyclic monodesmosidic triterpenoid saponin or triterpenoid sapogenin (also named triterpene saponins or triterpene sapogenins) of the oleanane type. Triterpenoid saponins are generally known as a subgroup of saponins consisting of triterpenoid aglycones designated "triterpenoid sapogenins", covalently linked to one or more glycoside moieties. Triterpenoids of the oleanane type are derived from the following oleanane-type basic structure:

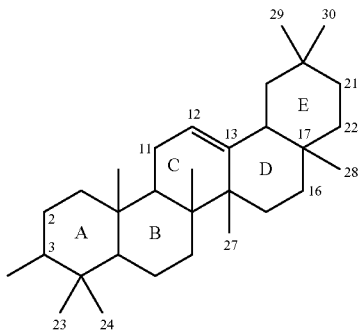

The triterpenoid of the present Invention also referred to as "low polarity triterpenoid" does not have an ester functional group formed at $C_{28}$ of the oleanane-type basic structure, i.e. has a different polarity compared to triterpenoids with an ester group there. Namely, in the triterpenoid of the present invention, $C_{28}$ forms a carboxylic acid group. The inventors unexpectedly found that such low polarity triterpenoids are especially suitable and advantageously effective in treating neurodegenerative diseases, in particular allows for an exceptional induction of autophagy compared to triterpenoids with ester function at $C_{28}$.

The term "glycoside moiety" used herein refers to a moiety formed by optionally substituted monosaccharides. The glycoside moiety can be a mono-, di- or oligosaccharide moiety, for example, formed by one or more of rhamnose, glucose and/or arabinose. A disaccharide moiety is in particular formed by two monosaccharides linked by glycosidic bond. An oligosaccharide moiety is in particular formed by three or more monosaccharides linked by glycosidic bond. The monosaccharides in the glycoside moiety may be present in different diasteromeric forms, in particular α or β anomers and D or L isomers. The term "glycosidic bond" is a type of chemical bond and covalent linkage formed between the anomeric hydroxyl group of a monosaccharide and the hydroxyl group of another monosaccharide.

The glycoside moiety which can form $R_2$ in particular comprises one or more of rhamnose, glucose and/or arabinose, further preferred one or more of rhamnose and/or arabinose. The glycoside moiety which can form $R_2$ is preferably a disaccharide, in particular it comprises α-L-rhamnose and α-L-arabinose linked by glycosidic bond and most preferably $R_2$ is selected from H or a glyosidic moiety which is α-L-Rha(1→2)α-L-Ara(1→)-, i.e.

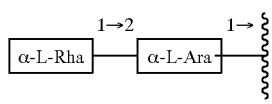

which can be expressed with Formula (III):

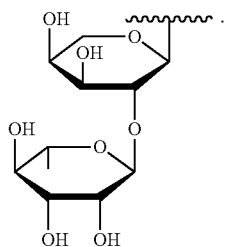

Formula (III)

Preferably, the at least one triterpenoid has a structure of Formula (IV):

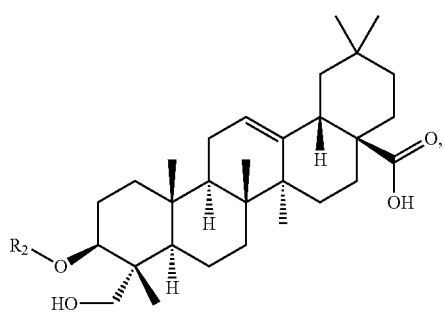

Formula (IV)

wherein $R_2$ is H or a glycoside moiety in particular formed by one or more of rhamnose, glucose and/or arabinose. Preferably, the glycoside moiety is α-L-Rha(1→2)α-L-Ara (1→)-, i.e.

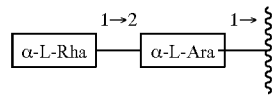

In further preferred embodiments, the at least one triterpenoid has a structure of Formula (V):

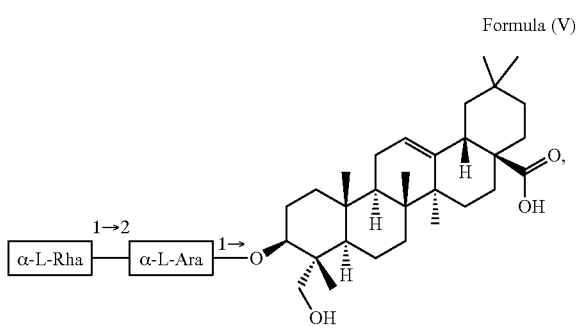

Formula (V)

i.e. $R_2$ in Formula (IV) is a glycoside moiety which is α-L-Rha(1→2)α-L-Ara(1→)-, namely the triterpenoid is a triterpenoid saponin also known as α-hederin, the at least one triterpenoid has a structure of Formula (VI):

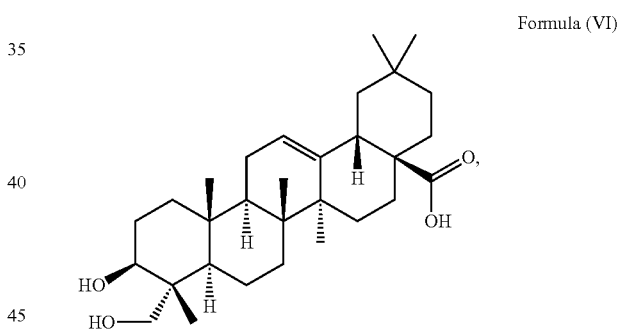

Formula (VI)

i.e. $R_2$ in Formula (IV) is H, namely the triterpenoid is a triterpenoid sapogenin also known as hederagenin. α-Hederin and hederagenin are commercially available and/or can be extracted from *Hedera helix* such as by an extraction further described below.

The expression "an effective amount of at least one triterpenoid" means that in embodiments an effective amount of one triterpenoid of Formula (I) is administered for treatment; wherein in other embodiments an effective amount of two or even more triterpenoids of Formula (I) is administered, wherein the amount of these two or more triterpenoids of Formula (I) form the effective amount for treatment of the neurodegenerative disease.

More specifically, in an embodiment of the present invention, one triterpenoid having a structure of Formula (I) is administered, i.e. the amount of said triterpenoid needs to be an effective amount for treatment of the neurodegenerative disease. In alternative embodiments of the present invention, at least a first and a second triterpenoid having a structure of Formula (I) which together form an effective amount for treatment of the neurodegenerative disease are administered.

In further embodiments of the present invention, three or more triterpenoids having a structure of Formula (I) are administered.

The effective amount of the at least one triterpenoid of the present invention may depend on the species, body weight, age and individual conditions of the subject and can be determined by standard procedures such as with cell cultures or experimental animals. A concentration of the at least one triterpenoid such as a triterpenoid of Formula (V) or (VI) may, for example, be at least 10 µM to, for example, about 100 µM. If the at least one triterpenoid is of Formula (V), the concentration may be about 12 µM to about 30 µM such as about 12 µM to about 24 µM. If the at least one triterpenoid is of Formula (VI), the concentration may be about 40 µM to about 100 µM such as about 40 µM to about 80 µM.

In embodiments of the present invention at least two triterpenoids falling under Formula (I) are administered with the first triterpenoid having a structure of Formula (V):

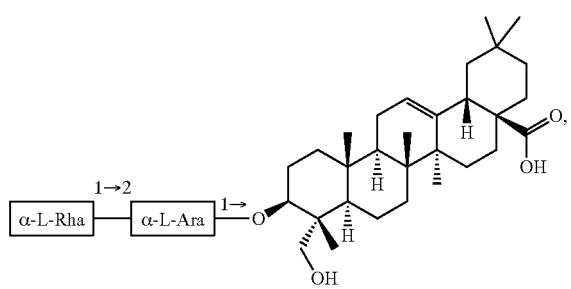

Formula (V)

i.e. being α-hederin and the second triterpenoid having a structure of Formula (VI):

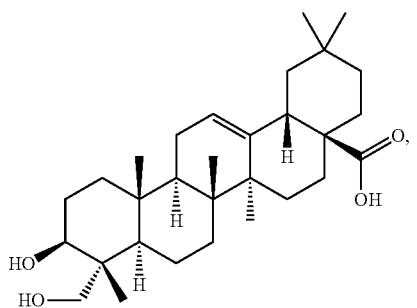

Formula (VI)

i.e. being hederagenin.

The triterpenoid may be administered by an oral or parenteral route to a subject, preferably a human.

Further components such as further triterpenoids which are not of Formula (I) or other components in particular from *Hedera helix* may be present, i.e. may be administered together with the at least one triterpenoid of Formula (I). For example, the effective amount of the at least one triterpenoid may be administered in form of a *Hedera helix* extract which might contain further triterpenoids which are or are not of Formula (I) or other ingredients in addition to the effective amount of the at least one triterpenoid of Formula (I) for treating the neurodegenerative disease. I.e. in an embodiment of the present invention, the at least one triterpenoid of Formula (I) is administered in form of a *Hedera helix* extract optionally with one or more excipients such as pharmaceutically tolerable excipients. The terms or expressions "*Hedera helix* extract" and "extracted from *Hedera helix*" mean that the at least one triterpenoid of Formula (I) is derived, namely derived by means of extraction including further processing and purification, from *Hedera helix* plant material. The term "extraction" will be understood by those skilled in the art as treating plant material with an extraction solvent to obtain desired components, in the present invention triterpenoids of Formula (I), including in particular separating them from unwanted plant material and/or other components present in the plant material. The *Hedera helix* extract can be in liquid form, in particular a decoction, solution, infusion or tincture or in solid form, in particular a powder or granules. Most preferably, the *Hedera helix* extract is in solid form such as a powder. I.e. in embodiments of the present invention, the at least one triterpenoid is administered in form of an extract obtained from *Hedera helix*.

*Hedera helix* L. (also named ivy) is of the genus *Hedera* of the family Araliaceae. It naturally growths in Europe and has been introduced to North America and Asia.

The triterpenoid may be administered in form of a pharmaceutical composition comprising the at least one triterpenoid optionally comprised in a *Hedera helix* extract and at least one pharmaceutically tolerable excipient such as one or more of a diluent, a filler, a binder, a disintegrant, a lubricant, a coloring agent, a surfactant and a preservative. The pharmaceutical composition can be present in solid, semisolid or liquid form. The pharmaceutical composition may comprise further pharmaceutical effective ingredients such as therapeutic compounds used for treating neurodegenerative diseases.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition according to the invention may be administered by an oral or parenteral route to a subject, preferably a human.

The at least one triterpenoid is in preferred embodiments of the present invention obtained or obtainable, in particular obtained, from *Hedera helix* by an extraction comprising steps of:

(i) subjecting *Hedera helix* plant material to a solvent extraction with an extraction solvent for obtaining a *Hedera helix* crude extract, wherein the extraction solvent comprises an aliphatic alcohol;

(ii) contacting the *Hedera helix* crude extract with a first and a second separation solvent for obtaining a first and a second layer and separating the first layer from the second layer, wherein the first separation solvent comprises water and the second separation solvent comprises at least one hydrocarbon, and wherein the first layer comprises the triterpenoid and the main part of the first separation solvent;

(iii) contacting the first layer after step (ii) with a third separation solvent comprising an ester for forming a third layer comprising the at least one triterpenoid and the main part of the third separation solvent and separating the third layer from the first layer;

(iv) isolating the triterpenoid from the third layer.

Preferably, the *Hedera helix* plant material comprises the whole plant, i.e. it comprises non-aerial parts such as roots and aerial parts of *Hedera helix*. The method of the present invention may further comprise steps before carrying out step (i) of a) drying the *Hedera helix* plant material, and/or b) cutting, shredding, milling and/or pulverizing the *Hedera helix* plant material.

In particular, the *Hedera helix* plant material is pulverized before step (i), i.e. the *Hedera helix* plant material is a powder. In particular embodiments of the present invention, the *Hedera helix* plant material is a powder comprising the whole plant.

The extraction solvent in step (i) comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the extracting solvent is a monohydric aliphatic alcohol, still more preferably a monohydric alcohol with 1 to 2 carbon atoms. More preferably, the aliphatic alcohol of the extraction solvent is ethanol. The extraction solvent most preferably comprises and in particular essentially consists of 75 Vol-% ethanol. The amount of *Hedera helix* plant material in relation to the total amount of the extraction solvent in step (i) is preferably between 10 mg/ml and 200 mg/ml *Hedera helix* plant material relative to the total amount of extraction solvent.

The solvent extraction in step (i) is preferably carried out for 0.5 to 10 h, in particular for about 3 h. The solvent extraction may be carried out several times, i.e. the extraction solvent is divided into several parts for successively extracting the same *Hedera helix* plant material.

Step (i) preferably further comprises separating the supernatant such as by filtration from the *Hedera helix* plant material for obtaining a supernatant and a residue and in particular at least partially removing the extraction solvent from the supernatant for forming the *Hedera helix* crude extract. The expression "at least partially removing" as used herein means that at least 50% by weight of the extraction solvent is removed, in particular at least 80% by weight and further preferred at least 90% by weight of the extraction solvent is removed based on the weight of the supernatant. "Completely removing the extraction solvent" means removing more than 95% by weight of the extraction solvent from the supernatant.

More preferably, step (i) comprises steps of:

a) contacting the *Hedera helix* plant material with a first portion of the extraction solvent at a temperature of about 20° C. to about 30° C., in particular immersing the *Hedera helix* plant material with a first portion of the extraction solvent for at least 30 min and in particular for about 1 h, and separating the supernatant for obtaining a first supernatant and a first residue such as by filtration;

b) contacting the first residue with a second part of the extraction solvent at a temperature above 30° C., in particular above 50° C. and more preferably above 60° C. and in particular at reflux for at least 30 min and in particular for about 1 h, and separating the supernatant for obtaining a second supernatant and a second residue such as by filtration;

c) contacting the second residue with a third part of the extraction solvent at a temperature above 30° C., in particular above 50° C. and more preferably above 60° C. and in particular at reflux for at least 30 min and in particular for about 1 h, and separating the supernatant for obtaining a third supernatant and a third residue such as by filtration;

and combining the first, the second and the third supernatant and at least partially removing the extraction solvent for forming the *Hedera helix* crude extract.

The second separation solvent in step (ii) comprises at least one hydrocarbon which is in particular a $C_5$ and/or $C_6$ hydrocarbon. Preferably, the hydrocarbon comprises and in particular essentially consists of a mixture of $C_5$ and/or $C_6$ hydrocarbons such as aliphatic hydrocarbons like pentane and hexane. The second separation solvent in particular comprises and more preferably essentially consists of petroleum ether.

Preferably, contacting the *Hedera helix* crude extract with the first separation solvent and the second separation solvent in step (ii) means sequentially adding the first separation solvent and the second separation solvent to the *Hedera helix* crude extract. In preferred embodiments of the present invention, the crude extract is added, preferably re-dissolved in the first separation solvent. Then the second separation solvent is preferably added accompanied by shaking for forming the first and the second layer and the first layer is then separated from the second layer. The first separation solvent is mainly comprised in the first layer and the second separation solvent is mainly comprised in the second layer. More specifically, the first layer after step (ii) comprises the at least one triterpenoid and the main part of the first separation solvent. The first layer after step (ii) can comprise a triterpenoid derivate as further explained below. The second layer comprises the main part of the second separation solvent. "Main part" in contrast to "minor part" in particular means more than 80% by weight such as more than 90% by weight of the total amount of the separation solvent initially added before forming the two layers, preferably more than 95% by weight. The term "layers" used herein and as generally understood by a person of skill in the art means separated phases resulting from contacting at least two solvents which are substantially immiscible or immiscible with each other, such as first and the second separation solvent. After forming a layer by contacting substantially immiscible or immiscible solvents, the term "layer" is still used herein for further processed products from said layer such as after removal of the solvent portion.

Preferably, the volume ratio of first separation solvent to the second separation solvent is about 1:1. Step (ii) may be repeated for several times, i.e. the second separation solvent is divided into at least two parts and the first layer is preferably contacted with a second and subsequently optionally with further parts of the second separation solvent. More preferably, step (ii) is repeated two times, i.e. a second part of the second separation solvent is added to the first layer accompanied by shaking, the first layer is separated and then a third part of the second separation solvent is added to the first layer accompanied by shaking.

The third separation solvent used in step (iii) comprises an ester. The ester is in particular a $C_1$-$C_6$ aliphatic alcohol ester of a $C_1$-$C_7$ alkyl carboxylic acid. Further preferably, the ester is a $C_3$-$C_7$ ester, in particular ethyl acetate or ethyl formate. In most preferred embodiments of the present invention, the third separation solvent comprises and preferably essentially consists of ethyl acetate. The third separation solvent is added to the first layer after step (ii) preferably accompanied by shaking for forming the third layer. The third layer after step (iii) comprises the at least one triterpenoid and the main part of the third separation solvent. The first layer after step (iii) can comprise a triterpenoid derivate as further explained below.

Preferably, the volume ratio of the second separation solvent to the first layer is about 1:1. Step (iii) may be repeated for several times, i.e. by subsequently adding parts of the third separation solvent to the first layer, and the resulting third layers are combined, i.e. the first layer is preferably contacted with at least two parts of the third separation solvent and the resulting third layers are combined. More preferably, step (iii) is repeated two times, i.e. after carrying out step (iii), a second part of the third separation solvent is added to the first layer accompanied by shaking, the third layer is separated and then a third part of the third separation solvent is added to the first layer accompanied by shaking and the resulting third layer is separated. The third layers obtained are then combined.

Step (iv) preferably comprises at least partially removing the solvent portion of the third layer and/or subjecting the third layer to a chromatographic separation, in particular at least partially removing the solvent portion of the third layer and subsequently subjecting the third layer to a chromatographic separation including fractionating the third layer. Step (iv) can be carried out such that the at least one triterpenoid is obtained in isolated form, i.e. without significant amounts of further triterpenoids and/or other components from *Hedera helix*, i.e. essentially consisting of the at least one triterpenoid. Alternatively, isolating the at least one triterpenoid can be carried out such that a *Hedera helix* extract rich in the at least one triterpenoid is obtained which additionally contains further triterpenoids such as further triterpenoids of Formula (I) and/or other components from *Hedera helix*. The expression "rich in the at least one triterpenoid" preferably means an amount of the at least one triterpenoid of at least 2 µM, in particular of at least 15 µM and further preferred of at least 20 µM in 250 µg/ml of the *Hedera helix* extract.

The solvent portion of the third layer in particular comprises the third separation solvent and optionally minor parts of the first and second separation solvent. For at least partially removing the solvent portion of the third layer, in particular for completely removing the solvent portion of the third layer, the third layer is preferably subjected to a temperature above 40° C., in particular above 50° C. and preferably above 60° C. in particular under vacuum such as by rotary evaporation. The chromatographic separation step in particular comprises liquid chromatography including column chromatography such as high-performance liquid chromatography (HPLC) which is a known column chromatography usually carried out with operational pressures up to 5 MPa or higher or ultra-high performance liquid chromatography (UHPLC). The skilled person is aware of said terms and to how carry out such subtypes of chromatography.

HPLC or UHPLC is in particular carried out with a reverse stationary phase having alkyl chains covalently bound to a solid support in particular comprising octadecyl-chains referred to as "C18 phase", i.e. the stationary phase is in particular a C18 phase. For example, Agilent Zorbax Eclipse Plus C-18 can be used with a particle size of 1.8 µm for example with a flow rate of 0.35 ml/min.

The mobile phase in particular includes and most preferably essentially consists of a carboxylic acid in water and/or a carboxylic acid in a nitrile. In particular, a gradient of a first eluting solvent and a second eluting solvent is applied, the first eluting solvent comprising and in particular essentially consisting of a carboxylic acid in water. The second eluting solvent comprises and in particular essentially consists of a carboxylic acid in a nitrile. The carboxylic acid is in particular based on a hydrocarbon such as a branched or straight chain alkane with a carboxyl group. Preferably, the carboxylic acid is based on a straight chain alkane with 1 to 2 carbon atoms. More preferably, the carboxylic acid in the first eluting solvent and the second eluting solvent is formic acid. The nitrile is preferably based on a hydrocarbon such as a branched or straight chain alkane with a nitrile group, in particular the nitrile is based on a straight chain alkane with 1 to 2 carbon atoms. The nitrile is most preferably acetonitrile. The gradient applied is preferably according to table 1, wherein the first eluting solvent essentially consists of formic acid in water and the second eluting solvent essentially consists of formic acid in acetonitrile.

TABLE 1 preferred gradient of the first eluting solvent and the second eluting solvent

| | |
|---|---|
| 0-8 min | 5-70% second eluting solvent |
| 8-11 min | 70-100% second eluting solvent |
| 11-14 min | 100% second eluting solvent |
| 14.1-18 min | 5% second eluting solvent |

Preferred triterpenoids are eluted between about 6.5 min to about 9.5 min.

"Fractionating" in particular means separating the optionally dried third layer by means of chromatographic separation into fractions such as accompanied by thin-layer chromatography (TLC) monitoring which is usual practice in the art, i.e. the number and size of each fraction is determined by the specific composition and changes in the composition. I.e. a change in the composition confirmed with TLC means next fraction. The fraction with the triterpenoid may be confirmed with a respective standard. Additionally or alternatively, the fraction with the triterpenoid can be confirmed by means of mass spectrometry with a respective standard. For example, UHPLC may be applied for the chromatographic separation equipped with a time of flight MS (UHPLC-TOF-MS) with a jet stream ion source operated in a negative ion mode.

The extraction may comprise further steps for further increasing the yield of the at least one triterpenoid of:

(v) contacting the first layer after step (iii) with a fourth separation solvent comprising an aliphatic alcohol for forming a fourth layer comprising a triterpenoid derivate and the main part of the fourth separation solvent and separating the fourth layer from the first layer;

(vi) subjecting the fourth layer to acid hydrolysis by contacting it with water and a protic acid for converting the triterpenoid derivate to the triterpenoid;

(vii) contacting the mixture after step (vi) with a fifth separation solvent for obtaining a fifth layer and separating the fifth layer, wherein the fifth separation solvent comprises an ester, and wherein the fifth layer comprises the triterpenoid and the main part of the fifth separation solvent;

(viii) isolating the triterpenoid from the fifth layer.

The fourth separation solvent comprises an aliphatic alcohol. Preferably, the aliphatic alcohol is a monohydric aliphatic alcohol, still more preferably a monohydric alcohol with 4 carbon atoms. I.e. the aliphatic alcohol of the fourth separation solvent is more preferably n-butanol. The fourth separation solvent in particular comprises and most preferably essentially consists of n-butanol. The fourth separation solvent is added to the first layer after step (iii) preferably accompanied by shaking for forming the third layer. Preferably, the volume ratio of fourth separation solvent to the first layer is about 1:1. Step (v) may be repeated for several times and the resulting fourth layers are combined, i.e. the first layer is preferably successively contacted with further parts of the fourth separation solvent and the resulting fourth layers are combined. More preferably, step (v) is repeated two times, i.e. after carrying out step (v), a second part of the fourth separation solvent is added to the first layer accompanied by shaking, the fourth layer is separated and then a third part of the fourth separation solvent is added to the first layer accompanied by shaking and the resulting fourth layer is separated. The fourth layers obtained are then combined.

Preferably, the solvent portion of the fourth layer is at least partially removed before carrying out step (vi). The solvent portion of the fourth layer in particular comprises the fourth separation solvent and optionally minor parts of the first, second and third separation solvent. For at least partially removing the solvent portion of the fourth layer, in particular for completely removing the solvent portion of the fourth layer, the fourth layer is preferably subjected to a temperature above 40° C., in particular above 50° C. and preferably above 60° C. in particular under vacuum such as by rotary evaporation.

The term "triterpenoid derivate" as used herein means a derivate of the at least one triterpenoid which derivate can be converted to the triterpenoid of Formula (I) by acid hydrolysis, in particular an ester of the triterpenoid, i.e. of Formula (VII)

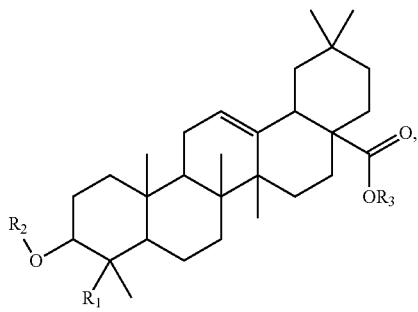

Formula (VII)

such as of Formula (VIII):

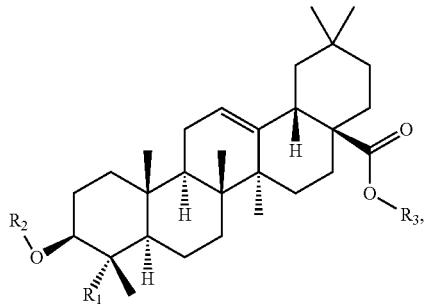

Formula (VIII)

with $R_1$ and $R_2$ as defined above and $R_3$ being a glycoside moiety.

Acid hydrolysis is generally known as a process in which a protic acid is used to catalyze the cleavage of a chemical bond via a nucleophilic substitution reaction. The acid hydrolysis in step (vi) is preferably carried out with a protic acid comprising and in particular essentially consisting of hydrochloric acid. Preferably, the fourth layer after step (v) is re-dissolved in water and the protic acid, in particular hydrochloric acid, is added such that a pH below 3 and in particular a pH of about 2.5 is obtained. The mixture is preferably heated for at least 1 h, in particular for about 2 h, to at least 80° C., more preferably to about 100° C. The mixture is preferably allowed to cool down to a temperature of about 20° C. to about 30° C. before carrying out step (vii).

The fifth separation solvent used in step (vii) comprises an ester. The ester is in particular a $C_3$-$C_7$ ester, in particular ethyl acetate or ethyl formate. In most preferred embodiments of the present invention, the fifth separation solvent comprises and preferably essentially consists of ethyl acetate. The fifth separation solvent is added to the mixture after step (vi) preferably accompanied by shaking for forming the fifth layer. Preferably, the volume ratio of the fifth separation solvent to the mixture after step (vi) is about 1:1. Step (vii) may be repeated for several times and the resulting fifth layers are combined, i.e. the mixture after step (vi) is preferably contacted with further parts of the fifth separation solvent and the resulting fifth layers are combined. More preferably, step (vii) is repeated two times with the mixture, i.e. after carrying out step (vii), a second part of the fifth separation solvent is added to the mixture, i.e. after separating the fifth layer, accompanied by shaking, the formed fifth layer is separated and then a third part of the fifth separation solvent is added to the mixture accompanied by shaking and the resulting fifth layer is separated. The fifth layers obtained are then combined.

Isolation of the triterpenoid in step (viii) preferably comprises at least partially removing the solvent portion of the fifth layer and/or subjecting the fifth layer to a chromatographic separation, in particular at least partially removing the solvent portion of the fifth layer and subsequently subjecting the fifth layer to a chromatographic separation including fractionating the fifth layer as described above. The solvent portion of the fifth layer comprises the fifth separation solvent and can comprise minor parts of water and/or protic acid.

In an alternative embodiment of the present invention, the at least one triterpenoid is obtained from *Hedera helix* by an extraction comprising steps of:

(i) subjecting *Hedera helix* plant material to a solvent extraction with an extraction solvent for obtaining a *Hedera helix* crude extract, wherein the extraction solvent comprises an aliphatic alcohol;

(ii) contacting the *Hedera helix* crude extract with a first and a second separation solvent for obtaining a first and a second layer and separating the first layer from the second layer, wherein the first separation solvent comprises water and the second separation solvent comprises at least one hydrocarbon, and wherein the first layer comprises a triterpenoid derivate and the main part of the first separation solvent;

(iii) contacting the first layer after step (ii) with a third separation solvent comprising an ester for forming a third layer comprising the main part of the third separation solvent and separating the third layer from the first layer, wherein the first layer comprises the triterpenoid derivate;

(iv) contacting the first layer after step (iii) with a fourth separation solvent comprising an aliphatic alcohol for forming a fourth layer comprising the triterpenoid derivate and the main part of the fourth separation solvent and separating the fourth layer from the first layer;

(v) subjecting the fourth layer to acid hydrolysis by contacting it with water and a protic acid for converting the triterpenoid derivate to the triterpenoid;

(vi) contacting the mixture after step (v) with a fifth separation solvent for obtaining a fifth layer and separating the fifth layer, wherein the fifth separation solvent comprises water and the fifth separation solvent comprises an ester, and wherein the fifth layer comprises the triterpenoid and the main part of the fifth separation solvent;

(vii) isolating the triterpenoid from the fifth layer.

The steps are carried out as described above and preferably include the preferred features and steps described there. Steps (iv) to (vii) correspond to steps (v) to (viii) described above.

The present invention in a second aspect provides a method for extracting at least one triterpenoid having a structure of Formula (I):

Formula (I)

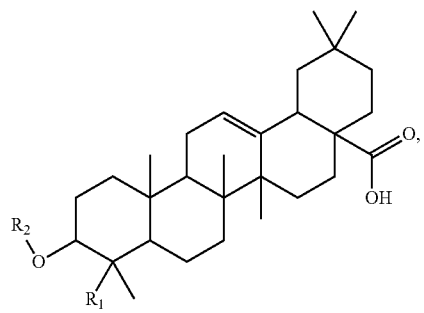

in particular of Formula (II):

Formula (II)

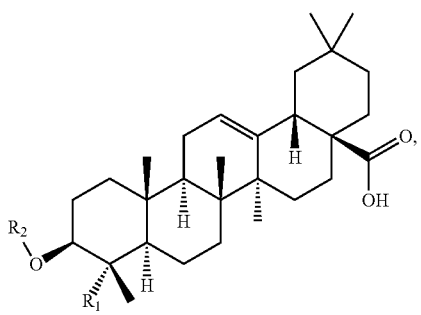

from *Hedera helix*, wherein $R_1$ is —$CH_3$ or —$CH_2OH$ and $R_2$ is H or a glycoside moiety. The method comprises the steps as described above and in particular embodiments the features and steps described as preferred ones above.

Further in accordance with the present invention is a *Hedera helix* extract obtained or obtainable by the method described above from *Hedera helix* plant material and comprising the at least one triterpenoid. The present invention also provides a method for treating a subject suffering from a neurodegenerative disease comprising the step of administering an effective amount of a *Hedera helix* extract comprising at least one triterpenoid having a structure of Formula (I), in particular comprising an effective amount of the at least one triterpenoid of Formula (I):

Formula (I)

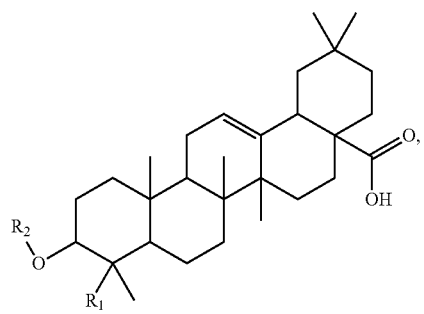

to the subject. The at least one triterpenoid is in particular of Formula (II):

Formula (II)

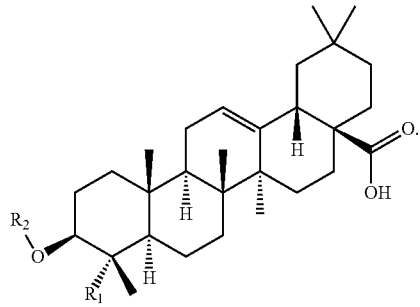

The triterpenoid preferably has a structure of Formula (IV):

Formula (IV)

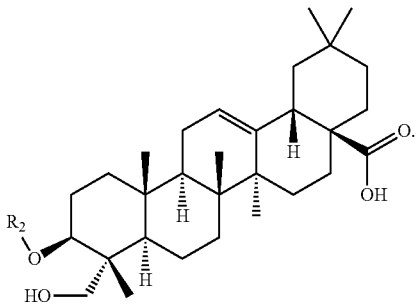

wherein $R_2$ is H or a glycoside moiety formed by one or more of rhamnose, glucose and/or arabinose. Preferably, the glycoside moiety is α-L-Rha(1→2)α-L-Ara(1→)-, i.e.

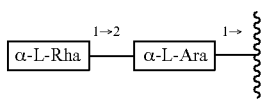

Further preferred, the triterpenoid has a structure of Formula (V):

Formula (V)

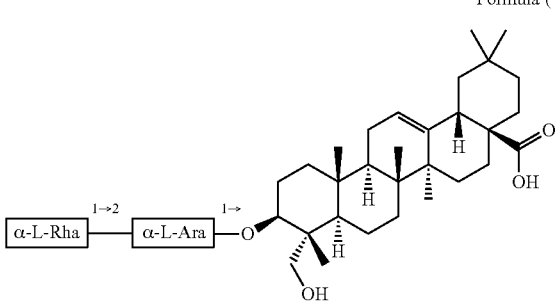

i.e. is α-hederin or a structure of Formula (VI):

Formula (VI)

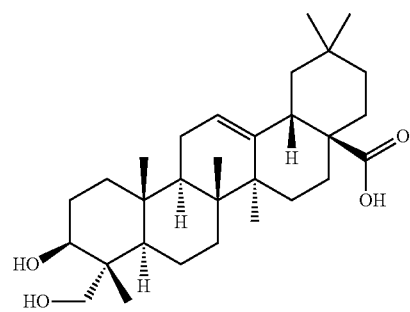

i.e. is hederagenin.

In particular, the *Hedera helix* extract comprises an effective amount of at least a first and a second triterpenoid which first triterpenoid has a structure of Formula (V) and which second triterpenoid has a structure of Formula (VI).

In another aspect, the present invention provides a method for inducing autophagy in neuronal cells from a subject suffering from a neurodegenerative disease comprising contacting the cells with an effective amount of at least one triterpenoid, wherein the triterpenoid has a structure of Formula (I):

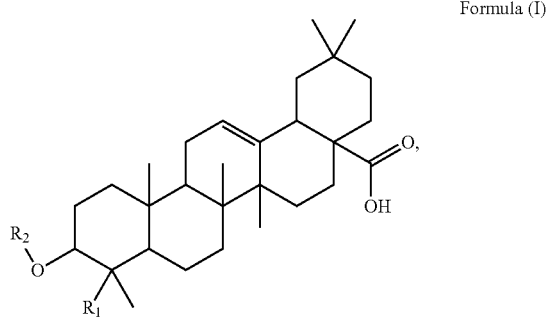

Formula (I)

in particular of Formula (II):

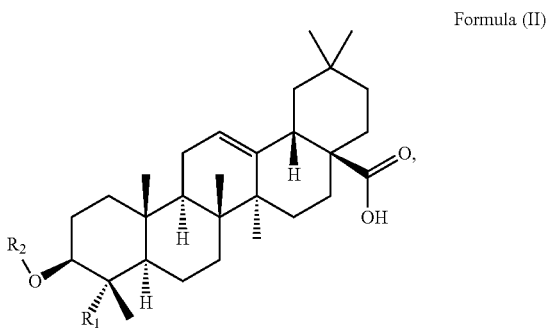

Formula (II)

wherein $R_1$ is —$CH_3$ or —$CH_2OH$ and $R_2$ is H or a glycoside moiety.

"Inducing autophagy" preferably means a significant increase in the protein level of LC3-III which is an indicator of autophagy and can be determined by means of Western blotting and/or a significant increase in autophagosomes and autolysosomes which can be determined using fluorescence microscopy techniques. In particular, inducing autophagy means an increase in the protein level of LC3-II of at least 25%, more preferably at least 50% and in particular more than 100% compared to the protein level in an untreated control with cells of the same cell and tissue type.

The cells are in particular neuronal cells such as from a mammal, for example a human, with a neurodegenerative disease such as Parkinson's disease or Huntington's disease.

Autophagy is in particular induced through the activation of the AMPK-mTOR signaling pathway (AMPK=AMP activated protein kinase, mTOR=mammalian target of rapamycin). In particular, the at least one triterpenoid reduces the protein level of mutant huntingtin, reduces the protein level of A53T α-synuclein, inhibits the oligomerization of α-synuclein and/or inhibits the inclusion formation of huntingtin via the AMPK-mTOR dependent autophagy inducing pathway. This can be confirmed by means of Western blotting, for example by determining the amount of phosphorylated AMPK or Ribosomal protein S6 kinase beta-1 (p70S6K), wherein an increased phosphorylation of AMPK and a reduced phosphorylation of p70S6K indicates activation of the AMPK-mTOR dependent autophagy inducing pathway. Autophagy is generally promoted by AMPK as key energy sensor and regulator of cellular metabolism. Conversely, autophagy is inhibited by the mammalian target of rapamycin (mTOR), a central cell-growth regulator, with p70S6K being a downstream target to mTOR.

The step of contacting the cells with the at least one triterpenoid of the present invention, in particular comprising a structure of Formula (V) or (VI), may be carried out by applying an incubation solution comprising the triterpenoid to said cells such as from a cell or tissue sample which incubation solution may further comprise suitable excipients such as buffers or a suitable growth medium. Alternatively, contacting the cells with the at least one triterpenoid may be carried out by administering the at least one triterpenoid to a subject comprising said cells, i.e. a subject suffering from a neurodegenerative disease such as Parkinson's disease or Huntington's disease. The triterpenoid may be administered by an oral or parenteral route to a subject, preferably a human. The at least one triterpenoid may be administered in form of a pharmaceutical composition comprising the at least one triterpenoid and at least one pharmaceutically tolerable excipient such as one or more of a diluent, a filler, a binder, a disintegrant, a lubricant, a coloring agent, a surfactant and a preservative. The pharmaceutical composition can be present in solid, semisolid or liquid form.

The amount of the at least one triterpenoid for contacting the cells may be between about 6 μM and 200 μM, in particular between 12 μM and 100 μM depending on the triterpenoid. Preferably, the cells are contacted with the triterpenoid for at least 4 h, further preferred for at least 8 h, in particular for at least 16 h and further preferred for at least 24 h. The $IC_{50}$ of the at least one triterpenoid against the cells may be at least 20 μM or at least 100 μM or even higher.

The triterpenoid for contacting the cells preferably has a structure of Formula (IV):

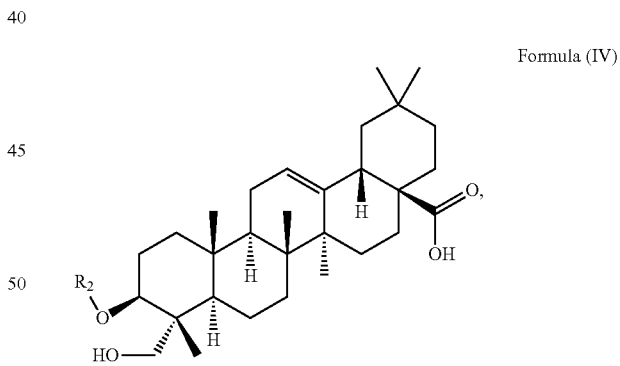

Formula (IV)

wherein $R_2$ is H or a glycoside moiety formed by one or more of rhamnose, glucose and/or arabinose, in particular rhamnose and arabinose, further preferred the glycoside moiety is α-L-Rha(1→2)α-L-Ara(1→)-, i.e.

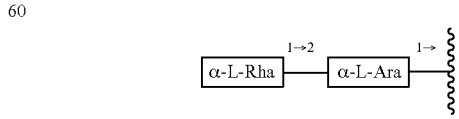

Further preferred, the triterpenoid for contacting the cells has a structure of Formula (V):

Formula (V)

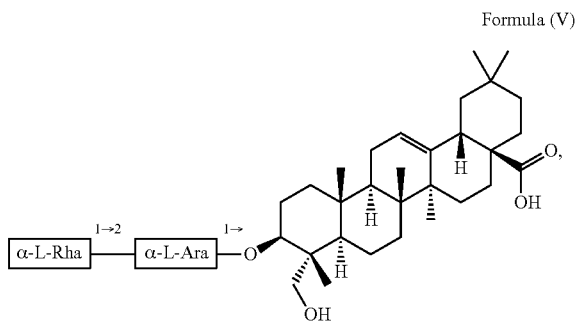

i.e. $R_2$ is α-L-Rha(1→2)α-L-Ara(1→)-, namely the triterpenoid is α-hederin or a structure of Formula (VI):

Formula (VI)

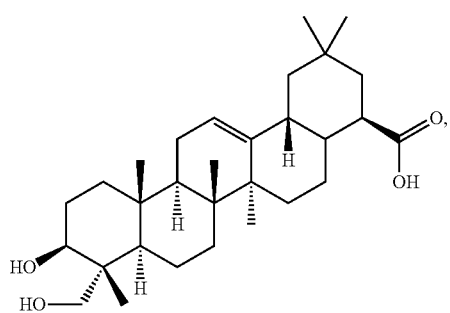

i.e. $R_2$ is H, namely the triterpenoid is hederagenin.

In particular, the method comprises contacting the cells with at least a first and a second triterpenoid from *Hedera helix* which first triterpenoid has a structure of Formula (V) and which second triterpenoid has a structure of Formula (VI).

Further preferred, the triterpenoid for contacting the cells has a structure of Formula (V):

Formula (V)

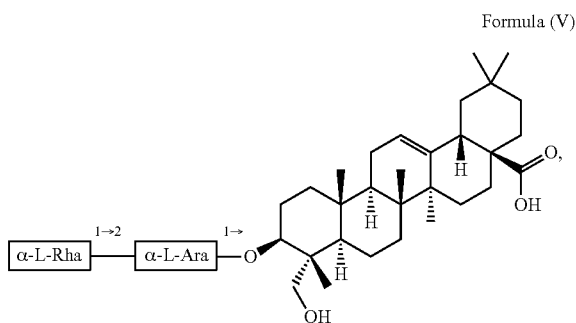

and the cells are contacted with said triterpenoid in a concentration of about 12 µM to about 30 µM. Preferably, the cells are contacted with the triterpenoid in a concentration of about 12 µM to about 24 µM, more preferably in a concentration of about 24 µM, preferably for at least 8 h, in particular for at least 16 h and further preferred for at least 24 h.

In alternative embodiments of the present invention, the triterpenoid for contacting the cells has a structure of Formula (VI):

Formula (VI)

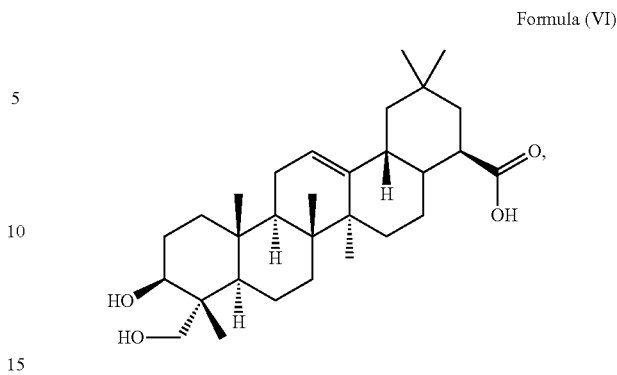

and the cells are contacted with said triterpenoid in a concentration of about 40 µM to about 100 µM.

Preferably, the cells are contacted with the triterpenoid in a concentration of about 40 µM to about 80 µM, more preferably in a concentration of about 80 µM, preferably for at least 4 h, in particular for at least 8 h and further preferred for at least 16 h.

According to the invention is also the at least one triterpenoid described above, in particular of Formula (V) or (VI), for use as a medicament for the treatment of a neurodegenerative disease, in particular Parkinson's disease or Huntington's disease. Another aspect of the present invention refers to the use of the triterpenoid described above, in particular of Formula (V) or (VI), for preparing a medicament for treatment of a neurodegenerative disease, in particular Parkinson's disease or Huntington's disease. The present invention also relates to the use of the triterpenoid described above, in particular of Formula (V) or (VI), as neuroprotective compounds for inducing autophagy, in particular for reducing the protein level of mutant huntingtin, reducing the protein level of A53T α-synuclein, inhibiting the oligomerization of α-synuclein and/or inhibiting the inclusion formation of huntingtin via the AMPK-mTOR dependent autophagy inducing pathway.

EXAMPLES

Preparation of *Hedera Helix* Extracts (HH)

The whole *Hedera helix* plant was smashed into a fine power and extracted with 75% ethanol as extraction solvent. 500 g of *Hedera helix* plant material in form of a powder was first immersed in 5 L of 75% ethanol for 1 h, and then refluxed twice with 75% ethanol for 1 h, respectively. The supernatants were combined and dried by rotary evaporation at 60° C. under vacuum condition. The crude *Hedera helix* extract was re-dissolved in water and then partitioned with petroleum ether as second separation solvent (1:1 vol/vol) for 3 times to obtain petroleum ether layers which give an *Hedera helix* extract abbreviated as "HH-PF", then the water layer was partitioned with ethyl ethanoate as third separation solvent (1:1 vol/vol) for 3 times. All the ethyl ethanoate layers (referred to as the *Hedera helix* extract "HH-EF") were combined and dried. The remaining water layer was then further partitioned with n-butanol as fourth separation solvent (1:1 vol/vol) for 3 times and dried to give *Hedera helix* extracts referred to as "HH-NF" and from the first layer "HH-WF", respectively. HH-WF, HH-NF, HH-EF, HH-PF were further analyzed by means of UHPLC-TOF-MS and for their biological activity.

For the acid hydrolysis of HH-NF, 20 g HH-NF was re-dissolved in 200 mL of water, then hydrochloric acid as protic acid was added into the HH-NF solution until pH=2.5. This acid solution was heated for 2 hours at 100° C. After cooling it down, the acid solution was partitioned with ethyl ethanoate as fifth separation solvent (1:1 vol/vol) for 3 times to give *Hedera helix* extracts referred to as "HH-NF(AHS)-WF" from the aqueous layer and "HH-NF(AHS)-EF" (AHS=acid-hydrolyzed solution), which were dried for further UHPLC-TOF-MS and biological activity analysis.

Example 1

Autophagic Activity Analysis of *Hedera Helix* Extracts (HH)

Materials and Methods

The identification of the bioactive components in HH-EF and HH-NF(AHS)-EF: The identification of the bioactive components in HH-EF and HH-NF(AHS)-EF were performed by using CMC (Wu, A. G. et al., Sci Rep 2015, 5:17199). The measurement of the bioactive components, hederagenin and α-hederin in HH-EF, HH-NF and HH-NF (AHS)-EF were carried out by UHPLC (Agilent Technologies 1290 Series) equipped with the time of flight MS (Agilent Technologies 6230) with a jet stream ion source, which was operated in negative ion mode during the analysis. All the samples were separated and analyzed on an Agilent Zorbax Eclipse Plus C-18 column with a particle size of 1.8 μm (flow rate: 0.35 mL/min). The mobile phase was set as follow: mobile phase A (0.1% formic acid in water) and mobile phase B (0.1% formic acid in acetonitrile (CAN)): 0-8 min, 5-70% B; 8-11 min, 70-100% B; 11-14 min, 100% B; 14.1-18 min, 5% B. For UHPLC-TOF-MS analysis, the data were acquired in the scan mode (m/z 100 to 1600 Da with 2.0 spectra/s). Data were analyzed by using Agilent MassHunter Workstation software B.01.03.

Immunocytochemistry and fluorescence microscopy: GFP-LC3 autophagic puncta formation was analyzed as described previously in (Wu, A. G. et al. Int J Mol Sci 2013, 14:22618-22641). Firstly, cells were plated on top of coverslips inside a 6-well culture dish. After compound treatment, cells were fixed with 4% paraformaldehyde for 20 min. FluorSave™ mounting media (Calbiochem, San Diego, Calif., USA) was used to mount the coverslips with cells before subjected to fluorescence microscopic analysis. The number of GFP-positive cells, and cells with GFP-LC3 puncta formation were examined and counted under the Nikon ECLIPSE 80i microscope by using 40× of magnification. In order to standardize the quantitation, the percentage of cells with autophagy induction was defined by counting the number of cells with increased punctate GFP-LC3 fluorescence in GFP-positive cells. A minimum of 1000 GFP-positive cells from 3 randomly selected fields were scored.

Cytotoxicity Assays: Cell viability was measured by using the MTT method (3-[4,5-dimethylthiazol-2-yl]-2,5-diphenyl tetrazolium bromide) as described previously (Wu, A. G. et al. Int J Mol Sci 2013, 14:22618-22641). Absorbance (OD) of cell samples was obtained by spectrophotometer at 570 nm. The percentage of cell viability was calculated by using the formula: cell viability (%)=cells number$_{treated}$/cells number$_{DMSO}$ control×100. All MTT data were calculated from three independent experiments.

Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Results

Figure 2A:
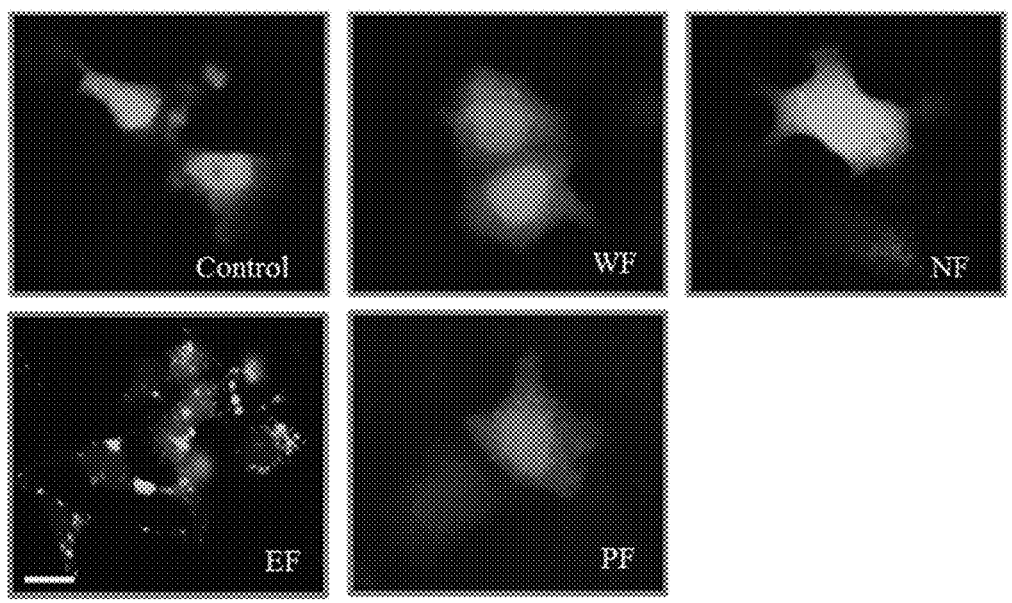
FIGS. 2A and 2B show the autophagic effect of *Hedera helix* extracts in green fluorescent protein (GFP)-LC3 transfected PC-12 cells.
Figure 2B:
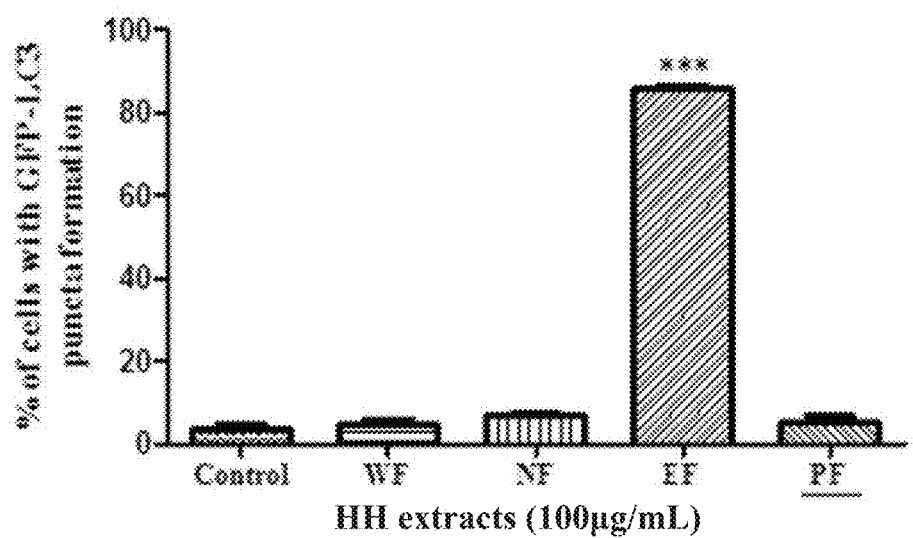
Figure 3A:
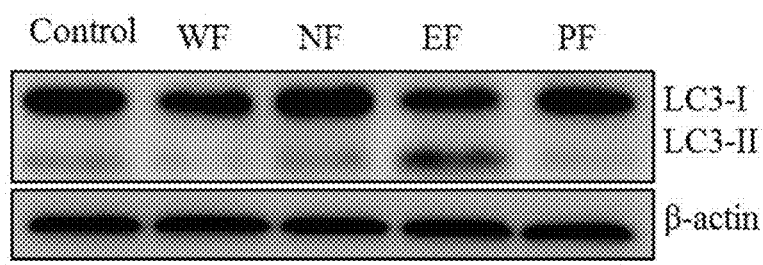
FIGS. 3A and 3B show the effect of *Hedera helix* on the conversion of LC3-I in PC-12 cells based on Western blotting analysis. The cells were treated with HH-WF, HH-NF, HH-EF, or HH-PF.
Figure 3B:
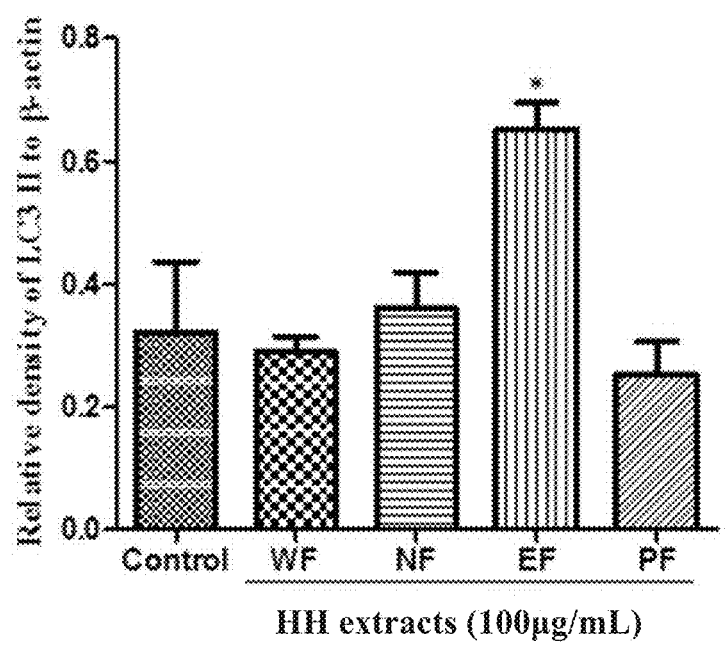

The $IC_{50}$ value of all extracts was evaluated using MTT assay (FIG. 1). Pheochromocytoma-derived PC-12 cells have been commonly adopted for the cellular study of neurotrophic action, protein trafficking or neural differentiation (Acta Physiol (Oxf) (Westerink, R. H. S, Ewing, A. G., Acta Physiol 2008, 192:273-285, Martin, T. F., Grishanin, R. N., Methods Cell Biol 2003, 71:267-286). PC-12 cells have also been used for the study of dopaminergic neurons and Parkinson's disease (PD) as they display metabolic features of PD (Maioli, M. et al., Sci Rep 2015, 5:10439). The autophagic effect of all *Hedera helix* extracts have been evaluated in green fluorescent protein (GFP)-LC3 transfected PC-12 cells (Wu, A. G. et al., Sci Rep 2015, 5:17199). During autophagy induction, LC3-I is activated by ATG genes, followed by the conjugation of LC3-I to phosphatidylethanolamine (PE), then cytosolic LC3-I become membrane-bound LC3-II for the formation of autophagosomes (Mehrpour, M. et al., Cell Res 2010, 20:748-762). Through observing the conversion of LC3 by immunofluorescence microscopy, FIGS. 2A and 2B confirm that HH-EF increases the formation of fluorescent autophagic puncta in PC-12 cells. This result was further confirmed by Western blot analysis (FIGS. 3A and 3B) which shows an increase in the protein level of LC3-II in PC-12 cells.

Example 2

Induction of Autophagy by Low Polarity Triterpenoids of the Present Invention

Materials and Methods

Cytotoxicity Assays: Cell viability was measured by using the MTT method (3-[4,5-dimethylthiazol-2-yl]-2,5-diphenyl tetrazolium bromide) as described previously (Wu, A. G. et al. Int J Mol Sci 2013, 14:22618-22641). Absorbance (OD) of cell samples was obtained by spectrophotometer at 570 nm. The percentage of cell viability was calculated by using the formula: cell viability (%)=cells number$_{treated}$/cells number$_{DMSO}$ control×100. All MTT data were calculated from three independent experiments. Cell viability was also measured by flow cytometry using the Annexin V staining kit (BD Biosciences, San Jose, Calif., USA).

Immunocytochemistry and fluorescence microscopy: GFP-LC3 puncta formation was analyzed as described previously (Wu, A. G. et al. Int J Mol Sci 2013, 14:22618-22641). Firstly, cells were plated on top of coverslips inside a 6-well culture dish. After compounds treatments, cells were fixed with 4% paraformaldehyde for 20 min. Fluor-Save™ mounting media (Calbiochem, San Diego, Calif., USA) was used to mount the coverslips with cells before subjected to fluorescence microscopic analysis. The number of GFP-positive cells, and cells with GFP-LC3 puncta formation was examined and counted under the Nikon ECLIPSE 80i microscope by using 40× of magnification. In order to standardize the quantitation, the percentage of cells with autophagy induction was defined by counting the number of cells with punctate GFP-LC3 fluorescence in GFP-positive cells. A minimum of 1000 GFP-positive cells from 3 randomly selected fields were scored.

Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Results

Figure 4:
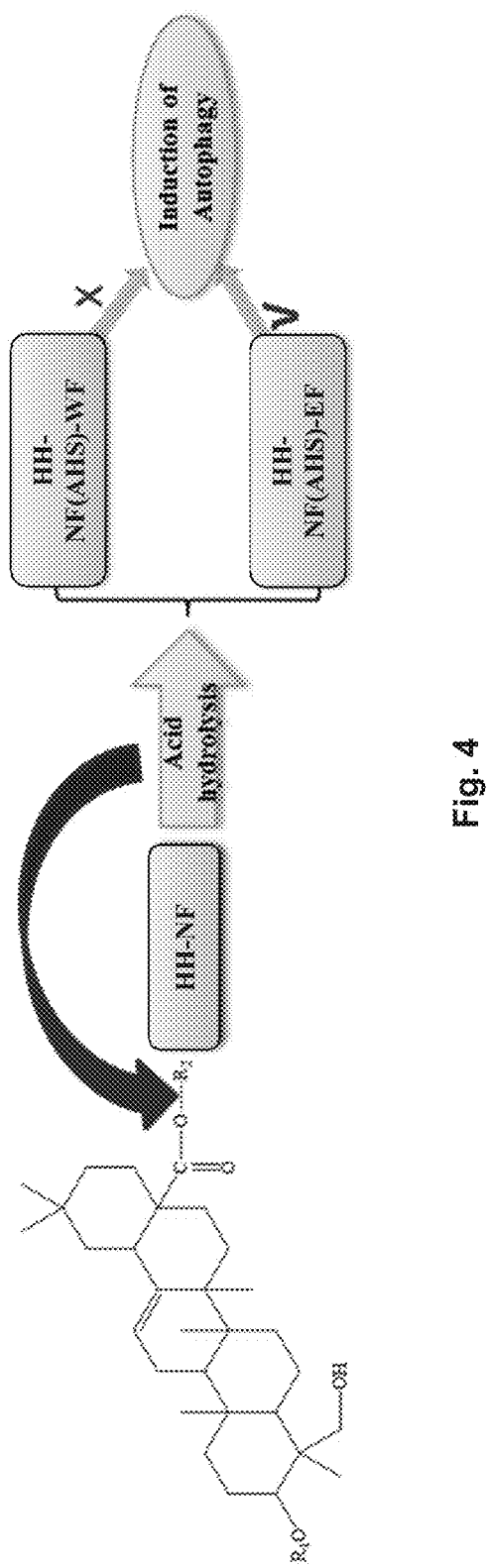
FIG. 4 is a schematic representation illustrating the preparation of two particular *Hedera helix* extracts obtained from acid hydrolysis of HH-NF followed by a partition extraction. The HH-NF was first subjected to an acid hydrolysis by adding hydrochloric acid and then heated to obtain a resultant acid hydrolyzed solution (AHS). The resultant AHS was partitioned to obtain a water portion of the resultant AHS (HH-NF(AHS)-WF) and ethyl acetate portion of the resultant AHS (HH-NF(AHS)-EF).

Saponins are known for being the major components in *Hedera helix*, which possess antispasmodic, antileishmanial, antifungal, anthelmintic, molluscicidal and antimutagenic properties (Mshvildadze, V. et al., Chem Pharm Bull 2004, 52:1411-1415). In general, while saponins containing ester glycosides ($R_2$ in FIG. 4 means glycosylation) are with higher polarity that can be extracted by n-butanol, sapogenins or saponins containing the oxygen glycosides ($R_1$ in FIG. 4 means glycosylation and $R_4$ is H) have relatively low polarity that are extracted with ethyl acetate (Mshvildadze, V. et al., Chem Pharm Bull 2004, 52:1411-1415, Li, D. W. et al., Biol Pharm Bull 2003, 26:429-433). As shown in the previous example, HH-EF possesses the highest autophagic effect, therefore, both triterpenoid sapogenins and triterpenoid saponins with low polarity might be responsible for inducing autophagy in PC-12 cells. To this end, HH-NF was acidly hydrolyzed by adding hydrochloric acid to obtain a solution of pH 2.5. The solution was then heated to completely hydrolyze all the triterpenoid saponins (ester glycosides). The resulting acid hydrolyzed solution was extracted with ethyl acetate (FIG. 4) and the cytotoxicity value ($IC_{50}$) and autophagic effect of both HH-NF(AHS)-WF and HH-NF-(AHS)-EF in PC-12 cells has been analyzed.

Figure 5:
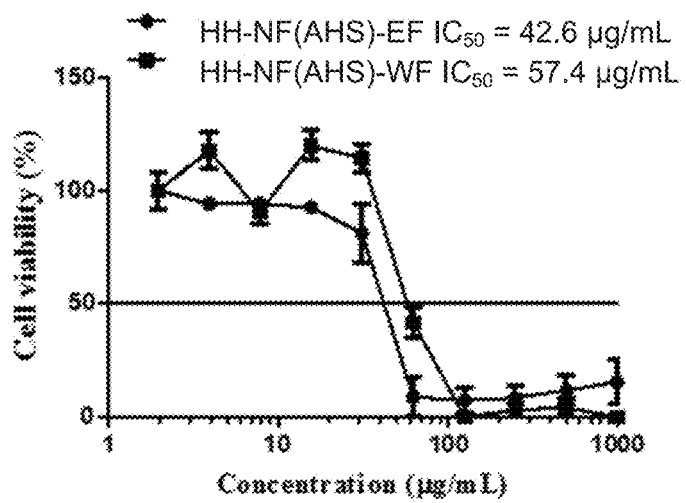
FIG. 5 shows the cell viability of HH-NF(AHS)-WF and HH-NF(AHS)-EF in PC-12 cells after 48 h of treatment.
Figure 6A:
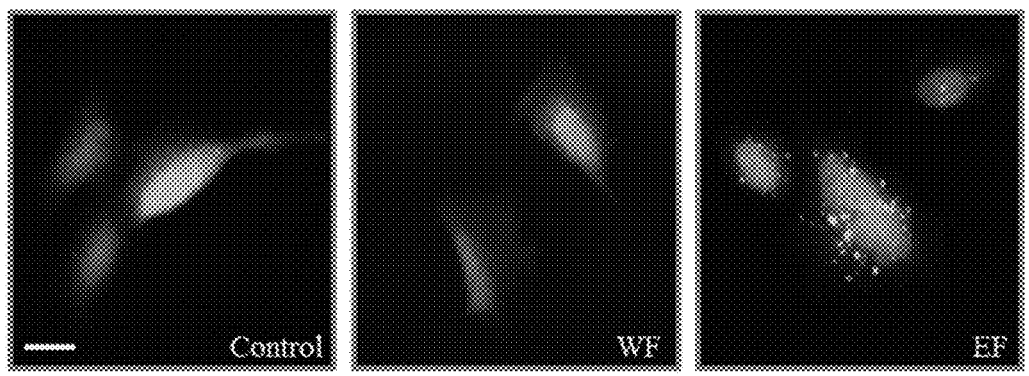
FIGS. 6A and 6B show the autophagic effect of HH-NF (AHS)-WF and HH-NF(AHS)-EF in GFP-LC3 transfected PC-12 cells.
Figure 6B:
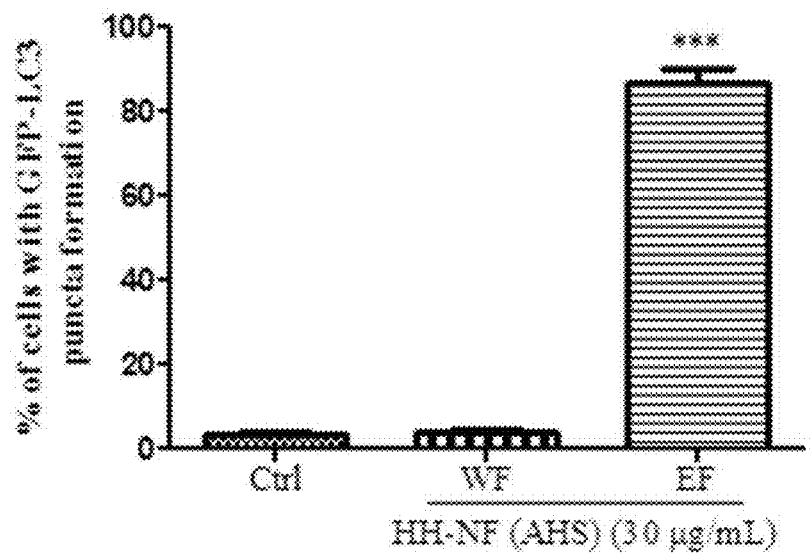
Figure 7A:
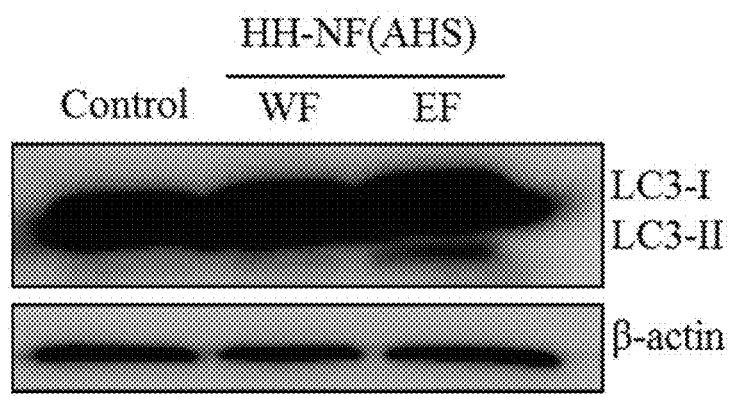
FIGS. 7A and 7B show the effect of HH-NF(AHS)-WF and HH-NF(AHS)-EF on the conversion of LC3 in PC-12 cells with Western blotting analysis. The cells were treated with 30 μg/mL HH-NF(AHS)-WF, 30 μg/mL HH-NF(AHS)-EF and positive control for 24 h.
Figure 7B:
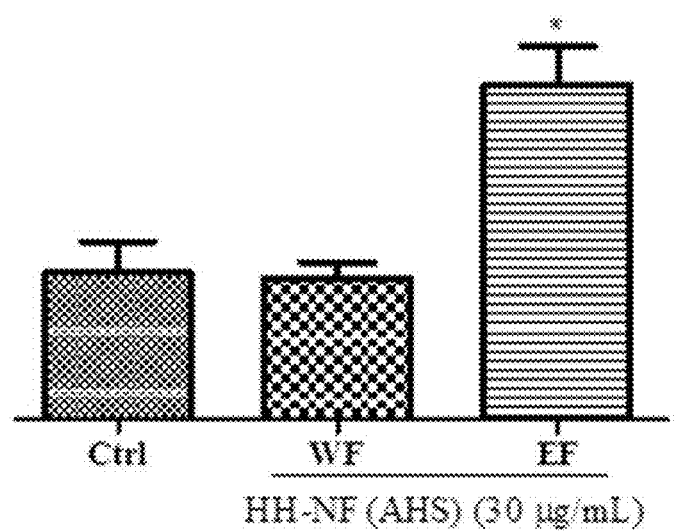

As shown in FIG. 5, while both HH-NF(AHS)-WF and HH-NF(AHS)-EF possess similar $IC_{50}$ values of 42.6 and 57.4 µg/mL, respectively, HH-NF(AHS)-EF possesses potent autophagic activity as revealed by the high percentage of cells with GFP-LC3 puncta formation (FIGS. 6A and 6B). This result was further confirmed by Western blotting which showed an increased expression of LC3-II in cells after treatment of HH-NF(AHS)-EF (FIGS. 7A and 7B). Consistent with the result that HH-NF(AHS)-WF did not induce autophagy (FIGS. 6 & 7), the triterpenoid sapogenins and triterpenoid saponins with low polarity in both HH-EF and HH-NF(AHS)-EF seem to be responsible for the autophagic effect of *Hedera helix*.

Example 3

Neuroprotective Effects in MPTP Induced Mouse Model of Parkinson's Disease (PD)

MPTP neurotoxin-induced motor deficits mice model: 8-week-old C57BL/6 mice (female body weight: 22±4 g and male body weight 25±4 g) were purchased from The Chinese University of Hong Kong (Hong Kong). The animals were housed in a 12 hours light/dark cycles and temperature-controlled room and given ad libitum access to food and water. All of the experiments were carried out in accordance to the "Institutional Animal Care and User Committee guidelines" of the Macau University of Science and Technology. A mixture of HH-EF and HH-NF(AHS)-EF in 1:1 ratio was prepared by dissolving in Mill-Q water (the mixture is further referred to as HH-EF' extract). C57BL/6 mice were randomly divided into four experimental groups as follows: (1) Normal control group without treatments; (2) MPTP-treated group; (3) MPTP-treated mice treated with 40 mg/kg HH-EF'; (4) MPTP-treated mice treated with 80 mg/kg HH-EF'. To begin, all HH-EF' treatment groups were gavage-fed with 40 mg/kg or 80 mg/kg of HH-EF' extract daily for 10 consecutive days before neurotoxin injection (pre-treatment). Neurotoxin MPTP (1-methyl-4-phenyl-1,2,3,6-tetrahydropyridine) was dissolved in buffer saline, and given to mice at a daily dose of 20 mg/kg/day by intraperitoneal (i.p.) injection (Schmidt, N., Ferger, B., J Neural Transm (Vienna) 2001, 108:1263-1282) for 10 consecutive days with or without HH-EF' extract feeding. Oral feeding of HH-EF' was performed 2 hours after the MPTP injection.

Behavioral swimming test: Animals were subjected to a swimming test 30 minutes after MPTP administration. Mice were observed by independent examiners who were blinded to the different treatments between groups. Each animal was placed in a container of water which the depth was about 10 cm. The water temperature was controlled at about 22-25° C. Swimming score was recorded with modification that used by Marshall and Berrios (Marshall, J. F., Berrios, N., Science 1979, 206:477-479). In general, the scoring criteria were as follows: Mice with continuous swimming movement: 3; Mice with occasional floating: 2.5; Mice with floating >50% of time: 2.0; Mice with occasional swimming only: 1.5; Mice with occasional swimming using hind limbs while floating on side: 1.0. Mice with no use of limbs: 0. Each animal was scored at 1-min intervals for 10 min (Donnan, G. A. et al., J Neurol Sci 1987, 77:185-191).

Behavioral rotarod test: The rotarod test, which requires animals to balance and walk on a rotating cylinder, is a widely used test to evaluate motor coordination and motor learning of the MPTP-mice (Sedelis, M. et al., Behav Brain Res 2001, 125:109-125, Kelly, M. A. et al., J Neurosci 1998, 18:3470-3479). To begin, mice were placed in a balanced position on a stationary 2 cm diameter cylinder at 30 min after MPTP injection. In 10 sec time, the rotarod was accelerated to a full speed of 20 rpm, then motor coordination can be assessed by comparing the latency to fall over time between treatment groups. Each mouse was evaluated for 3 times (with a maximum cut-off time of 1200 sec/time). To ensure accuracy of the obtained results, mice have to be trained to run on the rod at a higher speed than their normal pace before experiments started (Iancu, R. et al., Behavioural Brain Research 2005, 162:1-10, Rozas, G. et al., Brain Res 1997, 749:188-199).

Preparation of mice brain tissues for measurement of DA, hederagenin (i.e. triterpenoid of Formula (VI)) and α-hederin (i.e. triterpenoid of Formula (V)): Whole mice brains were collected and weighted after sacrificed. Each brain tissue was put into 500 µl of NaCl solution and ultra-sonicated for 40 s to give the whole tissue homogenate. Each tube of homogenate was set to a final volume of 800 µl. To begin, 200 µl of each tube of brain homogenate was spiked with 10 µl of 3, 4-dihydroxybenzylamine (DHBA) (0.5 mg/mL). 200 µl of methanol was then added to precipitate proteins with vortexing and centrifugation at 10000 rpm for 10 min. The supernatant was collected and remaining precipitate was re-extracted with 200 µl of methanol. The collected supernatant was then combined and dried by using dry nitrogen blowing instrument. The residue was reconstituted with 200 µl of 30% acetonitrile, and then 10 µl of the aliquot was injected into the LC-MS/MS system (Su, F. L. et al., Chromatographia 2009, 69:207-213).

5 mg of DA were dissolved with methanol to give a final stock standard solution of 0.5 mg/ml and stored at −80° C. For preparing the standard curve of DA, serial dilutions on DA standard solution combined with 10 µl of DHBA (0.5 mg/mL) were performed. 5 mg of hederagenin or α-hederin were dissolved in DMSO to give a stock solution of 50 mM. This stock solution was further diluted with methanol to a final concentration of 50 µM before serial dilution on hederagenin and α-hederin were prepared for the standard curve.

The measurement of dopamine (DA), hederagenin and α-hederin level in mice brain tissues: Internal standard (IS, DHBA), DA, hederagenin and α-hederin level in the mouse brain, were quantified using UHPLC/MS/MS system which includes Agilent 1290 Infinity UHPLC, and Agilent 6460 Triple Quadrupole, equipped with an electrospray ionization interface used to generate positive ions for the determination of DA; negative ion mode for the measurement of hederagenin and α-hederin in mouse brains. The compounds in plasma samples were analyzed by using the Agilent Zorbax Eclipse Plus C-18 column with a particle size of 1.8 µm (flow rate: 0.35 mL/min). The mobile phase for the determination of DA was 98% mobile phase A (0.1% formic acid in water) and 2% mobile phase B (0.1% formic acid in ACN) in 5 min. The mobile phase for the measurement of hederagenin and α-hederin was set as follows: mobile phase A (0.1% formic acid in water) and mobile phase B (0.1% formic acid in ACN) 0-5 min, 5-50% B; 5-7 min, 50-95% B; 7-10 min, 95% B; 10-11 min, 95-5% B; 11-15 min, 5% B. The column and auto-sampler temperature were maintained at 40° C. and 4° C., respectively. Data were analyzed by using Agilent MassHunter Workstation software B.01.03. The gas temperature was set at 325° C. with a flow rate of 10 L/min. Gases were set at 40 psi for the nebulizer, capillary, 4000 V. The fragmentor was 90, 90, 110, 135 and 300 for DA, DHBA, α-hederin and hederagenin, respectively. The collision energy was set at 3, 1, 55 and 46 for DA, DHBA, α-hederin and hederagenin, respectively. The mass transitions were as follows based on multiple reaction monitoring: m/z 154.0→137.0 for DA, 140.1→123.1 for DHBA, 795.3→471.4 for α-hederin and 471.3→393.1 for hederagenin, respectively. Quantification was performed by selected reaction monitoring of the product ion for DA, by using the IS method with peak area ratios and a linear least-squares regression curve. The measurements of α-hederin and hederagenin in mouse brain were done by using the standard and linear least-squares regression curve.

Results

Up to now, classical cellular and animal models set up by the addition of neurotoxin MPTP, are the most widely used PD platforms for testing neuroprotective drugs (Meredith, G. E. et al., J Parkinsons Dis 2011, 1:19-33). These models are well established to induce motor deficits and neurotoxicity in *drosophila*, rats, mice, and primates. MPTP, a highly lipophilic compound which crosses the blood brain barrier, is converted by astrocytes to its toxic 1-methyl-4-phenylpyridinium (MPP+) metabolite ion, and resembles a number of known environmental neurotoxins such as herbicide (paraquat) or insecticide (rotenone), to induce degeneration of dopaminergic neurons.

Figure 8:
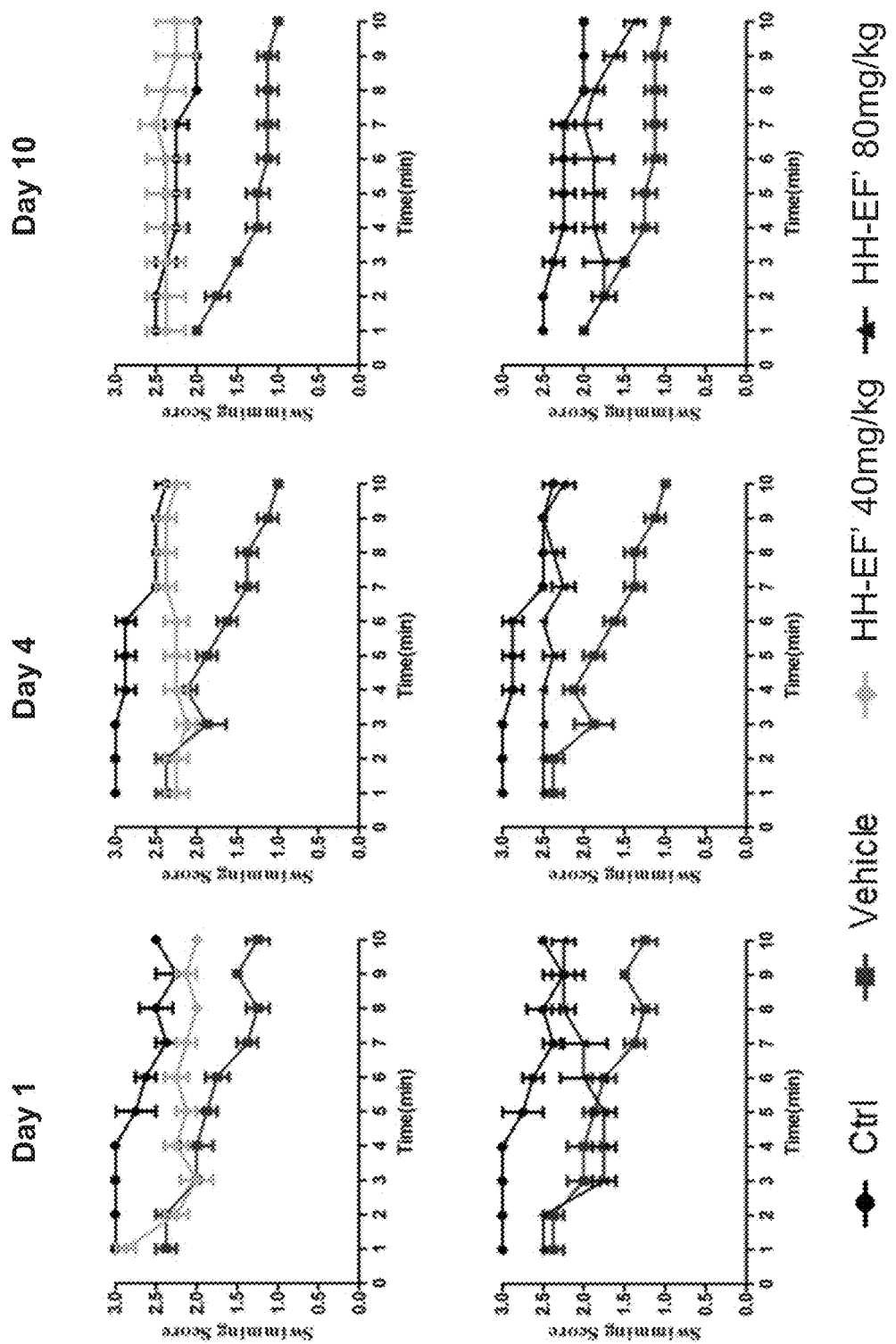
FIG. 8 shows the effect of MPTP (1-methyl-4-phenyl-1, 2,3,6-tetrahydropyridine) in mice in a behavior swimming test. The mice were treated with MPTP (i.e. with vehicle), MPTP and 40 mg/kg HH-EF', or MPTP and 80 mg/kg HH-EF'. Their swimming abilities were scored on Day 1, Day 4 and Day 10 after the corresponding treatment.

Motor dysfunctions of PD include rigidity, tremor and akinesia. Recent study in the use of swim test in monitoring the behavioral deficits of MPTP-induced PD mice models demonstrated a negative correlation between swim-score and MPTP level in mice, confirming the use of the swim test as a reliable technique to motor deficits of MPTP-induced models (Haobam, R. et al., Behav Brain Res 2005, 163:159-167). To evaluate the protective function of *Hedera helix* relating to motor dysfunctions in MPTP-treated mice, HH-EF and HH-NF(AHS)-EF in 1:1 ratio were administrated to (10 days of pre-treatment) and after the start of MPTP treatment for 10 consecutive days. To begin, C57BL/6 mice were treated with 20 mg/kg of MPTP for 10 consecutive days, HH-EF and HH-NF(AHS)-EF in 1:1 ratio (referred to as HH-EF') was administrated daily to mice 2 hours before MPTP injection. Mice were subjected to swim-test for every 3 days after the start of MPTP injection. As shown in FIG. 8, while the control C57BL/6 healthy mice demonstrated a better swimming ability as indicated by a higher swim score, MPTP-treated mice (vehicle) showed a relatively lower swim score. As compared to the group treated with MPTP, HH-EF' extract treated group showed a significant recovery in swim score, suggesting the protective role of HH-EF' in the alleviation of motor deficits induced by MPTP.

Figure 9:
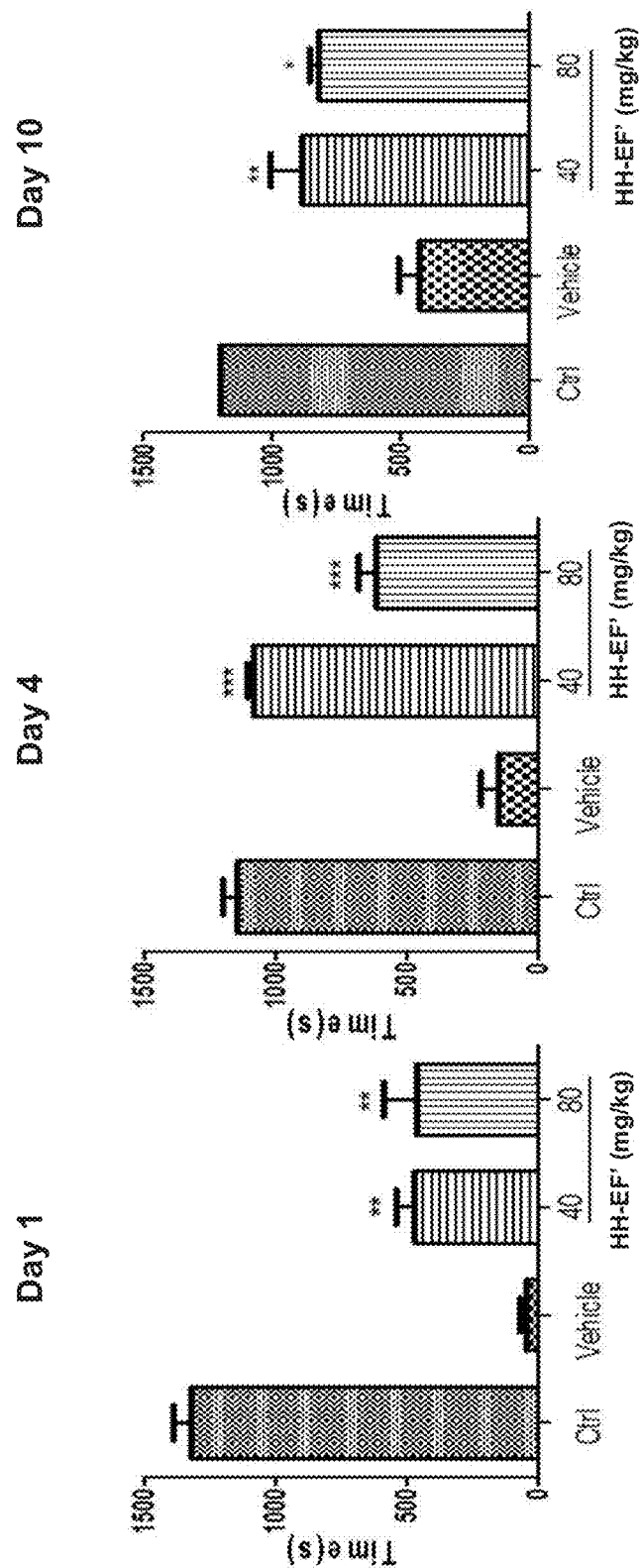
FIG. 9 shows the effect of MPTP in mice in a behavioral rotarod test. The mice were treated with MPTP, MPTP and 40 mg/kg HH-EF', or MPTP and 80 mg/kg HH-EF'. Their latencies to fall over time were assessed on Day 1, Day 4 and Day 10 after the corresponding treatment.
Figure 10:
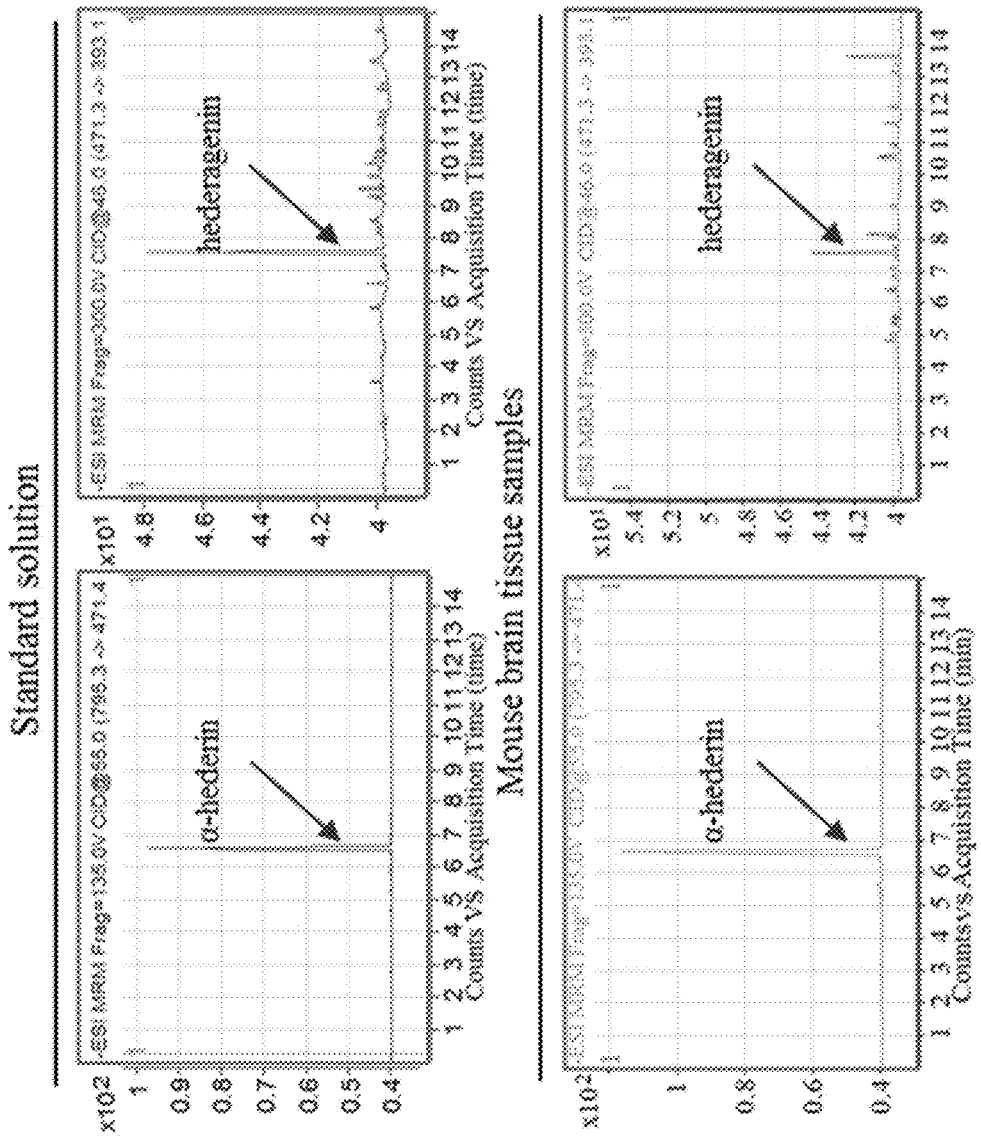
FIG. 10 shows the presence of hederagenin and α-hederin in brain tissue samples obtained from treated mice via liquid chromatography-tandem mass spectrometry (LC-MS/MS) analysis. The mice were treated with 80 mg/kg HH-EF'.

Another common way to evaluate motor deficits in MPTP-induced mice is by the rotarod test. This is performed by measuring the duration the mice ran on the rotating rod by using an automated device. To begin, motor coordination of mice was assessed by placing each C57BL/6 mouse on the horizontal rod that keeps rotating about its axis (Deacon, R. M., J Vis Exp 2013:e2609). The time that the mouse remains upright and running without falling off was recorded. As shown in FIG. 9, while the MPTP-treated mice demonstrated a significant shorter duration in maintaining upright on the rotating rod without falling, HH-EF' extract-treated mice showed a significant longer duration remaining on the rod as measured at day 1, day 4 and day 10 post-MPTP injections, implying the improvement of mice motor function after HH-EF' treatments. Further analysis by UHPLC/MS/MS system showed that both hederagenin (3.39 nM) and α-hederin (2.98 nM) could be detected in the brain tissue (with 80 mg/kg HH-EF' treatment) (FIG. 10), suggesting that these two potential neuroprotective agents are able to cross the blood-brain barrier, which may be responsible for the protective effect of *Hedera helix*.

Example 4

Active Autophagic Components in HH-EF and HH-NF(AHS)-EF

Materials and Methods

The identification of the bioactive components in HH-EF and HH-NF(AHS)-EF: The identification of the bioactive components in HH-EF and HH-NF(AHS)-EF was performed by using CMC method (Wu, A. G. et al., Sci Rep 2015, 5:17199). The measurement of hederagenin and α-hederin in HH-EF, HH-NF and HH-NF(AHS)-EF was carried out by UHPLC (Agilent Technologies 1290 Series)

equipped with the time of flight MS (Agilent Technologies 6230) with a jet stream ion source, which was operated in negative ion mode during the analysis. All the samples were separated and analyzed on an Agilent Zorbax Eclipse Plus C-18 column with a particle size of 1.8 µm (flow rate: 0.35 mL/min). The mobile phase was set as follow: mobile phase A (0.1% formic acid in water) and mobile phase B (0.1% formic acid in ACN): 0-8 min, 5-70% B; 8-11 min, 70-100% B; 11-14 min, 100% B; 14.1-18 min, 5% B. For UHPLC-TOF-MS analysis, the data were acquired in the scan mode (m/z 100 to 1600 Da with 2.0 spectra/s). Data were analyzed by using Agilent MassHunter Workstation software B.01.03. 5 mg of hederagenin or α-hederin were dissolved in DMSO to give a stock solution of 50 mM. This stock solution was further diluted with methanol to a final concentration of 50 µM before serial dilution on hederagenin and α-hederin were prepared for the standard curve.

Results

Figure 11:
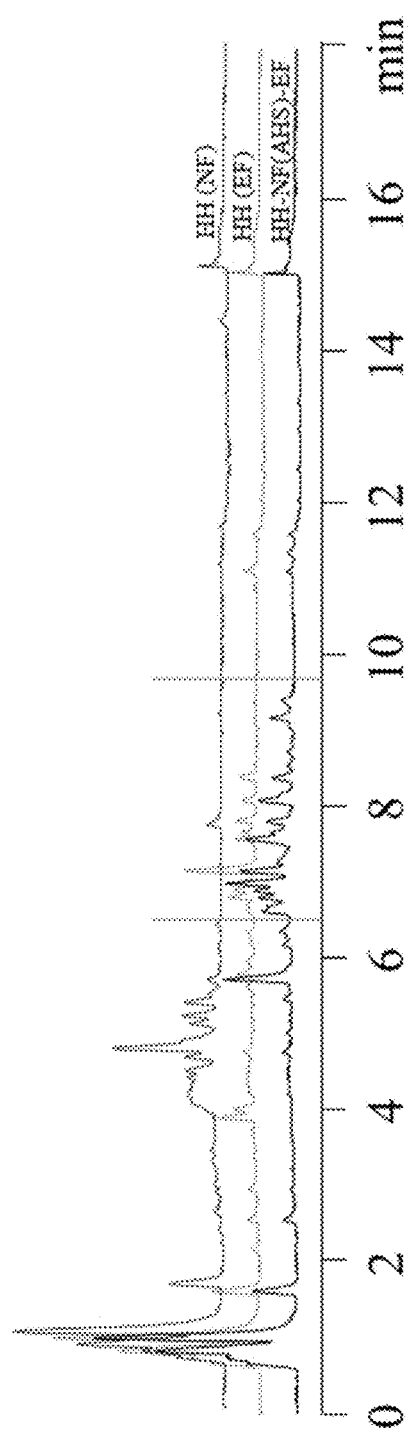
FIG. 11 shows the total ion chromatographic pattern of different *Hedera helix* extracts HH-NF, HH-EF, and HH-NF (AHS)-EF. The chromatographic peak pattern of HH-NF (AHS)-EF at elution time 6.5 min to 9.5 min is similar to that of HH-EF.

Through analyzing HH-NF, HH-NF(AHS)-EF and HH-EF by UHPLC-TOF/MS, chromatographic peaks confirmed that the compounds (triterpenoids), eluted between 4-6 min of HH-NF separation, were hydrolyzed into the compounds eluted between 6.5-9.5 min of HH-NF(AHS)-EF separation. Concordantly, chromatographic peak pattern of HH-NF(AHS)-EF was similar as the peaks eluted between 6.5 to 9.5 min of HH-EF separation (FIG. 11), suggesting the major chemical compounds presented in the HH-NF(AHS)-EF are similar to HH-EF, which may be responsible for the induction of autophagy.

Figure 12:
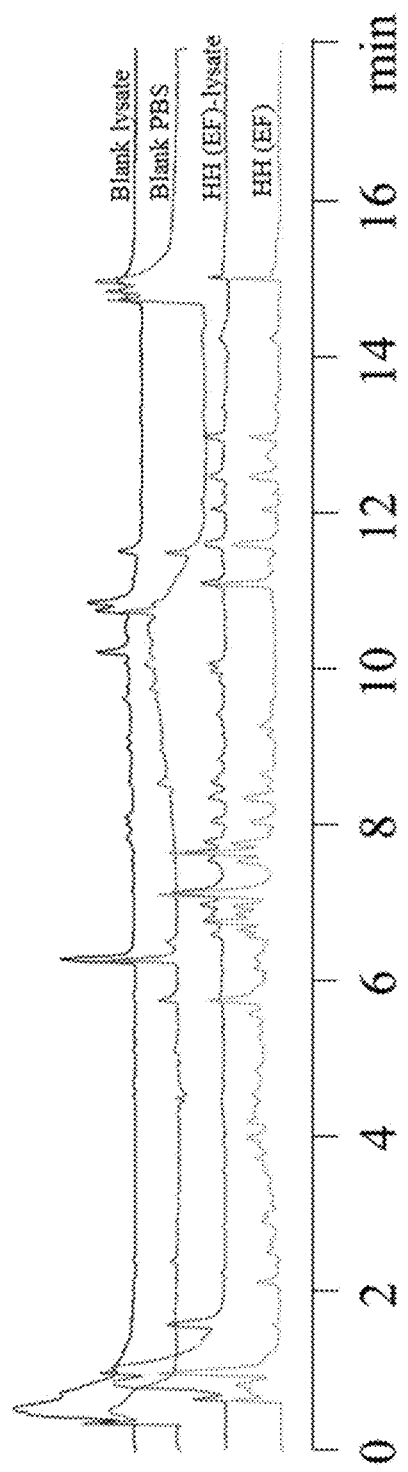
FIG. 12 shows the total ion chromatographic pattern of samples derived from cell membrane chromatography. The samples include control groups, i.e. a lysate of PC-12 cells without *Hedera helix* treatment, and a solution of PBS; and treatment groups, i.e. a lysate of PC-12 cells treated with HH-EF for 4 h, and a mixture of HH-EF.
Figure 13A:
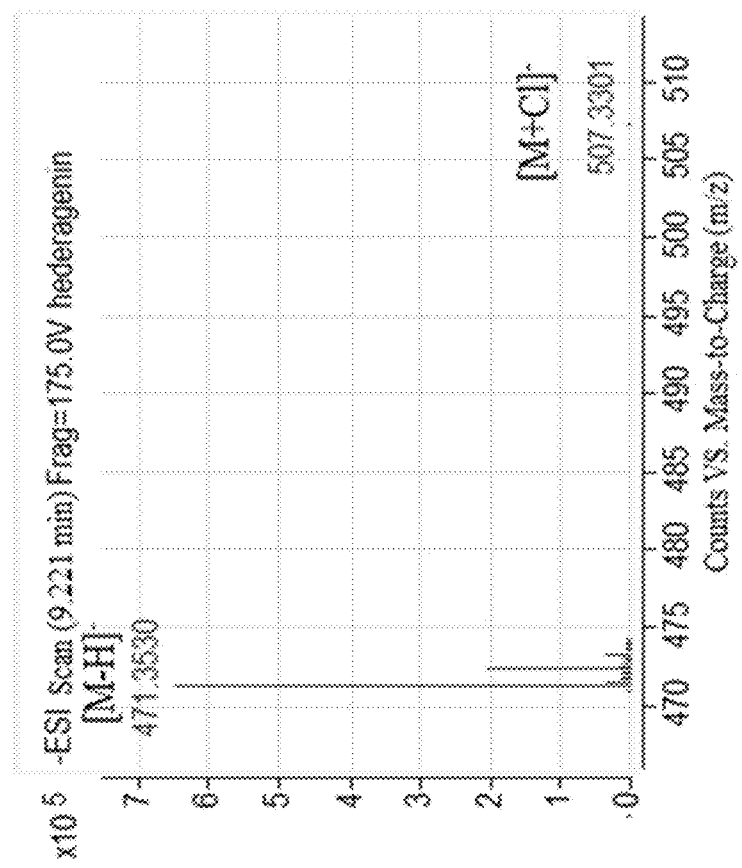
FIG. 13A shows the MS spectrum of hederagenin.
Figure 13B:
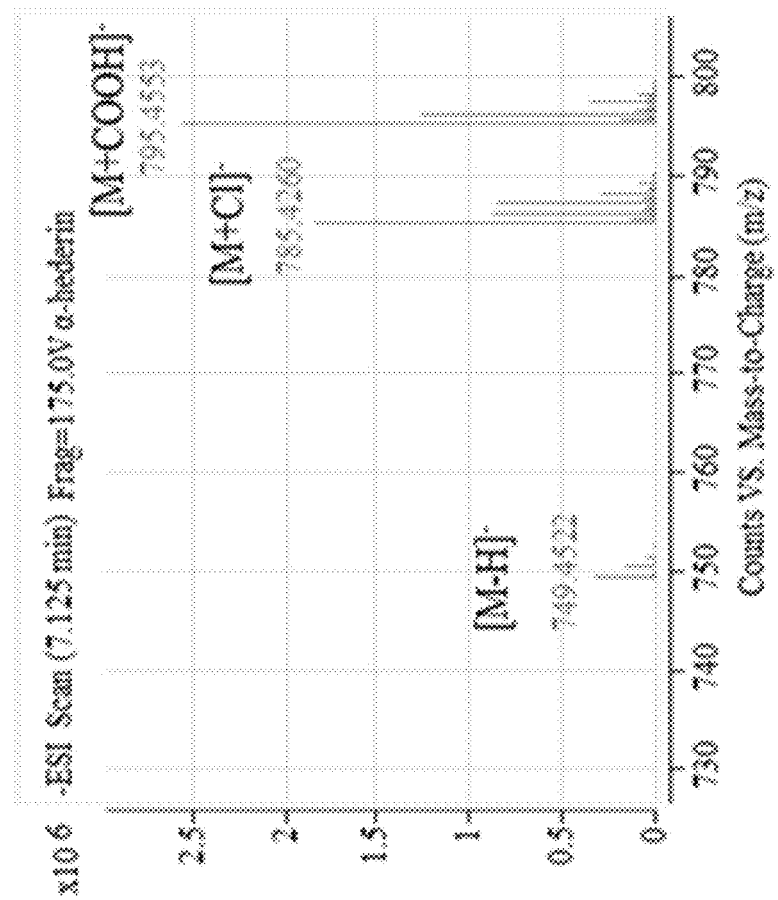
FIG. 13B shows the MS spectrum of α-hederin.
Figure 14:
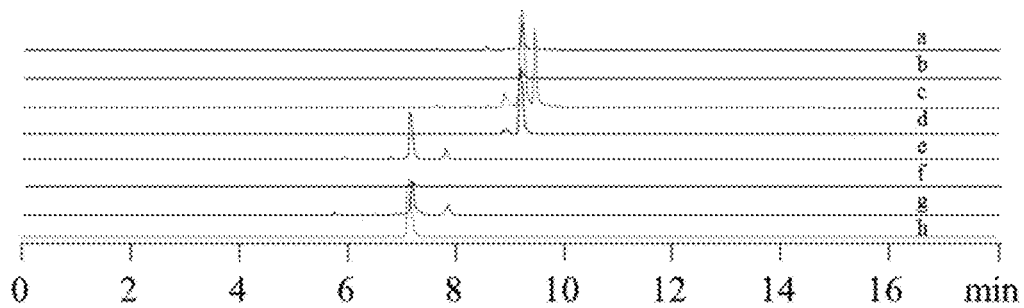
FIG. 14 shows the extract ion chromatographic (EIC) patterns of the exact concentration (μM) of hederagenin and α-hederin in 250 μg/mL of different *Hedera helix* extracts, in particular (a) refers to the pattern of hederagenin in HH-EF; (b) refers to the pattern of hederagenin in HH-NF; (c) refers to the pattern of hederagenin in HH-NF(AHS)-EF; (d) refers to the pattern of hederagenin in the standard solution; (e) refers to the pattern of α-hederin in HH-EF; (f) refers to the pattern of α-hederin in HH-NF; (g) refers to the pattern of α-hederin in HH-NF(AHS)-EF; (h) refers to the pattern of α-hederin in the standard solution.

In order to identify the active components responsible for the autophagic effect of HH-EF, we applied the cell membrane chromatography (CMC) to identify the chemical components that possess binding affinity to the cellular membrane of PC-12 cells. This is done by incubating PC-12 cells with the HH-EF for 4 h. After incubation, while chemical components without binding affinity to the cell membrane were washed away by PBS buffer, those components that could bind on cell membrane were retained for analysis. FIG. 12 shows the components that were bound on the cellular membrane, while the chromatograms of blank lysate or PBS buffer were shown as control. By comparing the accurate mass and molecular formula of the identified compounds from CMC to reported compounds of *Hedera helix*, hederagenin and α-hederin were identified as the possible components responsible for the autophagic activities of *Hedera helix* (FIG. 13). In addition, the concentration and the percentage of both hederagenin and α-hederin in HH-NF(AHS)-EF, HH-NF and HH-EF was measured. As shown in Table 2, only a small amount of α-hederin and hederagenin are presented in HH-NF when compared to HH-NF(AHS)-EF or HH-EF. Furthermore, HH-NF(AHS)-EF contained a higher concentration of hederagenin and α-hederin when compared to HH-EF. This suggests that hederagenin and α-hederin work as the autophagy inducers responsible for the bioactivity of *Hedera helix*.

TABLE 2 concentration of hederagenin and α-hederin in the Hedera helix extracts

| Components | Retention time (min) | Concentration | | |
|---|---|---|---|---|
| | | HH-NF(AHS)-EF | HH-NF | HH-EF |
| α-hederin | 7.22 | 22.62 | 0.42 | 19.88 |
| hederagenin | 9.22 | 74.42 | 0.38 | 2.95 |

Example 5

Induction of Autophagy by Hederagenin (Triterpenoid of Formula (VI)) and α-Hederin (Triterpenoid of Formula (V))

Materials and Methods

Cytotoxicity Assays: Cell viability was measured by using the MTT method (3-[4,5-dimethylthiazol-2-yl]-2,5-diphenyl tetrazolium bromide) as described previously (Wu, A. G. et al. Int J Mol Sci 2013, 14:22618-22641). Absorbance (OD) of cell samples was obtained by spectrophotometer at 570 nm. The percentage of cell viability was calculated by using the formula: cell viability (%)=cells number$_{treated}$/cells number$_{DMSO}$ control×100. All MTT data were calculated from three independent experiments. Cell viability was also measured by flow cytometry using the Annexin V staining kit (BD Biosciences, San Jose, Calif., USA).

Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Immunocytochemistry and fluorescence microscopy: GFP-LC3 puncta formation was analyzed as described previously (Wu, A. G. et al. Int J Mol Sci 2013, 14:22618-22641). Firstly, cells were plated on top of coverslips inside a 6-well culture dish. After compounds treatments, cells were fixed with 4% paraformaldehyde for 20 min. Fluor-Save™ mounting media (Calbiochem, San Diego, Calif., USA) was used to mount the coverslips with cells before subjected to fluorescence microscopic analysis. The number of GFP-positive cells, and cells with GFP-LC3 puncta formation was examined and counted under the Nikon ECLIPSE 80i microscope by using 40× of magnification. In order to standardize the quantitation, the percentage of cells with autophagy induction was defined by counting the number of cells with punctate GFP-LC3 fluorescence in GFP-positive cells. A minimum of 1000 GFP-positive cells from 3 randomly selected fields were scored.

Results

Figure 15:
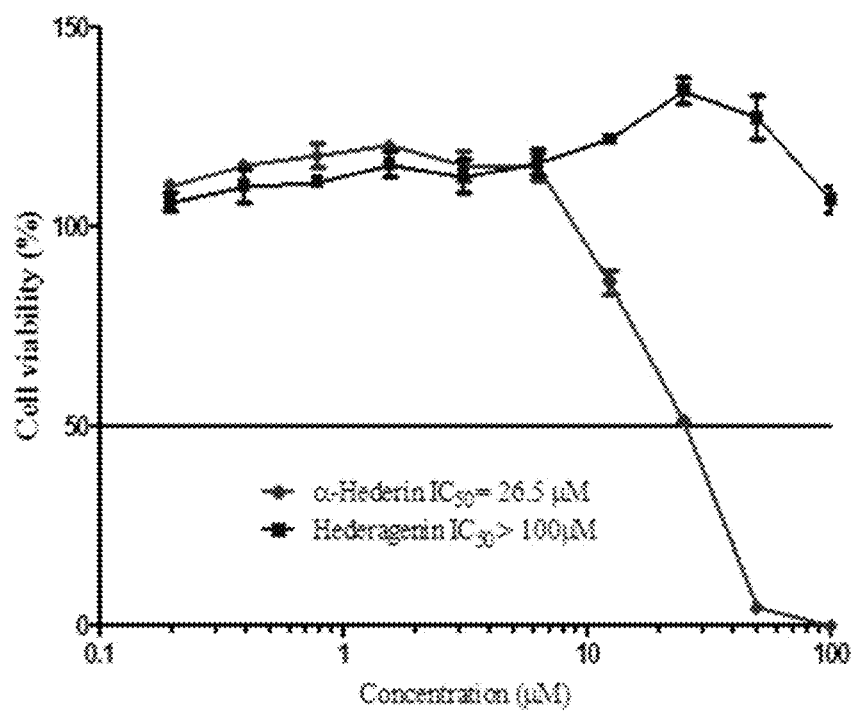
FIG. 15 shows graphs relating to the cell viability of PC-12 cells after 48 h of treatment with hederagenin or α-hederin. The cell viability was measured with an MTT assay.
Figure 16A:
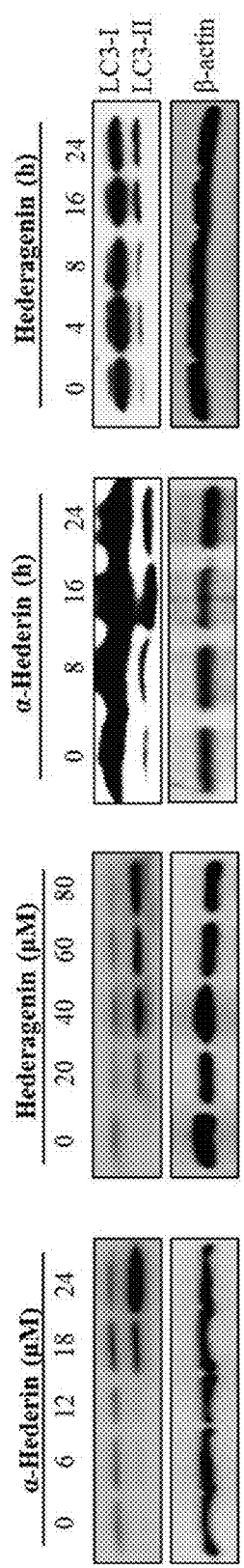
FIGS. 16A and 16B show the effect of hederagenin and α-hederin on the conversion of LC3 in PC-12 cells with Western blotting analysis. The cells were treated with hederagenin or α-hederin for various durations and in different concentrations.
Figure 16B:
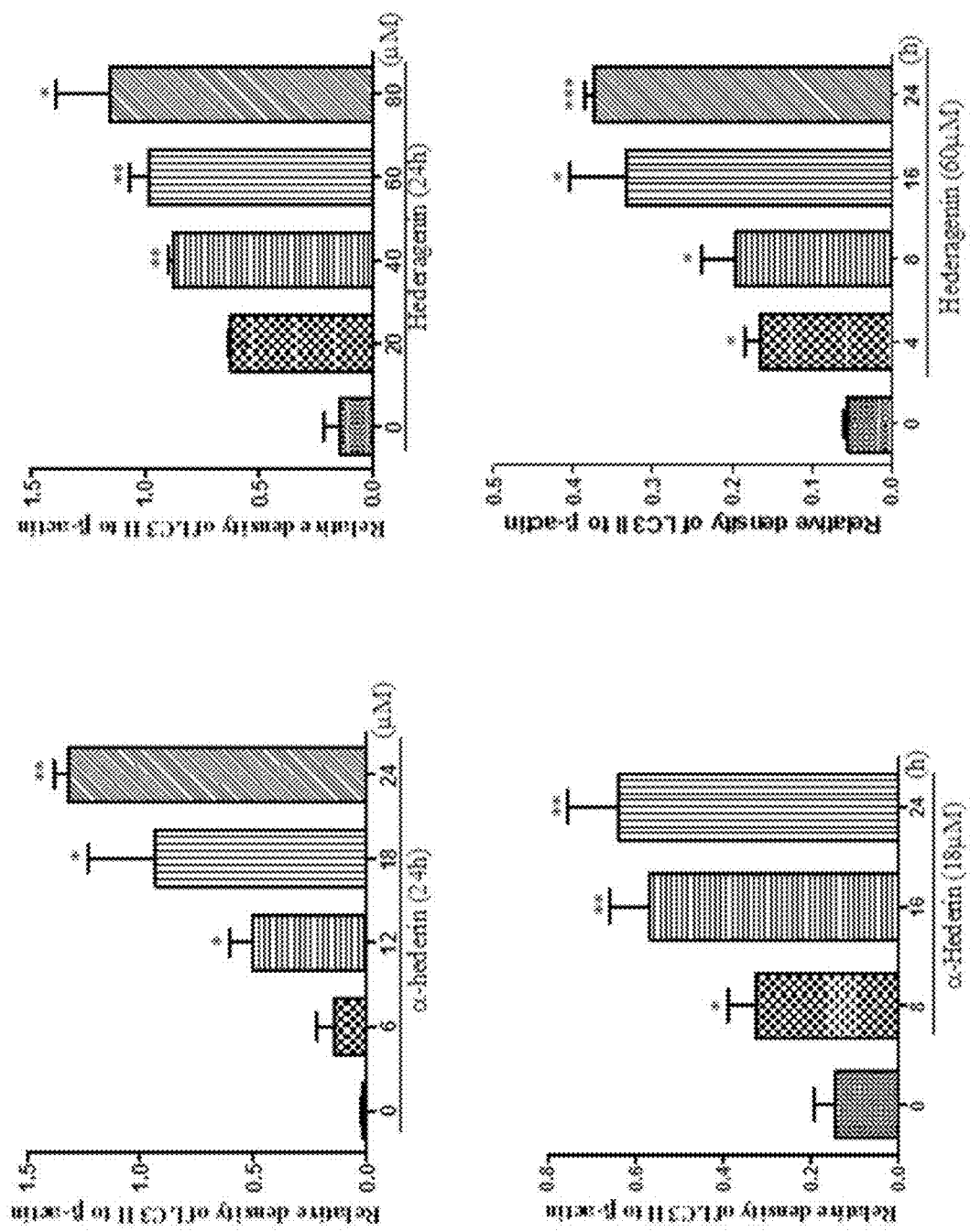
Figure 17A:
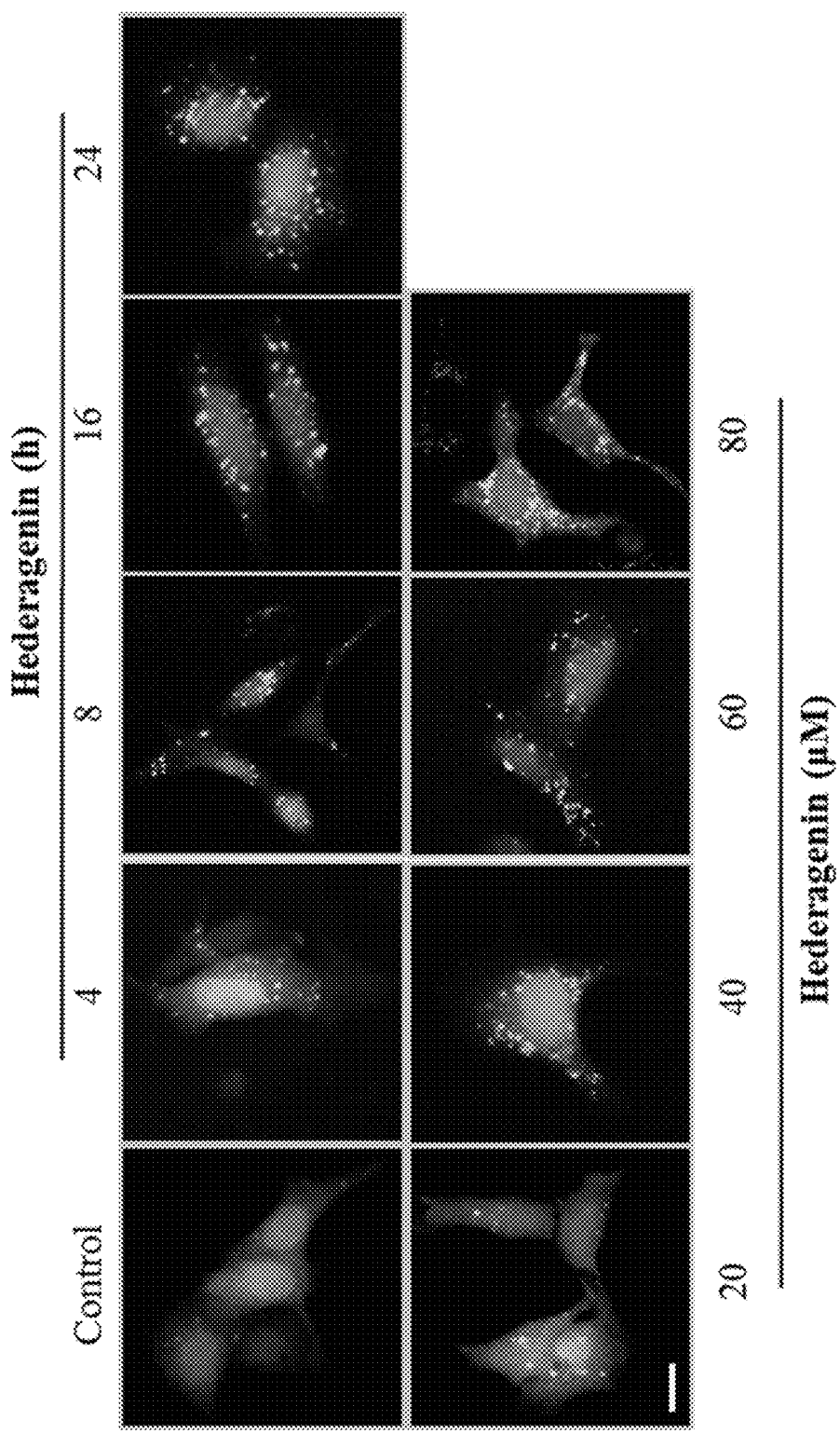
FIGS. 17A and 17B show the autophagic effect of hederagenin in GFP-LC3 transfected PC-12 cells. The cells were treated with 20 μM, 40 μM, 60 μM or 80 μM hederagenin for 24 h, or treated with 60 μM hederagenin for 4, 8, 16, or 24 h.
Figure 17B:
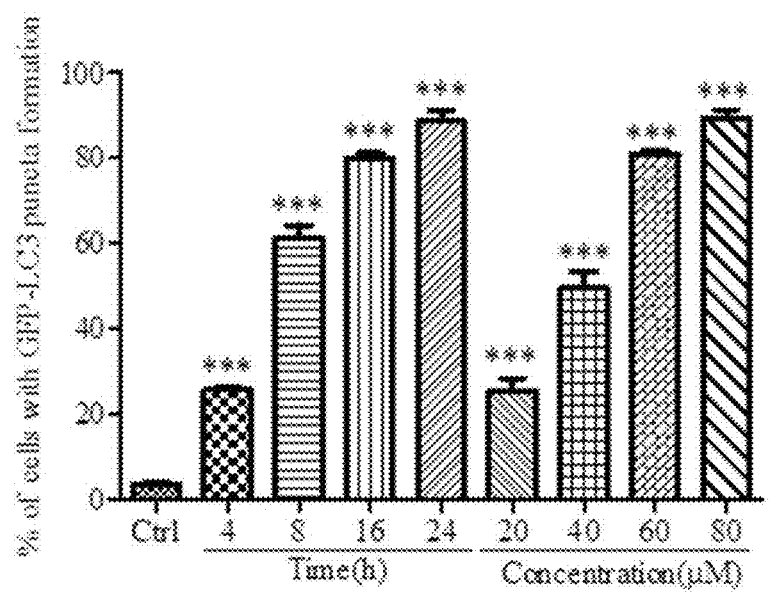
Figure 18A:
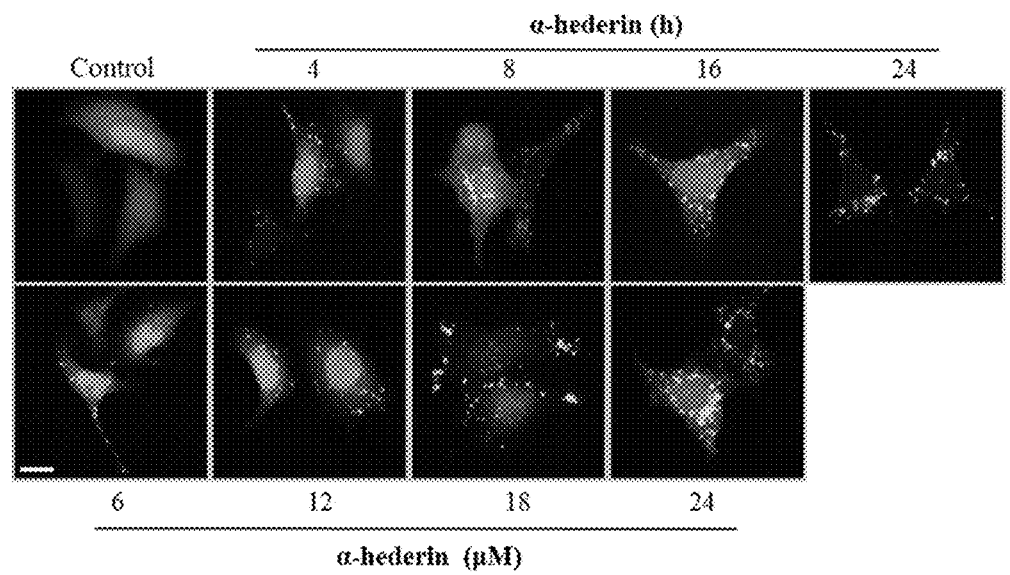
FIGS. 18A and 18B show the autophagic effect of α-hederin in GFP-LC3 transfected PC-12 cells. The cells were treated with 6 μM, 12 μM, 18 μM or 24 μM α-hederin for 24 h, or treated with 18 μM α-hederin for 4, 8, 16, or 24 h.
Figure 18B:
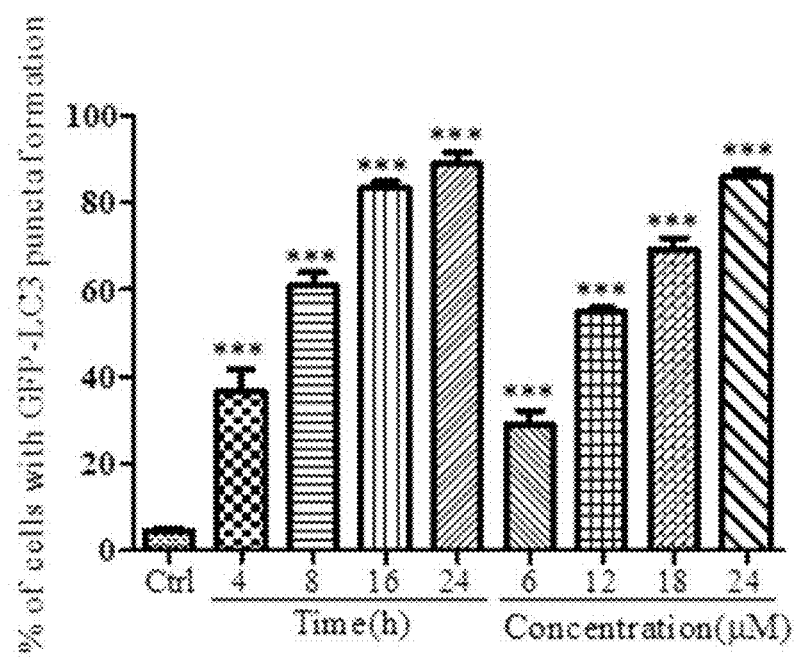

Firstly, the IC$_{50}$ value of both hederagenin and α-hederin was evaluated by MTT assay for 48 h. The mean IC$_{50}$ value of hederagenin and α-hederin was estimated as >100 µM and 26.5 µM, respectively (FIG. 15). Furthermore, both hederagenin and α-hederin trigger an increase in the protein level of LC3-II via a dose- and time-dependent manner (FIGS. 16A and 16B). The autophagic effect of hederagenin and α-hederin was further validated by monitoring and quantitating the formation of GFP-LC3-II puncta by immunofluorescence microscopy. As shown by an increased formation of fluorescent LC3 II puncta in cells (FIGS. 17 and 18), it has been confirmed that both hederagenin and α-hederin trigger the induction of autophagy (time- and dose-dependently) in PC-12 cells.

Example 6

Hederagenin (Triterpenoid of Formula (VI)) and α-Hederin (Triterpenoid of Formula (V)) Induce Autophagic Flux in PC-12 Cells Materials and Methods Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Immunocytochemistry and fluorescence microscopy: GFP-LC3 puncta formation was analyzed as described previously (Wu, A. G. et al. Int J Mol Sci 2013, 14:22618-22641). Firstly, cells were plated on top of coverslips inside a 6-well culture dish. After compounds treatments, cells were fixed with 4% paraformaldehyde for 20 min. Fluor-Save™ mounting media (Calbiochem, San Diego, Calif., USA) was used to mount the coverslips with cells before subjected to fluorescence microscopic analysis. The number of GFP-positive cells, and cells with GFP-LC3 puncta formation was examined and counted under the Nikon ECLIPSE 80i microscope by using 40× of magnification. In order to standardize the quantitation, the percentage of cells with autophagy induction was defined by counting the number of cells with punctate GFP-LC3 fluorescence in GFP-positive cells. A minimum of 1000 GFP-positive cells from 3 randomly selected fields were scored.

Results

Figure 19A:
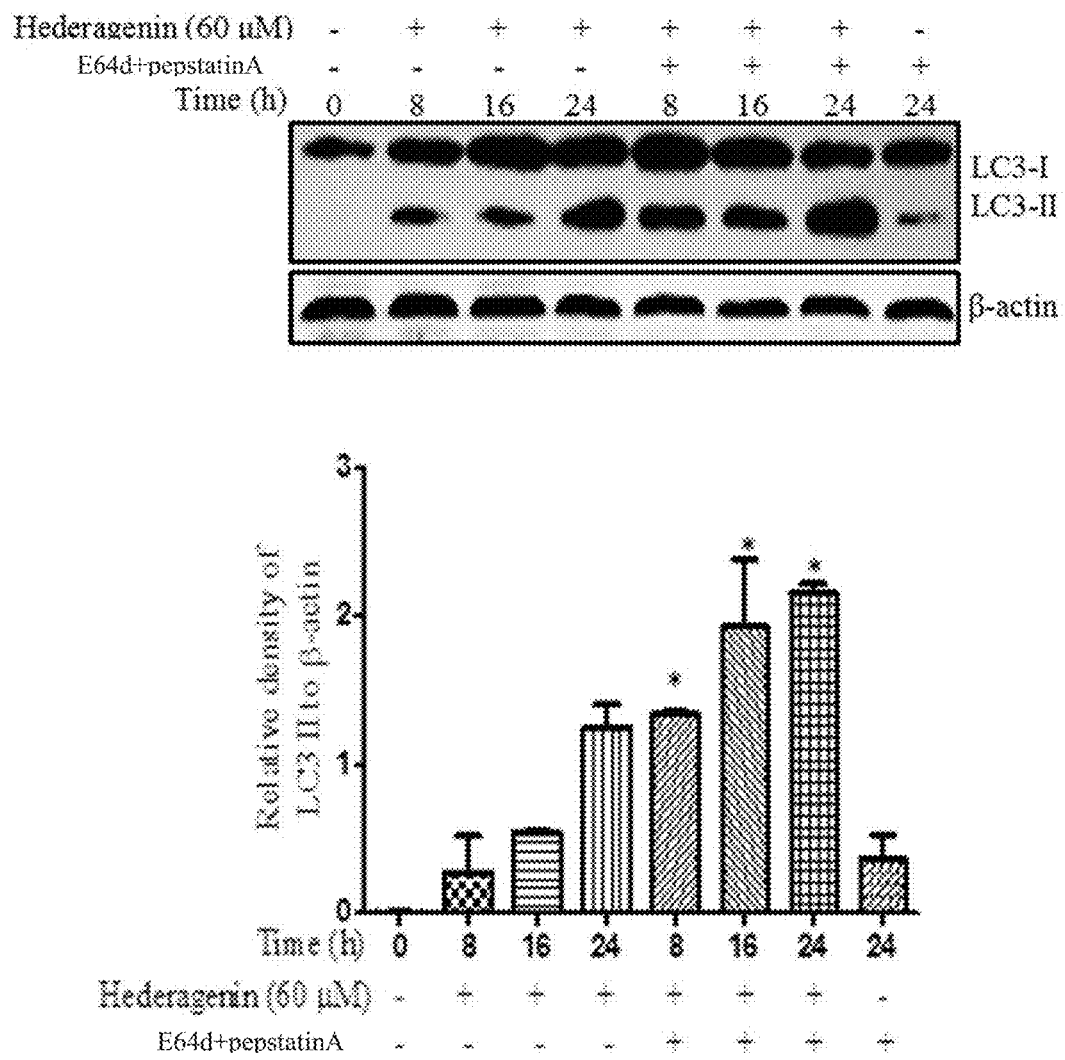
FIGS. 19A and 19B show the effect of hederagenin and α-hederin on the conversion of LC3 in PC-12 cells in the presence or absence of lysosomal protease inhibitors with Western blotting analysis.
Figure 19B:
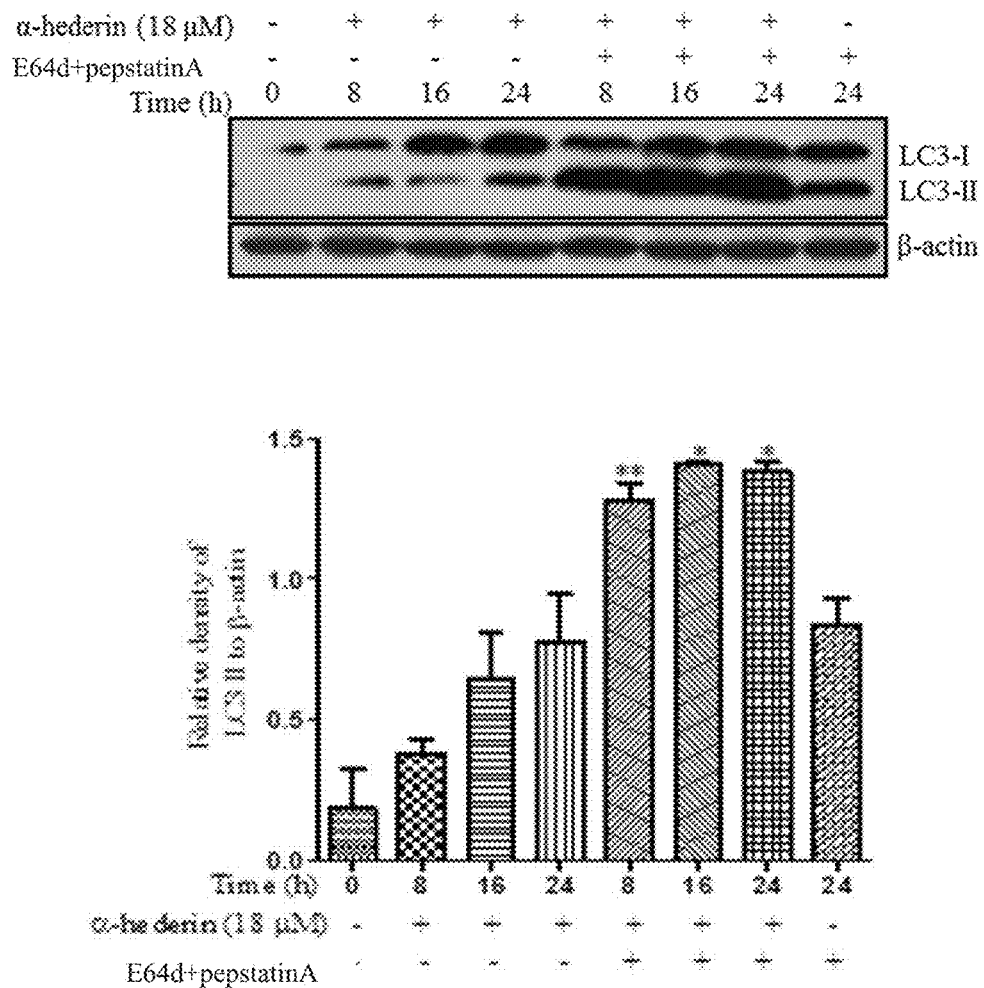
Figure 20A:
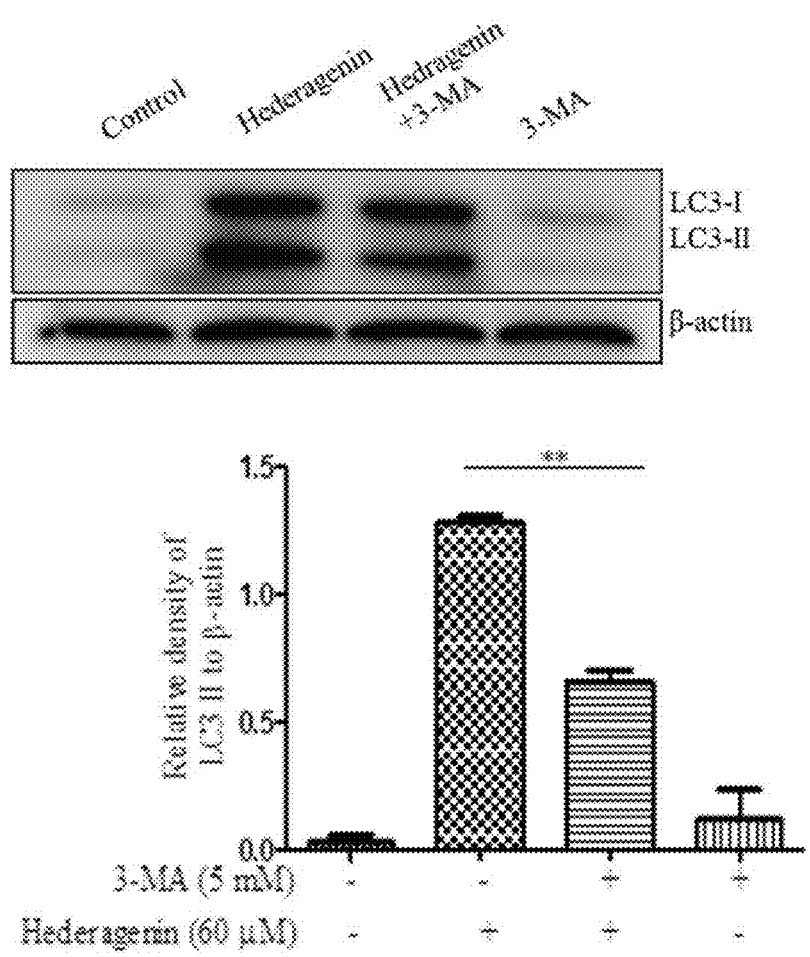
FIGS. 20A and 20B show the effect of hederagenin and α-hederin on the conversion of LC3 in PC-12 cells in the presence or absence of an autophagy inhibitor with Western blotting analysis.
Figure 20B:
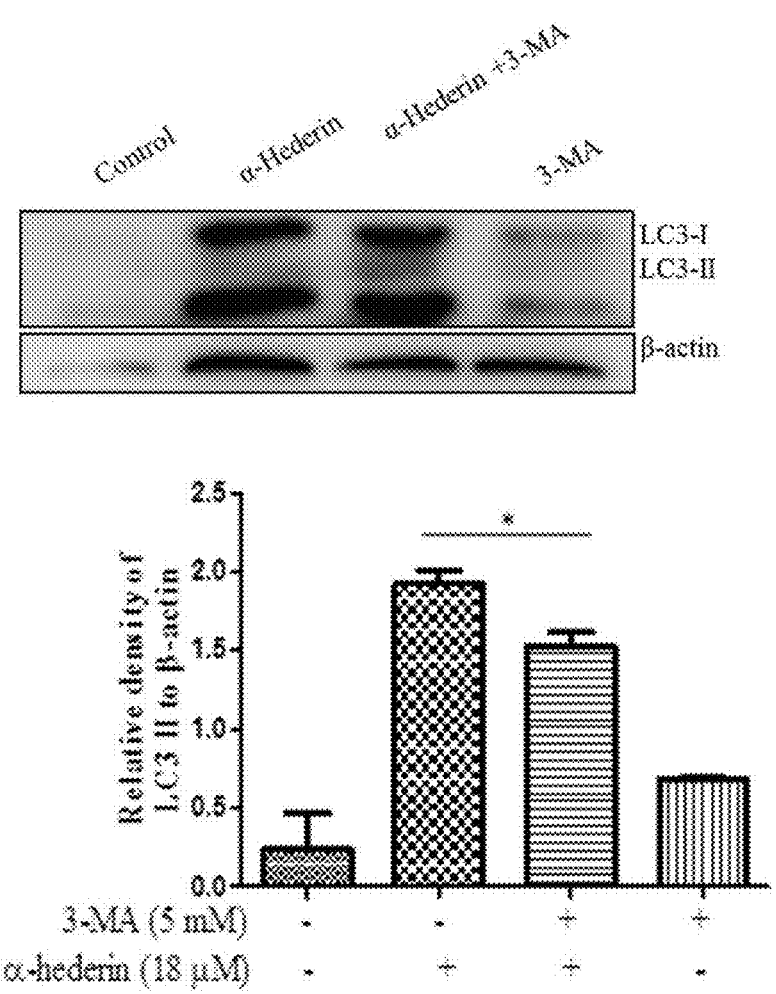
Figure 21A:
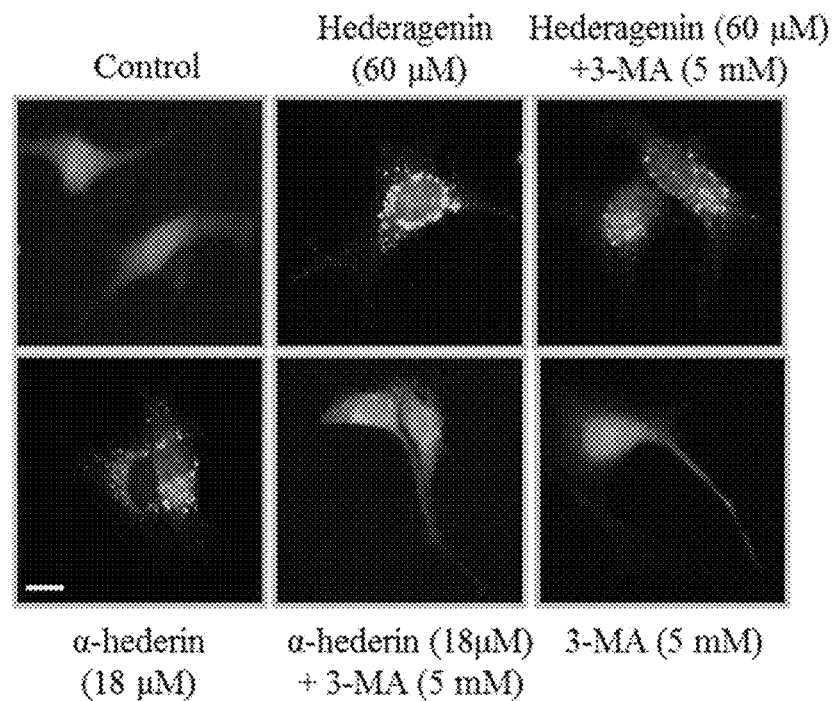
FIGS. 21A and 21B show the autophagic effect of hederagenin and α-hederin in GFP-LC3 transfected PC-12 cells.
Figure 21B:
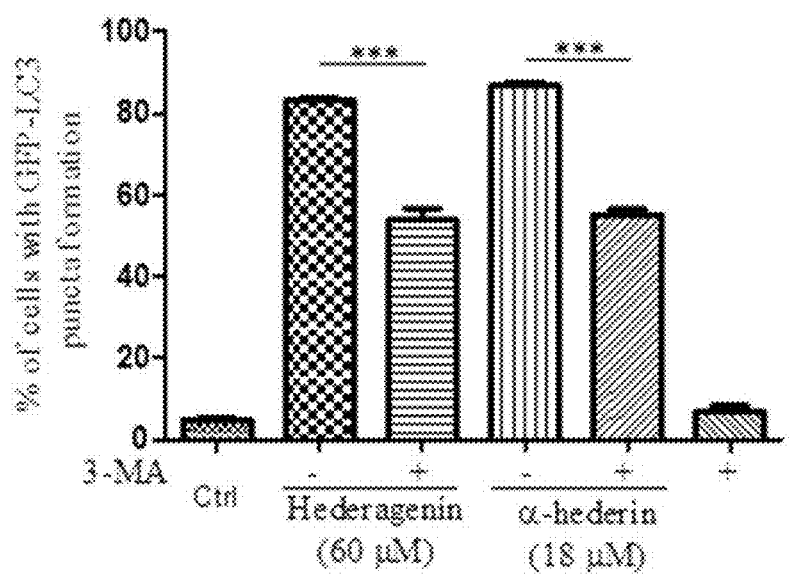

To confirm the autophagic flux induced by hederagenin and α-hederin, lysosomal degradation was inhibited by the addition of two lysosomal protease inhibitors, E64d and pepstatin A, when evaluating the protein level of the key autophagic protein, LC3-II. This is because the failure in fusion of autophagosomes and lysosomes could also lead to an increased protein level of LC3-II in Western blot, or GFP-LC3 puncta formation in fluorescence images, due to a reduction in turnover of autophagosomes (Klionsky, D. J. et al., Autophagy 2012, 8:445-544). As shown in FIGS. 19A and 19B, both hederagenin and α-hederin significantly increase the rate of LC3-II formation with the presence of E64d and pepstatin A, when compared with treatment of compounds alone. This result confirmed the dose-dependent induction of autophagic flux after hederagenin and α-hederin treatments. To further confirm the compounds-mediated autophagy flux, 3-methyladenine (3-MA) which blocks autophagy via inhibition of type III phosphatidylinositol 3-kinases was used. Consistently, the addition of 3-MA decreases the rate of autophagy as demonstrated by a decreased protein level of LC3-II (FIGS. 20A and 20B) and percentage of cells with GFP-LC3 puncta formation (FIGS. 21A and 21B) after hederagenin or α-hederin treatments, suggesting the autophagic property of the two triterpenoids from *Hedera helix*.

Example 7

Hederagenin (Triterpenoid of Formula (VI)) and α-Hederin (Triterpenoid of Formula (V)) Induce Autophagy Via AMPK-mTOR Signaling Cascade Materials and Methods Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Immunocytochemistry and fluorescence microscopy: GFP-LC3 puncta formation was analyzed as described previously (Wu, A. G. et al. Int J Mol Sci 2013, 14:22618-22641). Firstly, cells were plated on top of coverslips inside a 6-well culture dish. After compounds treatments, cells were fixed with 4% paraformaldehyde for 20 min. Fluor-Save™ mounting media (Calbiochem, San Diego, Calif., USA) was used to mount the coverslips with cells before subjected to fluorescence microscopic analysis. The number of GFP-positive cells, and cells with GFP-LC3 puncta formation was examined and counted under the Nikon ECLIPSE 80i microscope by using 40× of magnification. In order to standardize the quantitation, the percentage of cells with autophagy induction was defined by counting the number of cells with punctate GFP-LC3 fluorescence in GFP-positive cells. A minimum of 1000 GFP-positive cells from 3 randomly selected fields were scored.

Results

Figure 22A:
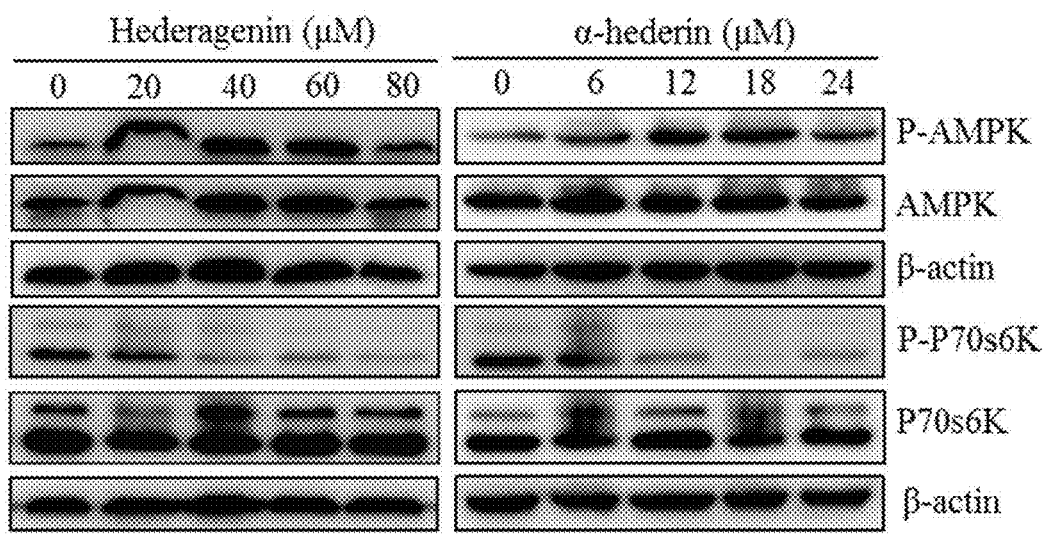
FIGS. 22A and 22B show the effect of hederagenin and α-hederin on proteins involved in the AMPK-mTOR signaling pathway with Western blotting analysis. The cells were treated with hederagenin with a concentration from 0 μM to 80 μM, or treated with α-hederin with a concentration from 0 μM to 24 μM for 24 h.
Figure 22B:
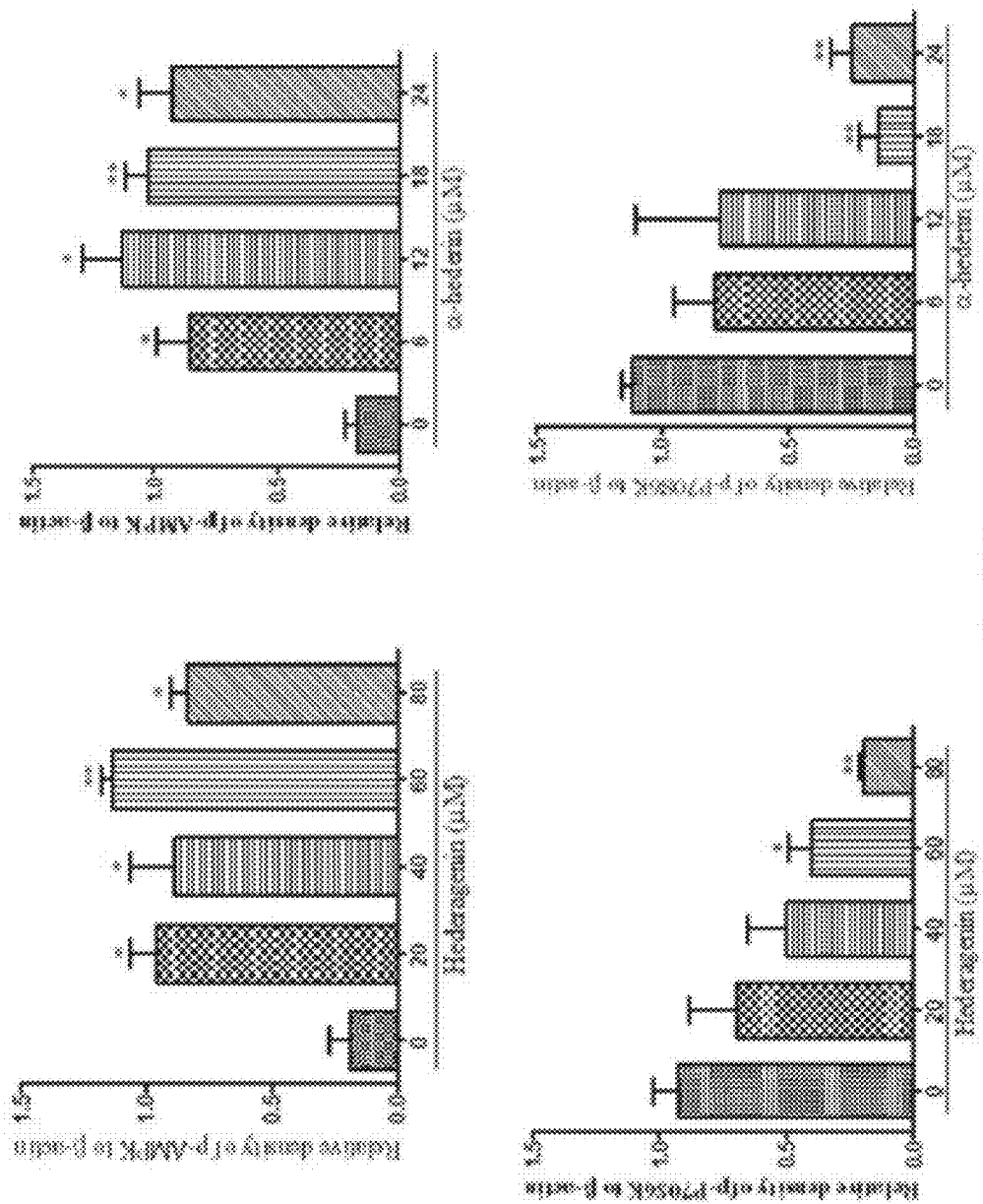

Autophagy is promoted by the activation of AMP activated protein kinase (AMPK), a key energy sensor for maintaining normal cellular metabolism and energy homeostasis, especially under low intracellular ATP conditions such as starvation or hypoxia. To further explore the possible mechanistic action of hederagenin or α-hederin, the effect on the phosphorylation of AMPK was therefore investigated (Mizushima, N., Klionsky, D. J. et al., Annu Rev Nutr 2007, 27:19-40). As shown in FIGS. 22A and 22B, both hederagenin and α-hederin induce an increased phosphorylation of AMPK.

Figure 23A:
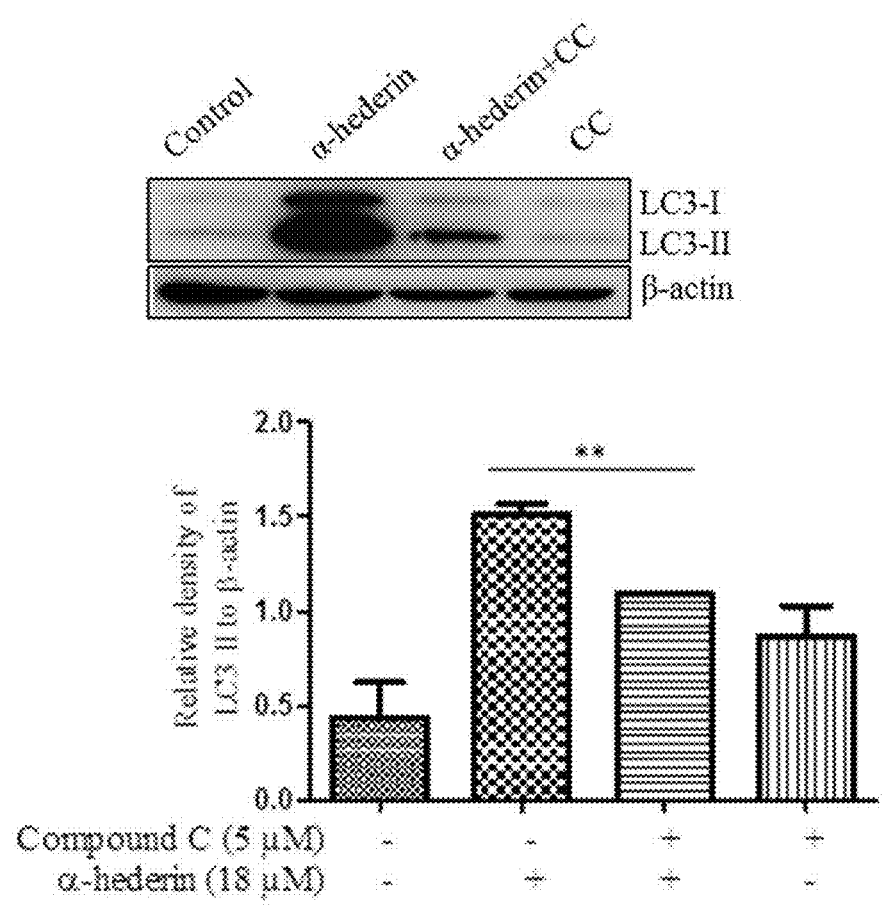
FIGS. 23A and 23B show the effect of hederagenin and α-hederin on the conversion of LC3 in PC-12 cells in the presence or absence of an AMPK inhibitor, compound C (CC) with Western blotting analysis.
Figure 23B:
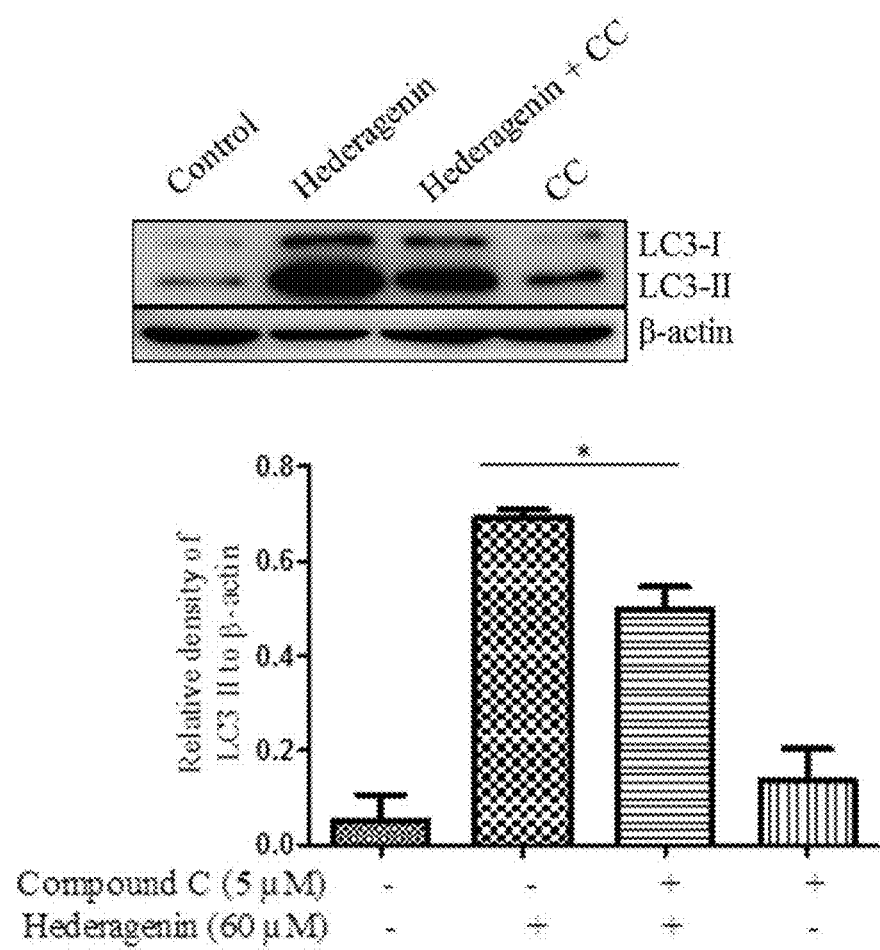
Figure 24A:
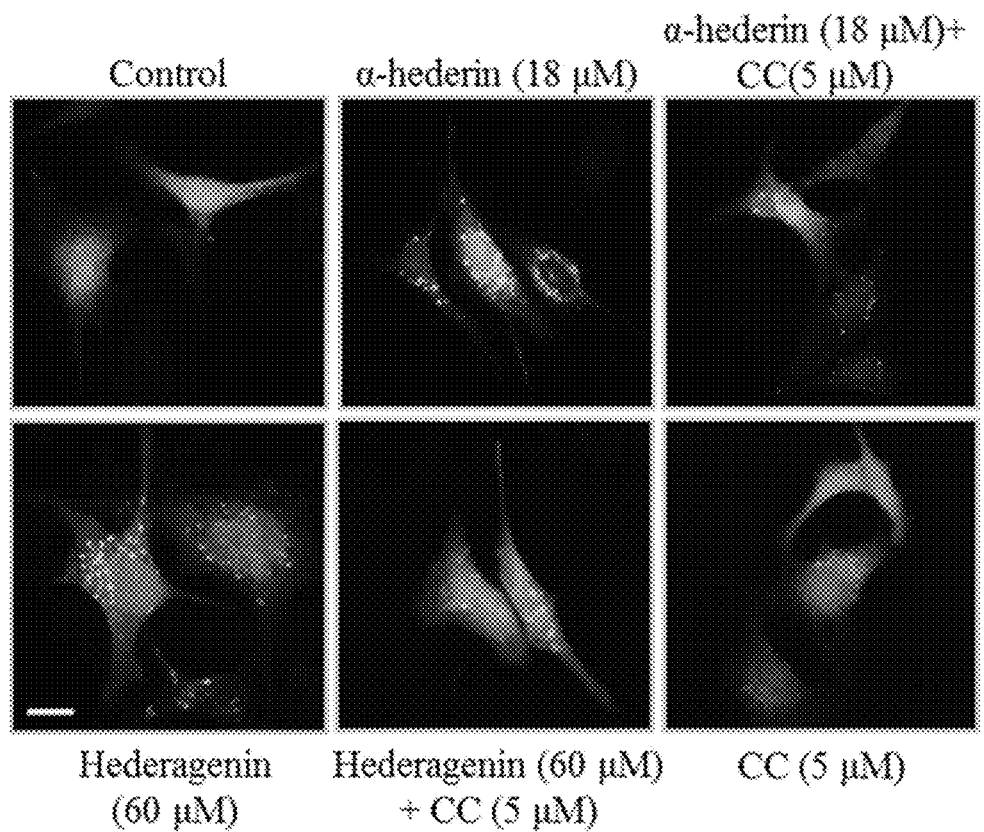
FIGS. 24A and 24B show the autophagic effect of hederagenin and α-hederin in GFP-LC3 transfected PC-12 cells.
Figure 24B:
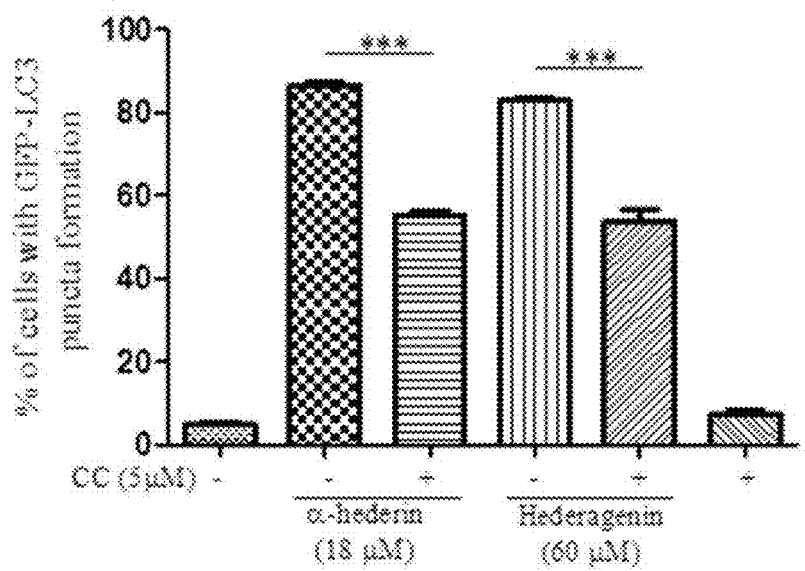

Downstream of AMPK activation is the phosphorylation of the tumor suppressing protein tuberous sclerosis complex (TSC2), and the suppression of mTOR which works as the central regulator for well-coordination of growth factors and signals for cell growth. While the suppression of mTOR could lead to the induction of autophagy, hederagenin or α-hederin also lead to a reduced phosphorylation of p70S6K, which is a downstream target of mTOR (FIG. 22A). Further investigation on the AMPK pathway was studied by the additional of AMPK inhibitor compound C (CC) during hederagenin and α-hederin treatment. As shown in FIGS. 23A and 23B, there is a significant reduction in protein level of LC3-II and the formation of GFP-LC3 puncta (FIGS. 24A and 24B) in hederagenin- or α-hederin-treated cells with the presence of CC. This confirmed the involvement of the AMPK-mTOR signaling pathway.

Example 8

Hederagenin (Triterpenoid of Formula (VI)) and α-Hederin (Triterpenoid of Formula (V)) Induce Autophagy and Degradation of Mutant Huntingtin Proteins Via ATG7 Gene Dependent Mechanism Materials and Methods Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Immunocytochemistry and fluorescence microscopy: In brief, GFP-LC3 puncta formation was analyzed as described previously (Wu, A. G. et al. Int J Mol Sci 2013, 14:22618-22641). Firstly, cells were plated on top of coverslips inside a 6-well culture dish. After compounds treatments, cells were fixed with 4% paraformaldehyde for 20 min. Fluor-Save™ mounting media (Calbiochem, San Diego, Calif., USA) was used to mount the coverslips with cells before subjected to fluorescence microscopic analysis. The number of GFP-positive cells, and cells with GFP-LC3 puncta formation was examined and counted under the Nikon ECLIPSE 80i microscope by using 40× of magnification. In order to standardize the quantitation, the percentage of cells with autophagy induction was defined by counting the number of cells with punctate GFP-LC3 fluorescence in GFP-positive cells. A minimum of 1000 GFP-positive cells from 3 randomly selected fields were scored.

Detection of mutant huntingtin proteins or inclusions: To further investigate the protective effects of hederagenin and α-hederin, PC-12 cells transfected with GFP-HTT 74 plasmids by using Lipofectamine Plus LTX reagent (Invitrogen, Paisley, Scotland, UK). Cells were then treated with either hederagenin or α-hederin for a further 24 h to determine the protein level of mutant huntingtin by Western blot analysis using an antibody against GFP (Ravikumar, B. et al., Nat Genet 2004, 36:585-595). On the other hand, ATG7 wild-type and ATG7-deficient MEF cells transfected with EGFP-HTT 74 were analyzed for the formation of huntingtin inclusion after 24 h of hederagenin or α-hederin treatment. Percentages of cells with cytoplasmic GFP-huntingtin (GFP-HTT74) inclusion formation were counted by the number of cells with GFP inclusions over the total number of GFP-positive cells in the same field under fluorescent microscopic analysis. More than 200 GFP-positive cells were scored for each treatment.

Results

Until now, 32 autophagy-related genes (ATG) that are responsible for 3 major mammalian autophagy induction processes including 1) the membrane initiation, 2) nucleation, and 3) elongation and completion in the formation of autophagosomes have been identified. Among them, ATG 7 gene is an E1-like enzyme in the two major ubiquitin-like protein conjugation systems responsible for the formation of autophagosomes. In the first ubiquitin-conjugation system containing ATG12-ATG5-ATG16L, the ATG7 activates the ATG12 through an ATP-dependent manner; in the second ubiquitin-like protein conjugation system, the modification of mammalian homolog of ATG8 (LC3) by the phospholipid phosphatidylethanolamine (PE) responsible for the formation of autophagosomes, is facilitated by the ATG7.

Figure 25A:
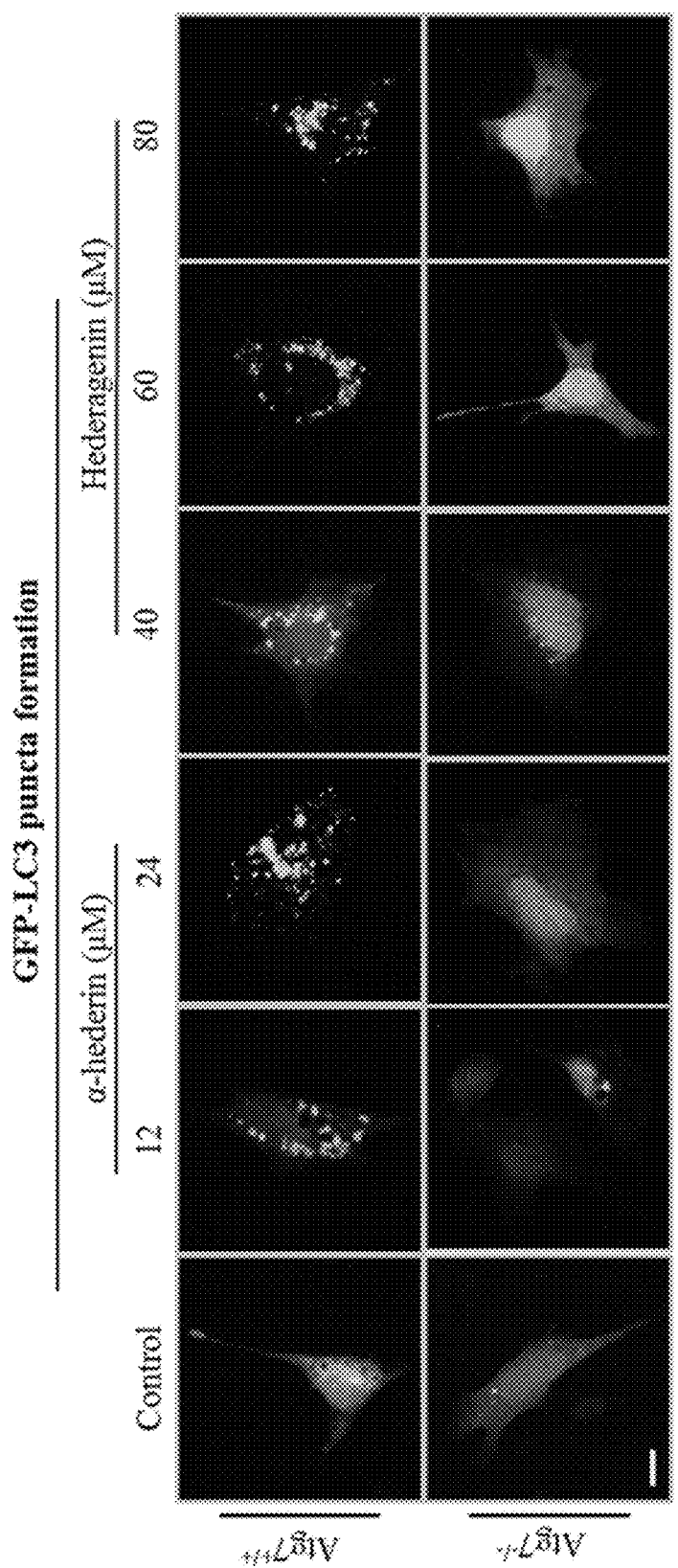
FIGS. 25A and 25B show the autophagic effect of hederagenin and α-hederin in GFP-LC3 transfected ATG7 wild-type (Atg7$^{+/+}$) and ATG7 deficient (Atg7$^{-/-}$) MEFs (mouse embryonic fibroblasts).
Figure 25B:
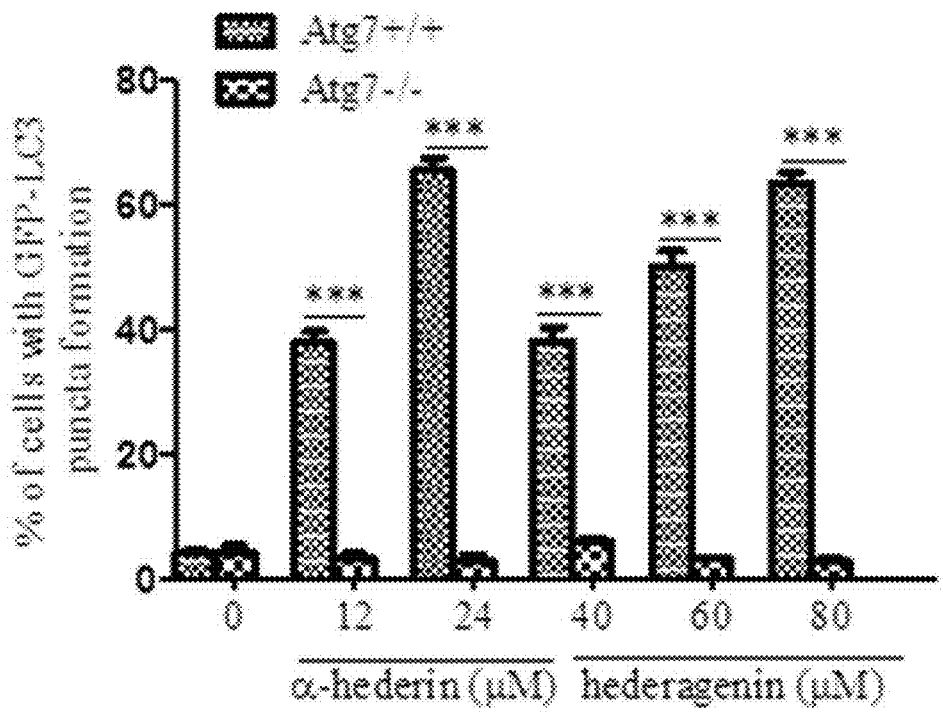
Figure 26A:
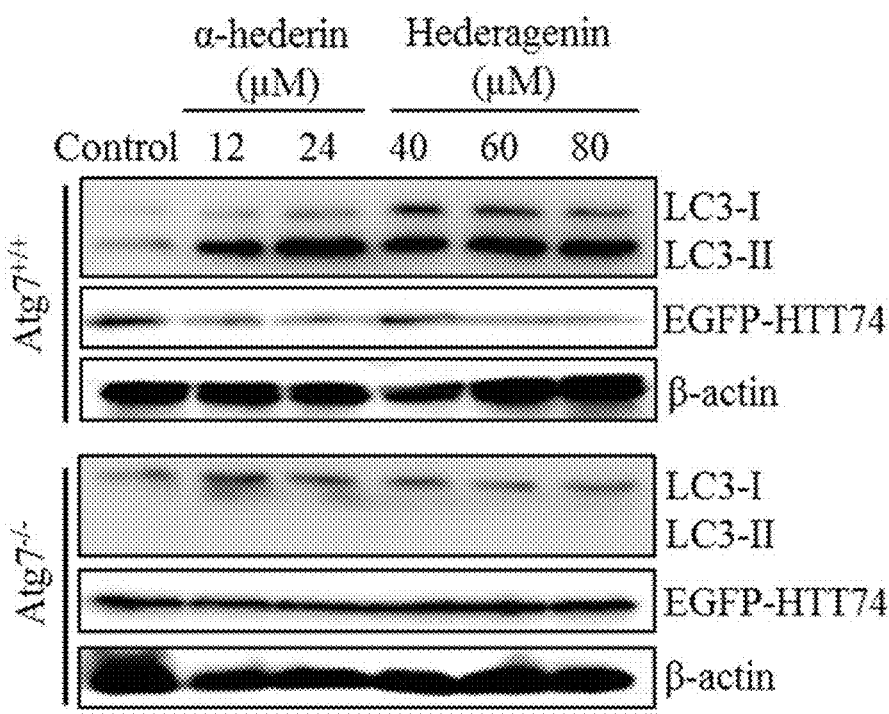
FIGS. 26A, 26B and 26C show the effect of hederagenin and α-hederin on the conversion of LC3 and HTT inclusion (EGFP-HTT 74) clearance in Atg7$^{+/+}$ and Atg7$^{-/-}$ MEFs with Western blotting analysis. The cells were treated with 12 μM or 24 μM α-hederin, or 40 μM, 60 μM or 80 μM hederagenin for 24 h.
Figure 26B:
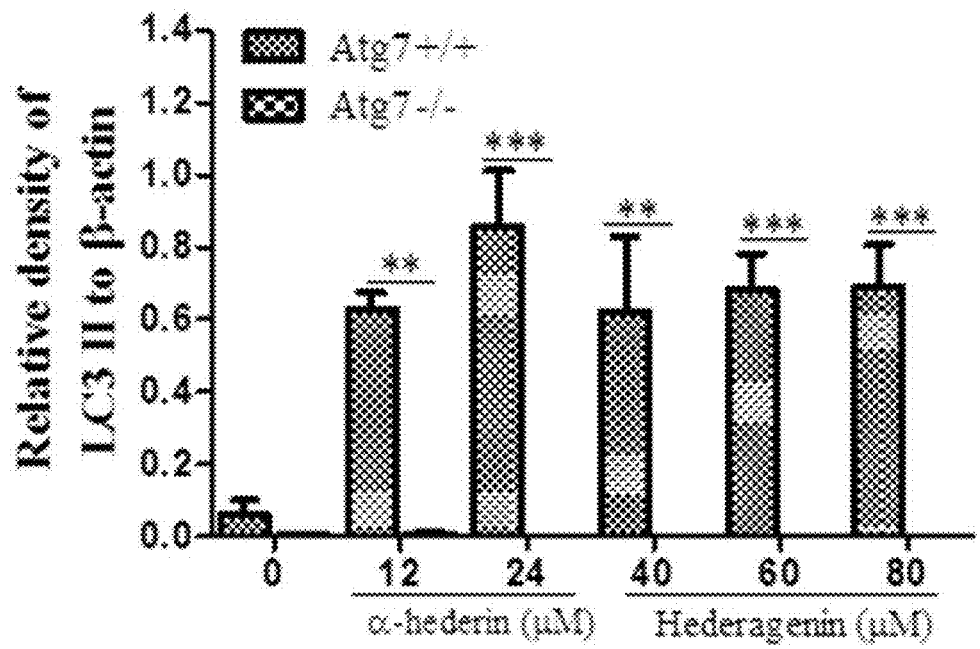
Figure 26C:
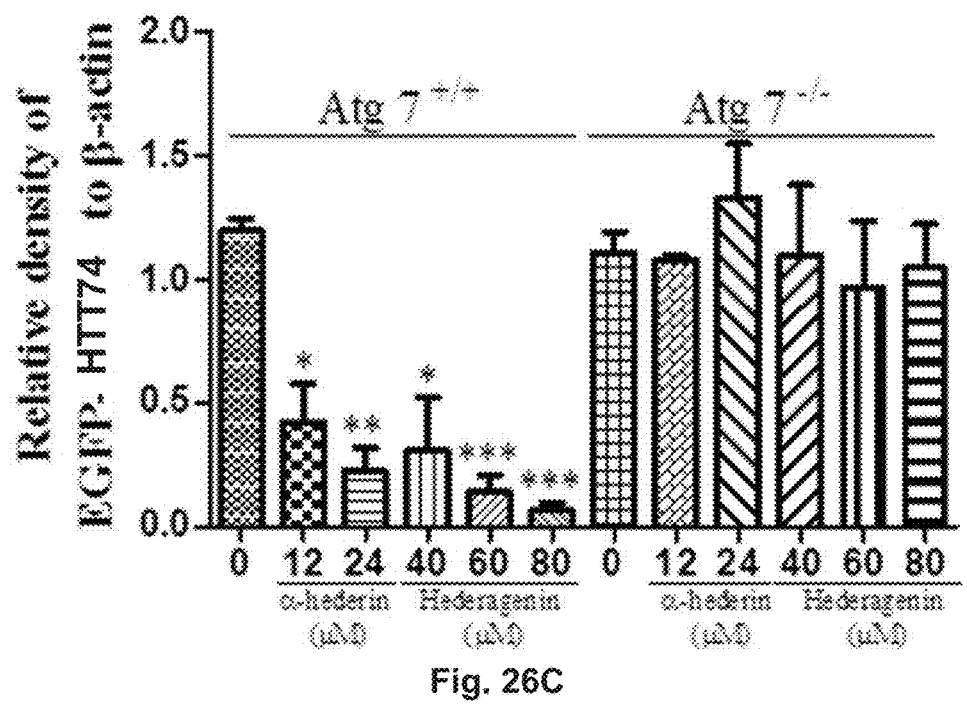

As revealed by fluorescent microscopic analysis in FIGS. 25A and 25B, both hederagenin and α-hederin significantly increase the GFP-LC3-II puncta formation in ATG7-wild type (ATG7+/+), but not in ATG7-knockout (ATG7−/−) mouse embryonic fibroblasts (MEFs), which is resistant to autophagy induction (Komatsu, M. et al., J Cell Biol 2005, 169:425-434). Western blots results further showed that both compounds induce a significant increased protein expression of LC3-II in ATG7+/+, but not in ATG7−/− MEFs (FIGS. 26A to 26C). The results confirmed the ATG7-dependent autophagic properties of hederagenin and α-hederin.

The autosomal-dominant neurodegenerative disorder, Huntington's disease (HD), is caused by a mutation in a single gene, which resulted in a more than 35 number of CAG trinucleotide repeats and finally a long polyglutamine tract (polyQ) located in the N-terminus of the huntingtin protein (HTT). This kind of toxic and aggregate-prone protein is inaccessible to the small barrel of proteasome and contributes to various human neurodegenerative diseases. However, recent studies have demonstrated the protective role of autophagic degradation of the mutant huntingtin proteins in a variety of models. Therefore, the potential protective effect of hederagenin and α-hederin in facilitating the autophagic degradation of mutant disease proteins in cellular models has been evaluated.

Figure 27A:
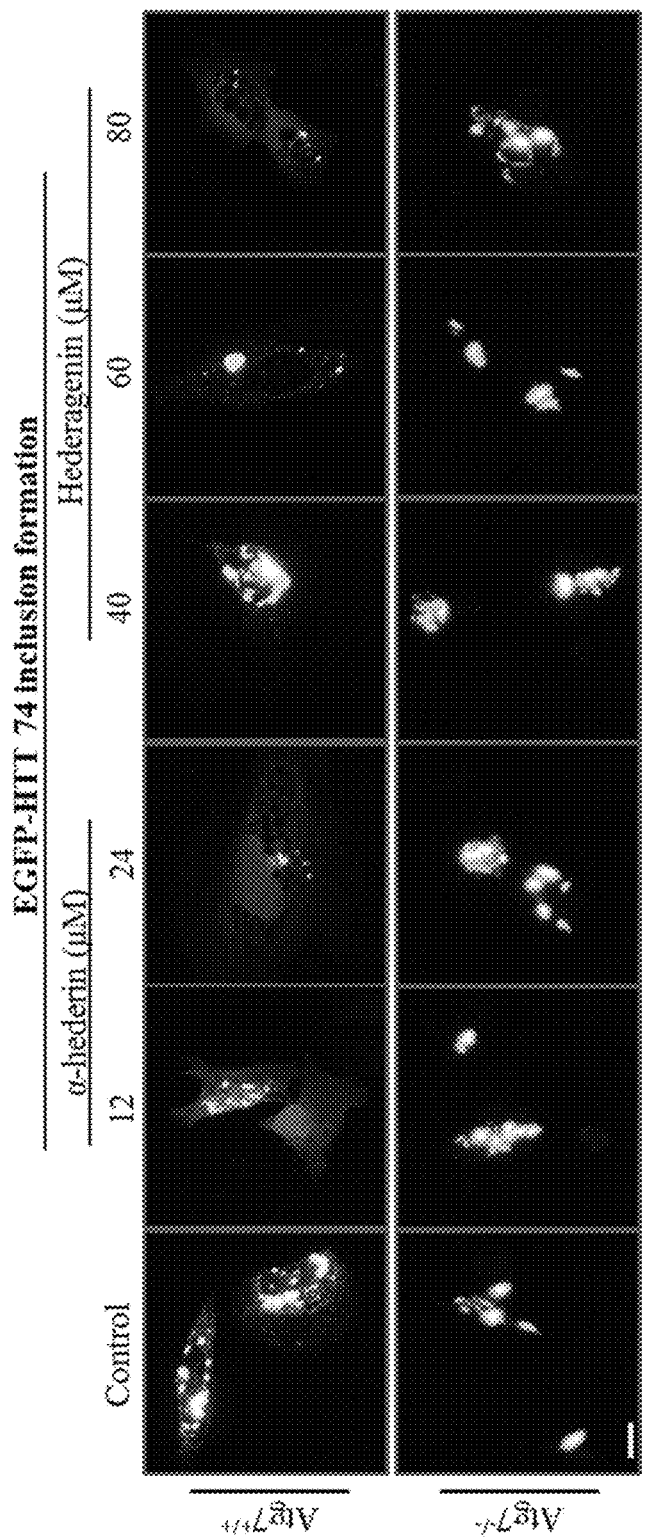
FIGS. 27A and 27B show the effect of hederagenin and α-hederin on HTT inclusion in EGFP-HTT 74 transfected Atg7$^{+/+}$ and Atg7$^{-/-}$ MEFs. The cells were treated with 12 μM or 24 μM α-hederin, or 40 μM, 60 μM or 80 μM hederagenin for 24 h.
Figure 27B:
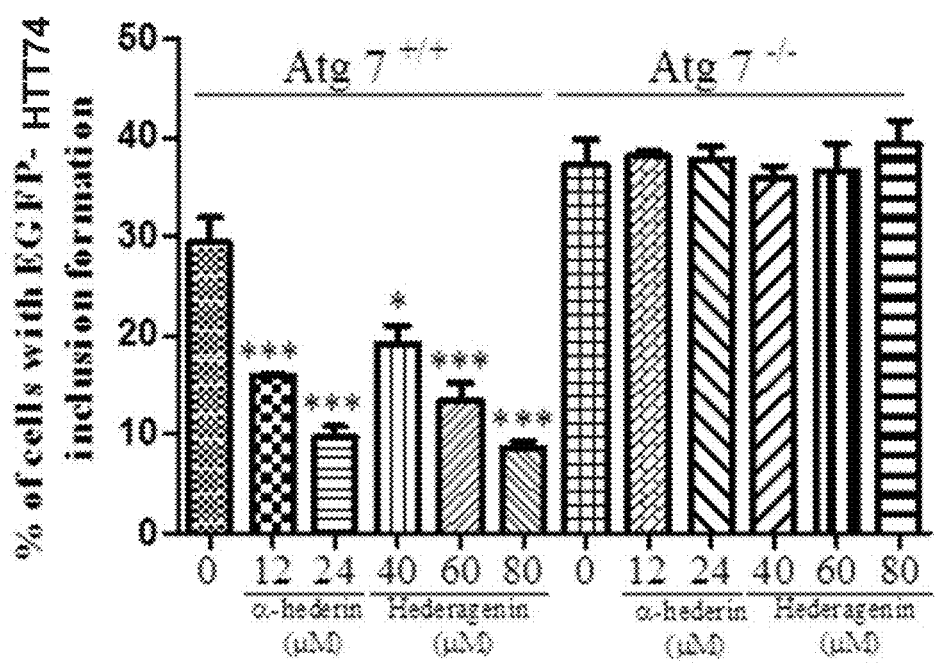

To begin, ATG7-wild type or -knockout MEFs were transiently overexpressed with the EGFP-tagged mutant huntingtin with 74 CAG trinucleotide repeats (EGFP-HTT 74) before treatment (Ravikumar, B. et al., Nat Genet 2004, 36:585-595, Ravikumar, B. et al., Hum Mol Genet 2002, 11:1107-1117). As demonstrated in FIGS. 26A to 26C, both hederagenin and α-hederin facilitate the inclusion clearance of overexpressed mutant huntingtin in ATG7+/+ but not ATG7−/− MEFs, suggesting the autophagy (ATG7) dependent degradation of mutant EGFP-HTT74. Furthermore, a higher percentage of cells with fluorescence mutant huntingtin inclusion formation was found in ATG−/− MEFs when compared with ATG7+/+ MEFs after treatment, suggesting the protective autophagic role on the clearance of mutant huntingtin inclusion in wild type ATG7 MEFs by both hederagenin and α-hederin (FIGS. 27A and 27B). Consistently, both hederagenin and α-hederin facilitate the clearance of overexpressed huntingtin in PC-12 cellular model transiently overexpressed with the EGFP-HTT 74

Figure 28A:
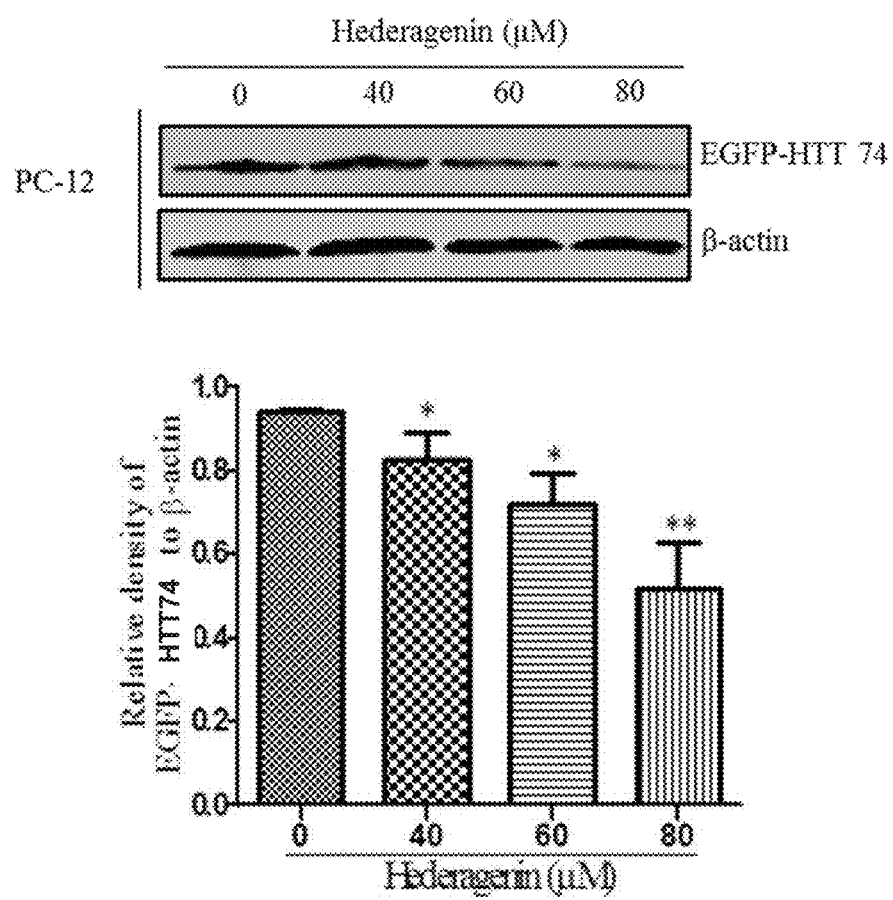
FIGS. 28A and 28B show the effect of hederagenin and α-hederin on HTT inclusion in EGFP-HTT 74 transfected PC-12 cells with Western blotting analysis.
Figure 28B:
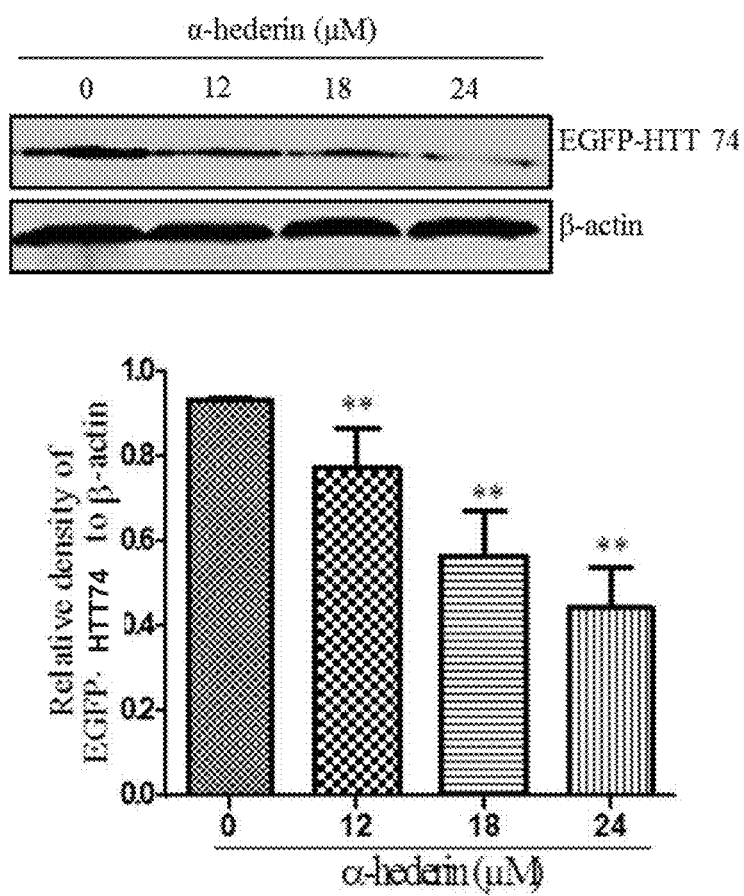

(FIGS. 28A and 28B). These results suggested the potential neuro-protective role of the compounds in their future therapeutic application.

Example 9

Hederagenin (Triterpenoid of Formula (VI)) and α-Hederin (Triterpenoid of Formula (V)) Facilitate the Degradation of Mutant A53T α-Synuclein (α-Syn) in Doxycycline (Dox)-Inducible Cellular Model Materials and Methods Bimolecular Fluorescence Complementation (BiFC) Assay: Both (1) non-fluorescent GFP-N terminal (GFP-N-α-syn), or (2) non-fluorescent GFP-C terminal (GFP-C-α-syn) plasmids were generous gifts from Pamela J. McLean (Department of Neuroscience, Mayo Clinic Florida, Jacksonville, Fla., USA). HeLa cells transfected with both GFP-N-α-syn and GFP-C-α-syn plasmids were incubated at 37° C. for 4 h. Cells were then subjected to different concentration of hederagenin or α-hederin treatments for a further 24 h in a humidified incubator at 30° C. (Outeiro, T. F. et al., PLoS One 2008, 3:e1867). Green fluorescent signal which indicates the reconstitution of complete GFP proteins was detected by flow analysis (BD FACSAria III, San Jose, Calif., USA).

Protein extraction and Western blots: Cells were harvested by RIPA lysis buffer (Cell Signaling Technologies, Beverly, Mass., USA), and with the final protein concentrations measured by using Bradford reagent (Bio-Rad, Hercules, Calif., USA). After electrophoresis for protein band separation, proteins were transferred to the nitrocellulose membrane which was blocked with 5% non-fat dried milk immediately after protein transfer. Corresponding primary antibodies, followed by the addition of HRP-conjugated secondary antibodies, were incubated with the protein membrane with constant shaking. Visualization of protein band pattern was performed by using the ECL Western Blotting Detection Reagents (Invitrogen, Paisley, Scotland). Band intensities were quantified by using the software, ImageJ (ImageJ 1.46r; National Institutes of Health, Bethesda, Md., USA).

Results

Figure 29A:
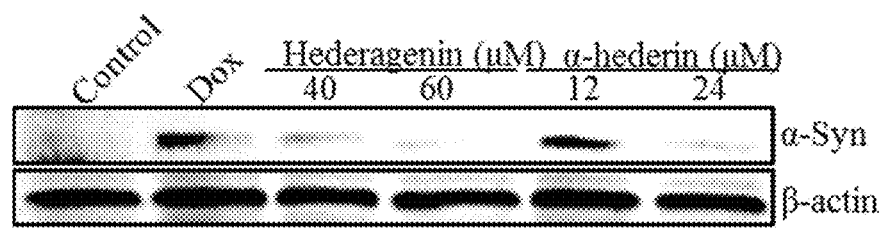
FIGS. 29A and 29B show the effect of hederagenin and α-hederin on doxycycline-induced expression of myc-tagged-mutant α-synuclein in PC-12 cells. The cells were subjected to Dox induction before being treated with 40 μM or 60 μM hederagenin, or 12 μM or 24 μM α-hederin.
Figure 29B:
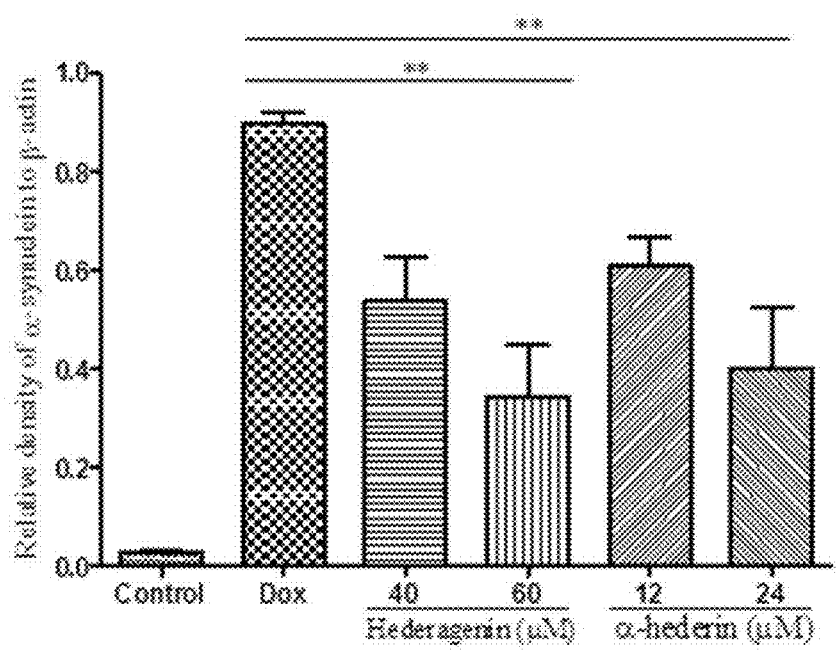

Degeneration of dopaminergic neurons is one of the common pathological features of PD. This degeneration is often accompanied by the cytoplasmic inclusion formation of Lewy bodies which contain fibrillar aggregates of α-syn. The proto-fibrillization rate of mutated α-syn is higher than its wild-type α-syn protein, while the fibrillation rate of A53T mutant α-syn is higher than the A30P mutant α-syn (Conway, K. A. et al., Proc Natl Acad Sci USA 2000, 97:571-576, Conway, K. A. et al., Biochemistry-Us 2000, 39:2552-2563). In fact, A53T mutation in the α-syn gene was found in early onset PD, and mutated forms of α-syn at high concentrations were susceptible to self-aggregation (Wood, S. J. et al., J Biol Chem 1999, 274:19509-19512). Since α-Syn aggregation was found in both classical and autosomal dominant early-onset PD (Recchia, A. et al., FASEB J 2004, 18:617-626), through establishing a doxycycline (Dox)-inducible mutant A53T α-syn expression cellular system (Sarkar, S. et al., J Biol Chem 2007, 282:5641-5652), it has been examined if hederagenin and α-hederin facilitate the degradation of mutated α-syn in vitro. In this cellular model, the overexpression of A53T mutant α-syn was induced by the addition of doxycycline (Dox). In FIGS. 29A and 29B, while 1 µg/ml of Dox induced an overexpression of myc-tagged-A53T-α-syn in cells, both hederagenin and α-hederin facilitate the clearance of the overexpressed mutant α- in PC-12 cells after induction of Dox.

Figure 30A:
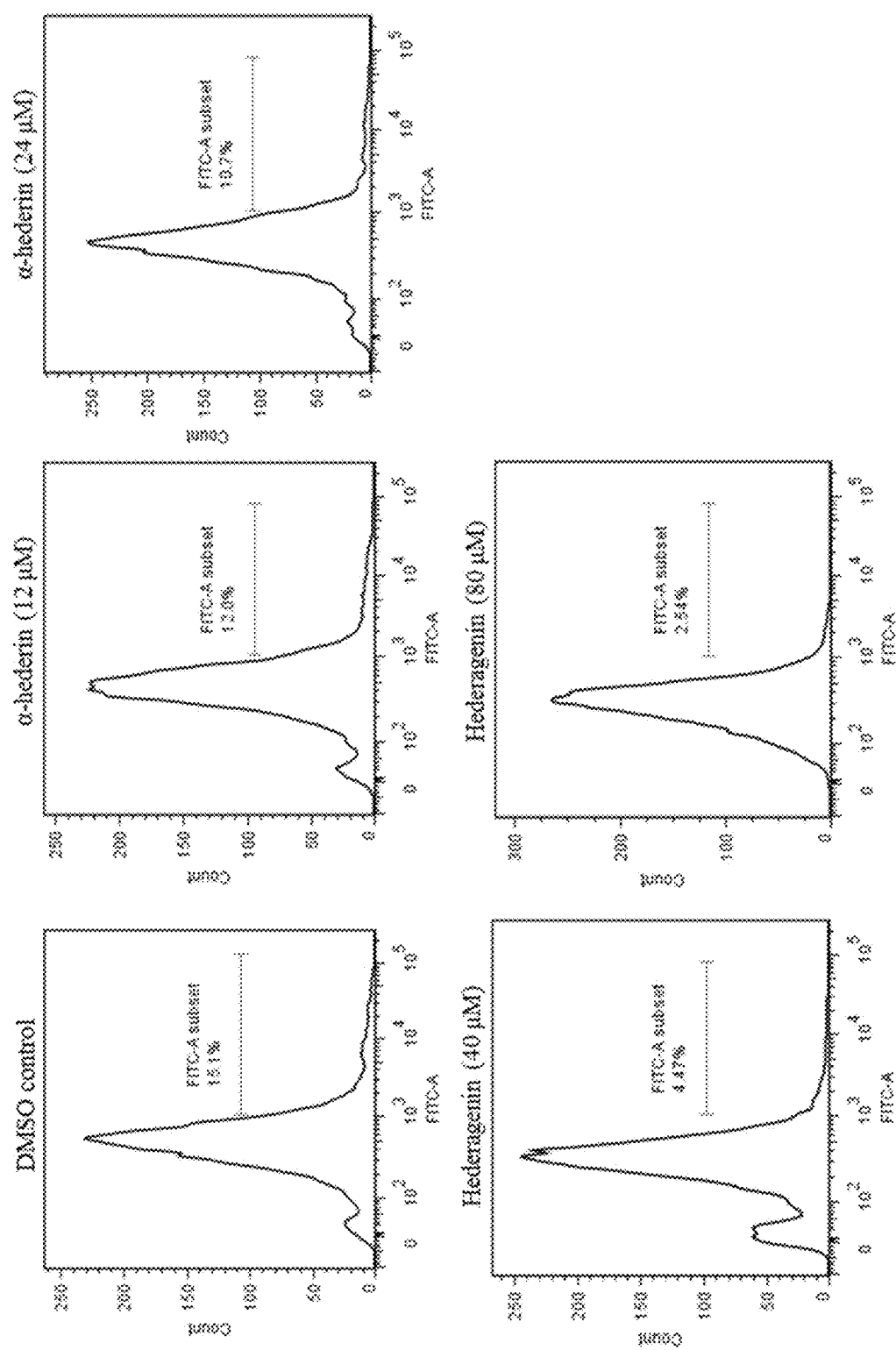
FIGS. 30A and 30B show the effect of hederagenin and α-hederin on the oligomerization of α-synuclein in transfected HeLa cells with bimolecular fluorescence complementation (BiFC) assay. The cells were treated with 40 μM or 80 μM hederagenin, or 12 μM or 24 μM α-hederin at 37° C. for 24 h.
Figure 30B:
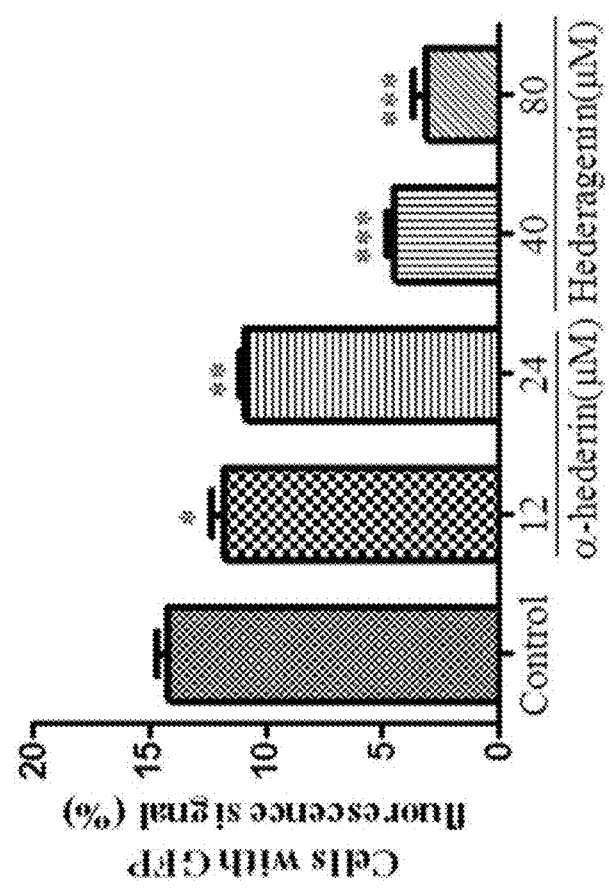

In addition to mutation of α-syn, oligomerization of α-syn was reported to contribute to neurotoxicity and pathogenesis of PD by permeating and disrupting the lipid bilayers cellular membranes. To this end, bimolecular fluorescence complementation (BiFC) model, which quantitate the degree of oligomerization of α-syn was set up (Outeiro, T. F. et al., PLoS One 2008, 3:e1867). In this model, α-syn was fused with either 1) non-fluorescent GFP-N terminal (GFP-N-α-syn), or 2) non-fluorescent GFP-C terminal (GFP-C-α-syn) fragment for in vitro quantitation of the oligomerization of α-syn. In general, upon the oligomerization of α-syn, the 2 incomplete non-fluorescent N-terminal-GFP and C-terminal-GFP fragments reconstitute into complete green fluorophore, and give positive GFP fluorescent signal which could be quantitated by flow analysis. As revealed by a decrease in the fluorescence intensity showed in FIGS. 30A and 30B, both hederagenin and α-hederin inhibit the oligomerization of α-syn in the BiFC assay, with hederagenin more potent in the inhibition when compared to α-hederin, suggesting the protective role of the 2 active components from *Hedera helix* in modulation of PD.

Example 10

Hederagenin (Triterpenoid of Formula (VI)) and α-Hederin (Triterpenoid of Formula (V)) Rescue Cells from MPTP-Induced Cell Death Materials and Methods Cytotoxicity Assays and Flow Cytometry: Cell viability was measured by using the MTT method (3-[4,5-dimethylthiazol-2-yl]-2,5-diphenyl tetrazolium bromide) as described previously (Wu, A. G. et al. Int J Mol Sci 2013, 14:22618-22641). Absorbance (OD) of cell samples was obtained by spectrophotometer at 570 nm. The percentage of cell viability was calculated by using the formula: cell viability (%)=cells number$_{treated}$/cells number$_{DMSO}$ control×100. All MTT data were calculated from three independent experiments. Cell viability was also measured by flow cytometry using the Annexin V staining kit (BD Biosciences, San Jose, Calif., USA). In brief, PC-12 cells treated with hederagenin and α-hederin were analyzed by multi-parametric flow cytometry using FITC-Annexin V and/or propidium iodide staining (BD Biosciences, San Jose, Calif., USA) by following manufacturer's instructions. Flow cytometry was then carried out using a FACSCalibur flow cytometer (BD Biosciences). Data acquisition and analysis were performed with CellQuest (BD Biosciences).

Results

Figure 31:
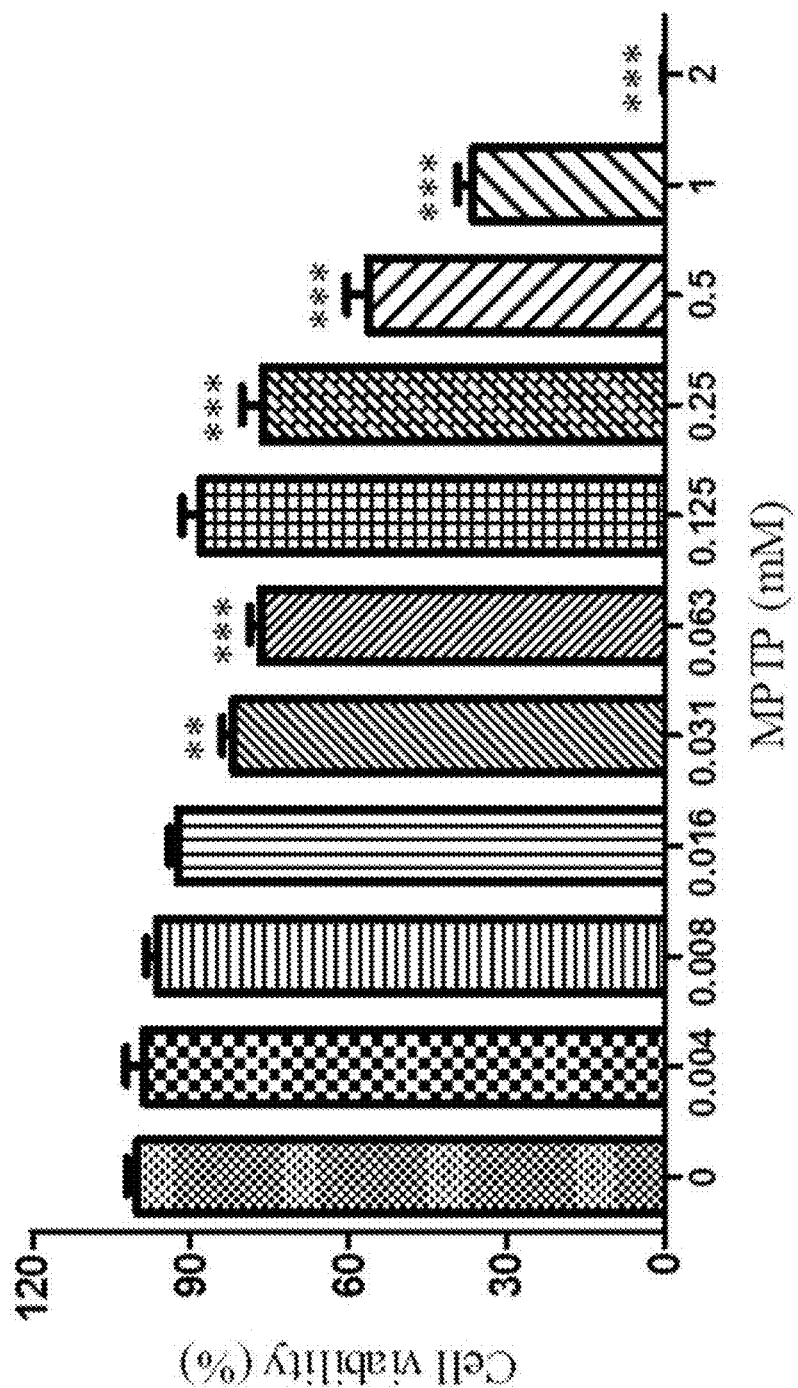
FIG. 31 is a diagram showing the cell viability of PC-12 cells treated with different concentrations of MPTP in a range from 0 mM to 2 mM for 48 h via MTT analysis.
Figure 32:
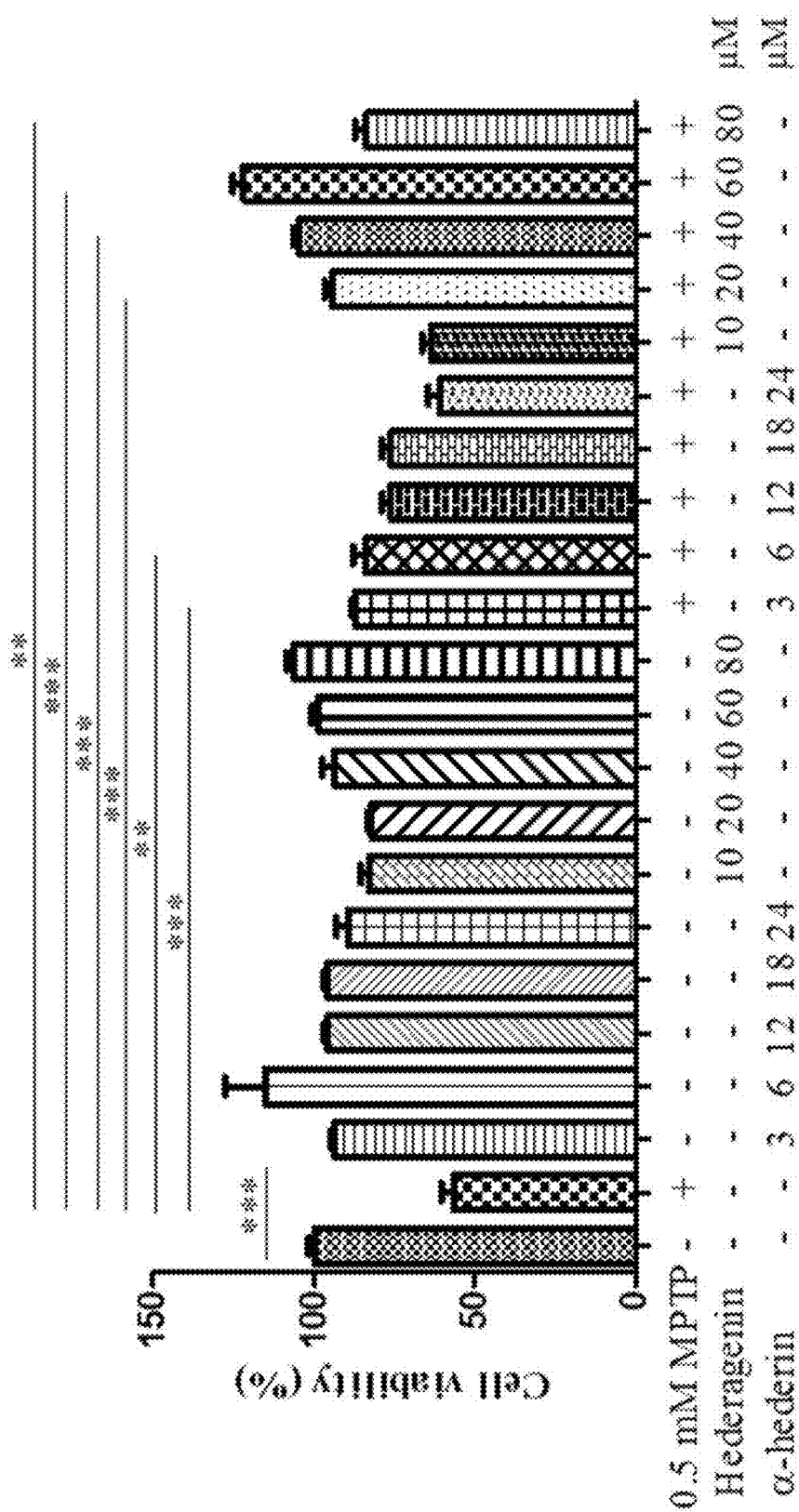
FIG. 32 is a diagram showing the effect of hederagenin and α-hederin on cell viability of PC-12 cells pre-treated with 0 mM MPTP or 0.5 mM MPTP. The concentration of hederagenin used was from 10 μM to 80 μM and the concentration of α-hederin used was from 3 μM to 24 μM.
Figure 33A:
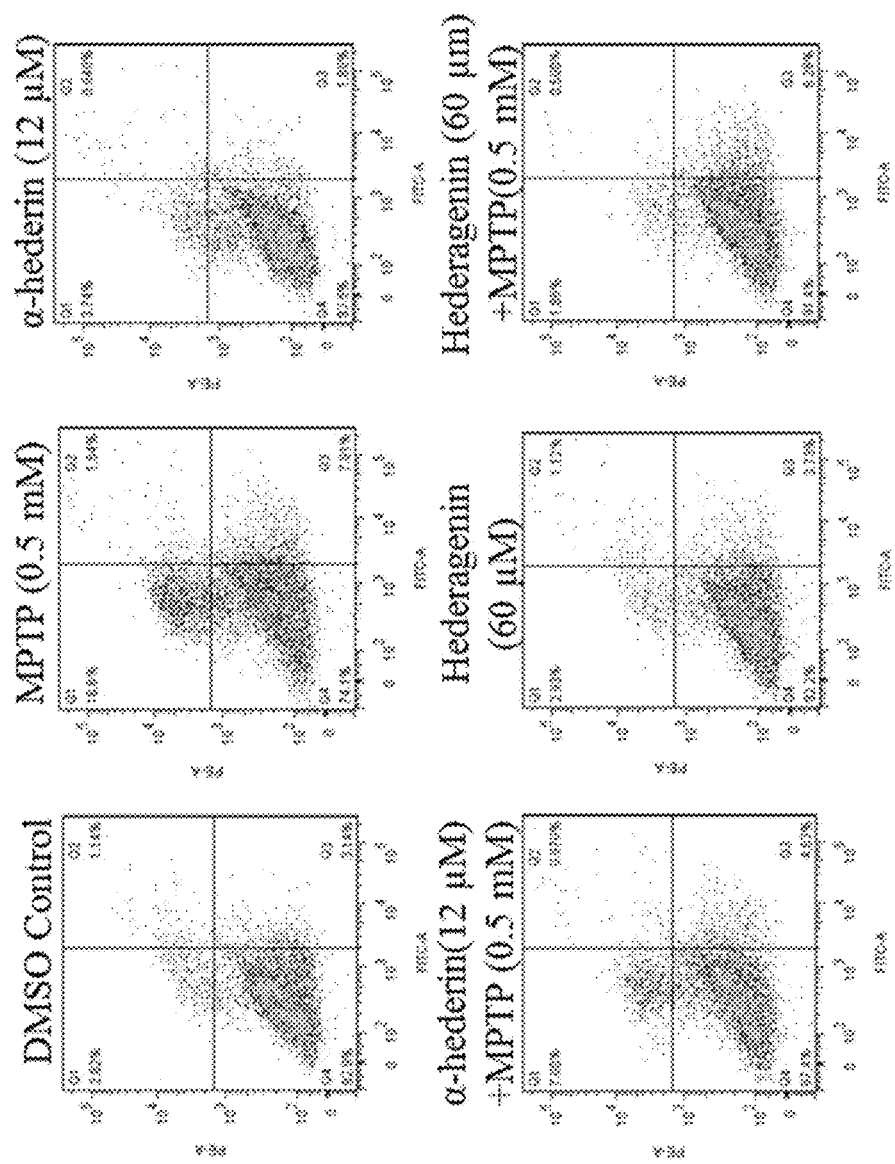
FIGS. 33A and 33B show the effect of 60 μM hederagenin and 12 μM α-hederin in PC-12 cells which were pre-treated with 0 mM MPTP or 0.5 mM MPTP with flow cytometry analysis.
Figure 33B:
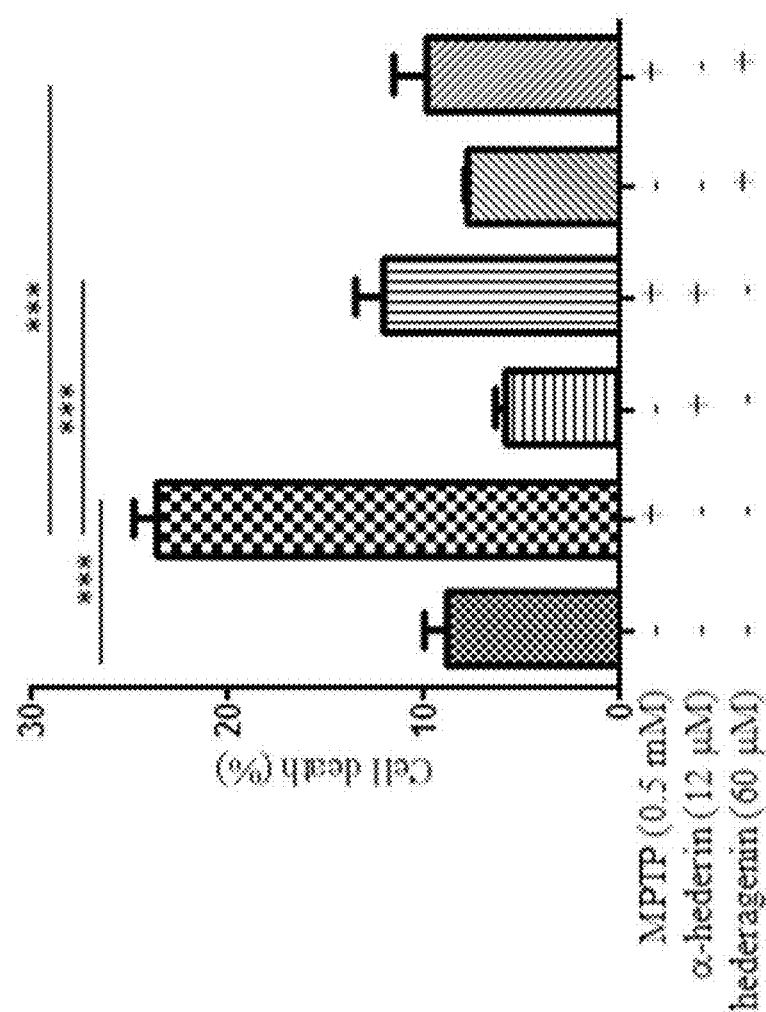

To begin, the protective effect of hederagenin and α-hederin in cytotoxicity cellular model induced by MPTP was investigated. Firstly, the percentage of cell viability under MPTP treatments (0 to 2 mM) was determined by MTT assay (FIG. 31). PC-12 cells were then treated with 0.5 mM of MPTP to induce toxicity in cells (Wang, S. et al., Mol Neurobiol 2015, 51:718-728). As shown in FIG. 31, while MPTP induces cell death in PC-12 cells, the addition of hederagenin or α-hederin rescue cells from MPTP-induced cell death as revealed by an increased in cell density, MTT assay (FIG. 32) and flow cytometry analysis (FIGS. 33A and 33B). Furthermore, the lack of obvious cytotoxicity induced by hederagenin or α-hederin at their most effective concentrations of 80 μM and 24 μM, respectively, highly suggest the potential therapeutic use of both autophagic compounds as neuroprotective agents.

The invention claimed is:

1. A method for delaying the onset and/or delaying the progression of at least one neurodegenerative disease selected from the group consisting of Parkinson's disease and Huntington's disease in a subject suffering from the at least one neurodegenerative disease comprising the step of administering an effective amount of at least one triterpenoid to the subject which triterpenoid has a structure of Formula (V):

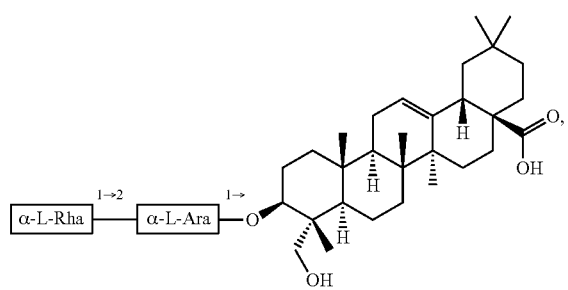

Formula (V)

or a structure of Formula (VI):

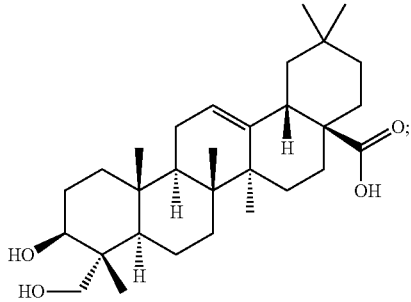

Formula (VI)

wherein the subject is a human and the at least one triterpenoid with the structure of Formula (V) or Formula (VI) reduces A53T α-synuclein protein levels and/or mutant huntingtin protein levels.

2. The method of claim 1, wherein the method comprises administering an effective amount of at least a first triterpenoid and a second triterpenoid, wherein the first triterpenoid has a structure of Formula (V):

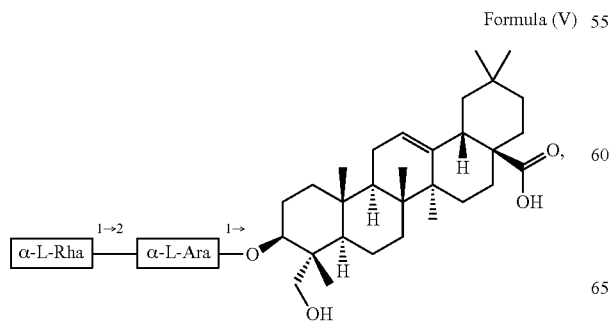

Formula (V)

and the second triterpenoid has a structure of Formula (VI):

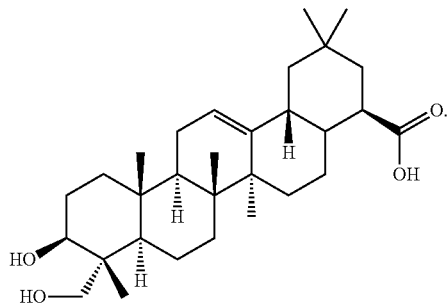

Formula (VI)

3. The method of claim 1, wherein the at least one triterpenoid is administered in form of an extract obtained from *Hedera helix*.

4. The method of claim 1, wherein the administration of the at least one triterpenoid induces autophagy through the activation of the AMPK-mTOR dependent autophagy inducing pathway.

5. The method of claim 1, wherein the at least one neurodegenerative disease is Huntington's disease.

6. A method for inducing autophagy in neuronal cells of a subject suffering from a neurodegenerative disease selected from the group consisting of Parkinson's disease and Huntington's disease comprising contacting the cells with an effective amount of at least one triterpenoid having a structure of Formula (V):

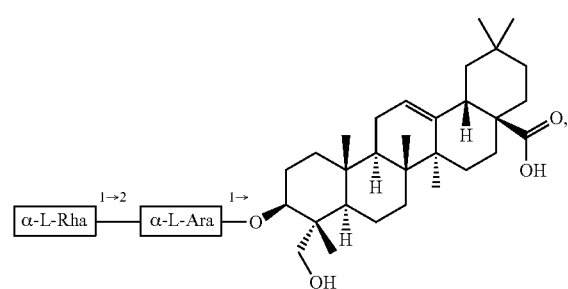

Formula (V)

or a structure of Formula (VI):

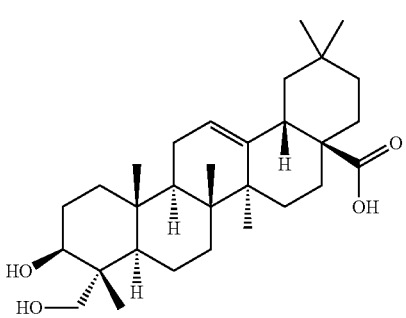

Formula (VI)

wherein the subject is a human and the at least one triterpenoid with the structure of Formula (V) or Formula (VI) reduces A53T α-synuclein protein levels and/or mutant huntingtin protein levels.

7. The method of claim 6, wherein autophagy is induced through the activation of the AMPK-mTOR dependent autophagy inducing pathway.

8. The method of claim 6, wherein the cells are contacted with the triterpenoid having the structure of Formula (V):

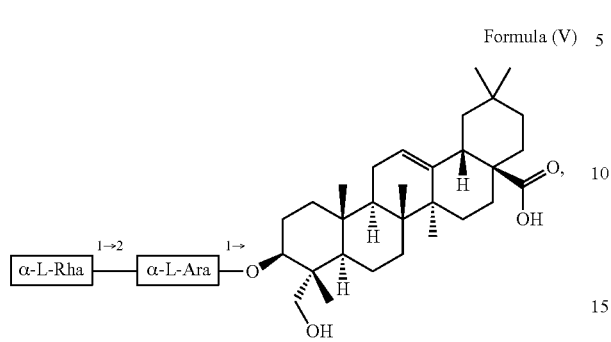

Formula (V)

in a concentration of about 12 μM to about 30 μM, or contacted with the triterpenoid having the structure of Formula (VI):

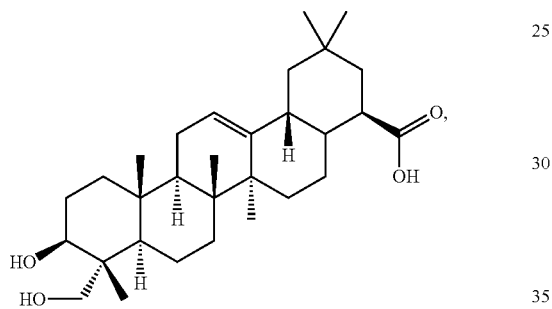

Formula (VI)

in a concentration of about 40 μM to about 100 μM.

9. A method of reducing A53T α-synuclein protein levels in a subject suffering from Parkinson's disease comprising the step of administering an effective amount of a *Hedera helix* extract comprising at least one triterpenoid having a structure of Formula (V):

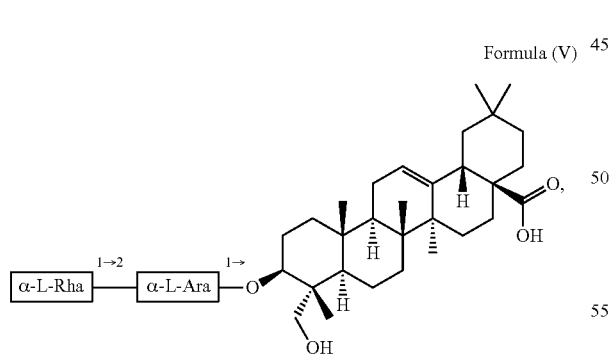

Formula (V)

or a structure of Formula (VI):

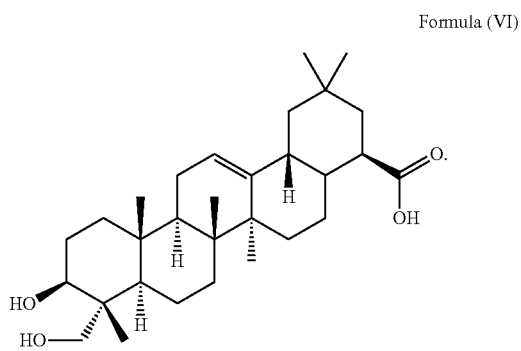

Formula (VI)

10. A method of reducing mutant huntingtin protein levels in a subject suffering from Huntington's disease comprising the step of administering an effective amount of a *Hedera helix* extract comprising at least one triterpenoid having a structure of Formula (V):

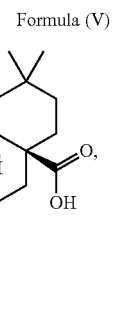

Formula (V)

or a structure of Formula (VI):

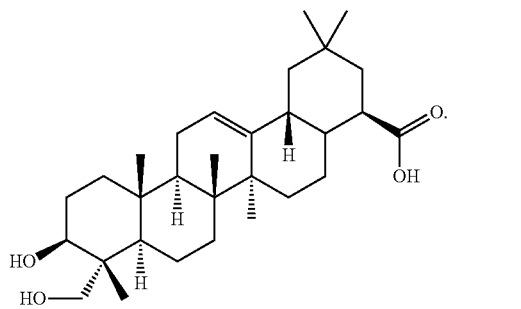

Formula (VI)

* * * * *